(12) United States Patent
Overbeek et al.

(10) Patent No.: US 12,398,098 B2
(45) Date of Patent: *Aug. 26, 2025

(54) WATERBORNE CROSSLINKER COMPOSITION

(71) Applicant: COVESTRO (NETHERLANDS) B.V., Geleen (NL)

(72) Inventors: Gerardus Cornelis Overbeek, Geleen (NL); Patrick Johannes Maria Stals, Geleen (NL); Daan Van Der Zwaag, Geleen (NL); Alfred Jean Paul Bückmann, Geleen (NL); Kristel De Vos Verschuren, Geleen (NL); Stella Josette Van Dijk, Geleen (NL); Jan Van Riel, Geleen (NL); Rob Looijmans, Geleen (NL)

(73) Assignee: Covestro (Netherlands) B.V., Geleen (NL)

( * ) Notice: Subject to any disclaimer, the term of this patent is extended or adjusted under 35 U.S.C. 154(b) by 640 days.

This patent is subject to a terminal disclaimer.

(21) Appl. No.: 17/791,765

(22) PCT Filed: Jan. 21, 2021

(86) PCT No.: PCT/EP2021/051385
§ 371 (c)(1),
(2) Date: Jul. 8, 2022

(87) PCT Pub. No.: WO2021/148563
PCT Pub. Date: Jul. 29, 2021

(65) Prior Publication Data
US 2023/0193057 A1    Jun. 22, 2023

(30) Foreign Application Priority Data

Jan. 22, 2020  (EP) .................................. 20153154
Jan. 22, 2020  (EP) .................................. 20153159
Jan. 22, 2020  (EP) .................................. 20153239
Jan. 22, 2020  (EP) .................................. 20153240
Jan. 22, 2020  (EP) .................................. 20153242
Jan. 22, 2020  (EP) .................................. 20153245
Jan. 22, 2020  (EP) .................................. 20153246
(Continued)

(51) Int. Cl.
*C07D 203/10*    (2006.01)
*C07D 251/32*    (2006.01)
(Continued)

(52) U.S. Cl.
CPC ......... *C07D 203/10* (2013.01); *C07D 251/32* (2013.01); *C07D 403/12* (2013.01);
(Continued)

(58) Field of Classification Search
CPC .. C07D 203/10; C07D 251/32; C07D 403/12; C07D 403/14; C07D 413/14;
(Continued)

(56) References Cited

U.S. PATENT DOCUMENTS 3,329,674 A    7/1967  Bulbenko et al.
3,337,533 A    8/1967  Ham
(Continued)

FOREIGN PATENT DOCUMENTS

CN    1606574 A    4/2005
CN    1720223 A    1/2006
(Continued)

OTHER PUBLICATIONS

Dahlquist et al., "Contact allergy to trimethylolpropane triacrylate (TMPTA) in an aziridine plastic hardener", Contact Dermatitis, 1983, pp. 122-124, vol. 9.
Fei et al., "Properties and Curing Kinetic of Acrylic Resin Cured with Aziridine Crosslinker", Chinese Journal of Synthetic Chemistry, 2002, pp. 120-125, vol. 10, Issue 2.
Haitao et al., "Synthesis and Application of Aziridine Crosslinking Agent in Waterborne Coatings", Shanghai Coatings, 2013, 7 pages, vol. 51, No. 10.
Jiao, "Preparation of Waterborne Polyurethane Based on Renewable Resources and Its Film Properties", Masteral Dissertation, Dalian University of Technology, 2010, 79 pages.
Lee et al., "Preparation and characterization of acrylic pressure-sensitive adhesives based on UV and heat curing systems", International Journal of Adhesion and Adhesives, 2017, 21 pages.
(Continued)

*Primary Examiner* — Heidi R Kelley
*Assistant Examiner* — Adam J Berro
(74) *Attorney, Agent, or Firm* — The Webb Law Firm

(57) ABSTRACT

The present invention relates to a multi-aziridine crosslinker composition, characterized in that the multi-aziridine crosslinker composition is an aqueous dispersion having a pH ranging from 8 to 14 and comprises a multi-aziridine compound in dispersed form, wherein said multi-aziridine compound has: a. from 2 to 6 of the following structural units A: whereby $R_1$ is H, $R_2$ and $R_4$ are independently chosen from H or an aliphatic hydrocarbon group containing from 1 to 4 carbon atoms, R a is an aliphatic hydrocarbon group containing from 1 to 4 carbon atoms, m is 1, b. one or more linking chains wherein each one of these linking chains links two of the structural units A; and c. a molecular weight in the range from 500 to 10000 Daltons wherein the molecular weight is determined using MALDI-TOF mass spectrometry according to the description.

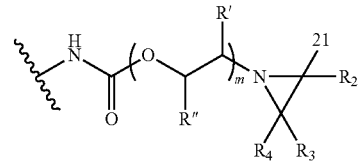

25 Claims, No Drawings

(30) Foreign Application Priority Data

| Jan. 22, 2020 | (EP) | 20153249 |
|---|---|---|
| Jan. 22, 2020 | (EP) | 20153250 |
| Jan. 22, 2020 | (EP) | 20153251 |
| Jan. 22, 2020 | (EP) | 20153253 |
| Jan. 24, 2020 | (EP) | 20153628 |
| Jan. 24, 2020 | (EP) | 20153630 |
| Jul. 24, 2020 | (EP) | 20187717 |

(51) Int. Cl.

| C07D 403/12 | (2006.01) |
|---|---|
| C07D 403/14 | (2006.01) |
| C07D 413/14 | (2006.01) |
| C07D 487/14 | (2006.01) |
| C08F 220/18 | (2006.01) |
| C08G 18/02 | (2006.01) |
| C08G 18/08 | (2006.01) |
| C08G 18/12 | (2006.01) |
| C08G 18/22 | (2006.01) |
| C08G 18/24 | (2006.01) |
| C08G 18/28 | (2006.01) |
| C08G 18/30 | (2006.01) |
| C08G 18/32 | (2006.01) |
| C08G 18/34 | (2006.01) |
| C08G 18/38 | (2006.01) |
| C08G 18/42 | (2006.01) |
| C08G 18/44 | (2006.01) |
| C08G 18/48 | (2006.01) |
| C08G 18/66 | (2006.01) |
| C08G 18/67 | (2006.01) |
| C08G 18/73 | (2006.01) |
| C08G 18/75 | (2006.01) |
| C08G 18/76 | (2006.01) |
| C08G 18/79 | (2006.01) |
| C08G 18/83 | (2006.01) |
| C08K 5/3412 | (2006.01) |
| C08K 5/3492 | (2006.01) |
| C08L 63/00 | (2006.01) |
| C09D 7/20 | (2018.01) |
| C09D 7/45 | (2018.01) |
| C09D 7/63 | (2018.01) |
| C09D 7/65 | (2018.01) |
| C09D 11/101 | (2014.01) |
| C09D 133/02 | (2006.01) |
| C09D 133/04 | (2006.01) |
| C09D 175/04 | (2006.01) |
| C09D 175/08 | (2006.01) |
| C09D 175/12 | (2006.01) |

(52) U.S. Cl.
CPC ......... *C07D 403/14* (2013.01); *C07D 413/14* (2013.01); *C07D 487/14* (2013.01); *C08F 220/1804* (2020.02); *C08G 18/027* (2013.01); *C08G 18/0823* (2013.01); *C08G 18/0866* (2013.01); *C08G 18/12* (2013.01); *C08G 18/227* (2013.01); *C08G 18/246* (2013.01); *C08G 18/282* (2013.01); *C08G 18/2825* (2013.01); *C08G 18/283* (2013.01); *C08G 18/2865* (2013.01); *C08G 18/2875* (2013.01); *C08G 18/302* (2013.01); *C08G 18/3228* (2013.01); *C08G 18/3231* (2013.01); *C08G 18/3275* (2013.01); *C08G 18/348* (2013.01); *C08G 18/3842* (2013.01); *C08G 18/4291* (2013.01); *C08G 18/44* (2013.01); *C08G 18/4808* (2013.01); *C08G 18/4825* (2013.01); *C08G 18/4854* (2013.01); *C08G 18/4862* (2013.01); *C08G 18/4879* (2013.01); *C08G 18/6692* (2013.01); *C08G 18/6715* (2013.01); *C08G 18/73* (2013.01); *C08G 18/755* (2013.01); *C08G 18/758* (2013.01); *C08G 18/765* (2013.01); *C08G 18/792* (2013.01); *C08G 18/798* (2013.01); *C08G 18/833* (2013.01); *C08K 5/3412* (2013.01); *C08K 5/34924* (2013.01); *C08K 5/34926* (2013.01); *C08L 63/00* (2013.01); *C09D 7/20* (2018.01); *C09D 7/45* (2018.01); *C09D 7/63* (2018.01); *C09D 7/65* (2018.01); *C09D 11/101* (2013.01); *C09D 133/02* (2013.01); *C09D 133/04* (2013.01); *C09D 175/04* (2013.01); *C09D 175/08* (2013.01); *C09D 175/12* (2013.01); *C08G 2150/00* (2013.01)

(58) Field of Classification Search
CPC ............ C07D 487/14; C08F 220/1804; C08G 18/027; C08G 18/0823; C08G 18/0866; C08G 18/12; C08G 18/282; C08G 18/2825; C08G 18/283; C08G 18/2865; C08G 18/3842; C08G 18/4291; C08G 18/4825; C08G 18/4854; C08G 18/4862; C08G 18/765; C08G 18/792; C08G 18/798; C08G 18/833; C08K 5/3412; C08K 5/34924; C08K 5/34926
See application file for complete search history.

(56) References Cited

U.S. PATENT DOCUMENTS

| 3,523,750 | A | 8/1970 | Tesoro |
| 3,560,415 | A | 2/1971 | Grögler et al. |
| 3,583,977 | A | 6/1971 | Uelzmann |
| 3,763,132 | A | 10/1973 | Meiser |
| 3,933,936 | A | 1/1976 | Smith et al. |
| 4,605,698 | A | 8/1986 | Briden |
| 5,106,993 | A | 4/1992 | Kania |
| 5,133,997 | A | 7/1992 | Maier et al. |
| 5,164,467 | A | 11/1992 | Kania |
| 5,241,001 | A | 8/1993 | Kania et al. |
| 5,258,481 | A | 11/1993 | Hesselmans et al. |
| 5,359,005 | A | 10/1994 | Kania et al. |
| 5,712,331 | A | 1/1998 | Ryang |
| 7,294,449 | B1 | 11/2007 | Guideman et al. |
| 7,396,891 | B2 | 7/2008 | Gray et al. |
| 8,318,855 | B2 | 11/2012 | Schafheutle et al. |
| 11,878,969 | B2* | 1/2024 | Overbeek ............ C09D 167/02 |
| 12,247,008 | B2* | 3/2025 | Stals ...................... C09D 7/20 |
| 2003/0229176 | A1 | 12/2003 | Trombetta et al. |
| 2006/0117991 | A1 | 6/2006 | Mayo et al. |
| 2006/0148980 | A1 | 7/2006 | Tielemans et al. |
| 2007/0298006 | A1 | 12/2007 | Tomalia et al. |
| 2008/0114096 | A1 | 5/2008 | Qu et al. |
| 2010/0227945 | A1 | 9/2010 | Bissinger et al. |
| 2011/0086180 | A1 | 4/2011 | Tielemans |
| 2015/0118501 | A1 | 4/2015 | Lu et al. |
| 2017/0218110 | A1 | 8/2017 | Arzt et al. |

FOREIGN PATENT DOCUMENTS

| CN | 1823110 A | 8/2006 |
| CN | 101365688 A | 2/2009 |
| CN | 101437863 A | 5/2009 |
| CN | 101619164 A | 1/2010 |
| CN | 102046688 A | 5/2011 |
| CN | 104080861 A | 10/2014 |
| CN | 104379618 A | 2/2015 |
| CN | 105143297 A | 12/2015 |
| CN | 105377918 A | 3/2016 |
| CN | 105705598 A | 6/2016 |
| CN | 107922762 A | 4/2018 |

(56) References Cited

FOREIGN PATENT DOCUMENTS

| | | |
|---|---|---|
| CN | 108084870 | 5/2018 |
| CN | 110023354 A | 7/2019 |
| CN | 110248977 A | 9/2019 |
| CN | 110607120 A | 12/2019 |
| CN | 112469755 A | 3/2021 |
| CN | 117015566 A | 11/2023 |
| CN | 117836343 A | 4/2024 |
| EP | 0 507 407 | 10/1992 |
| EP | 0 758 662 | 2/1997 |
| EP | 1 865 014 | 12/2007 |
| GB | 1344725 | 1/1974 |
| JP | 47-027971 | 8/1972 |
| JP | 51-141860 | 5/1976 |
| JP | 59-128291 | 7/1984 |
| JP | 11-500152 | 1/1999 |
| JP | 2012-529473 | 11/2012 |
| JP | 2015-505889 | 2/2015 |
| KR | 1020060066442 A | 6/2006 |
| WO | 2006/115547 | 11/2006 |
| WO | 2008069298 A1 | 6/2008 |
| WO | 2013/089927 | 6/2013 |
| WO | 2015/066868 | 5/2015 |
| WO | 2017216767 A1 | 12/2017 |
| WO | 2020/020714 | 1/2020 |

OTHER PUBLICATIONS

Qingfang et al., "Study on heat resistance of polyurethane-imide/organosilicon modified epoxy coatings", Synthetic Materials and Applications, 2018, 5 pages, vol. 47, No. 3.

Walsh et al., "Polyamine-Functional Sterically Stabilized Latexes for Covalently Cross-Linkable Colloidosomes", Langmuir, 2010, pp. 18039-18048, vol. 26(23).

Wang et al., "Pervaporation Properties to Aromatic/Non-Aromatic Hydrocarbon Mixtures of Cross-Linked Membranes of Copoly(methacrylates) with Pendant Phosphate and Carbamoylphosphonate Groups", Journal of Membrane Science, 2002, pp. 13-27, vol. 199.

Yoo et al., "Preparation of Acrylic Copolymers and Crosslinking Agents and Properties as a Film", Journal of Applied Polymer Science, 2009, pp. 1587-1594, vol. 112.

Zilin et al., "Effect of Crosslinking Agent on Waterborne Polyurethane Wet Friction Fixing Agent", Shandon Chemical Industry, 2019, pp. 1-4, vol. 8, Issue 14.

International Search Report for PCT/EP2021/051385 dated May 18, 2021 (4 pages).

Written Opinion of the ISA for PCT/EP2021/051385 dated May 18, 2021 (9 pages).

* cited by examiner

WATERBORNE CROSSLINKER COMPOSITION

"This application is the U.S. national phase of International Application No. PCT/EP2021/051385 filed Jan. 21, 2021 which designated the U.S. and claims priority to EP 20187717.2 filed Jul. 24, 2020, EP 20153628.1 filed Jan. 24, 2020, EP 20153630.7 filed Jan. 24, 2020, EP 20153154.8 filed Jan. 22, 2020, EP 20153159.7 filed Jan. 22, 2020, EP 20153239.7 filed Jan. 22, 2020, EP 20153240.5 filed Jan. 22, 2020, EP 20153242.1 filed Jan. 22, 2020, EP 20153245.4 filed Jan. 22, 2020, EP 20153246.2 filed Jan. 22, 2020, EP 20153249.6 filed Jan. 22, 2020, EP 20153250.4 filed Jan. 22, 2020, EP 20153251.2 filed Jan. 22, 2020, EP 20153253.8 filed Jan. 22, 2020, the entire contents of each of which are hereby incorporated by reference.

The present invention relates to multi-aziridine crosslinker compositions which can be used for crosslinking of carboxylic acid functional polymers dissolved and/or dispersed in an aqueous medium.

Coatings provide protection, aesthetic quality and new functionality to a wide range of substrates with tremendous industrial and household relevance. In this context, the need for coatings with improved resistances, like stain and solvent resistance, improved mechanical properties and improved adhesive strength is growing continuously. One or more of those properties can be enhanced by means of crosslinking. Many crosslinking mechanisms for polymeric binders have been studied over the years and for waterborne latex polymer dispersions, the most useful ones include isocyanate crosslinking of hydroxyl functional polymers, carbodiimide crosslinking of carboxylic acid functional polymers, melamine crosslinking, epoxy crosslinking and aziridine crosslinking of carboxylic acid functional polymers.

Waterborne binders are generally colloidal stabilized by carboxylic acid groups, and the coating properties can be improved by the use of carbodiimide or aziridine crosslinkers since they react with the carboxylic acid moieties of the polymer resulting in a crosslinked network. Of the state-of-the-art crosslinkers as mentioned above, aziridine crosslinkers are most versatile for room temperature curing of carboxylic acid functional polymers.

Traditional crosslinking approaches generally involve the use of reactive organic molecules of low molecular weight, occasionally dissolved in volatile organic solvents for reducing viscosity to facilitate accurate dosing and mixing of the crosslinker to/in the polymer composition to be crosslinked. Good miscibility of the crosslinker with the polymer composition is important for both the final properties (poor miscibility tends to give inefficient crosslinking) and for efficiency and convenience of the user of the material. However, the use of volatile organic solvents to reduce viscosity is undesirable since this will increase the VOC (Volatile Organic Compounds) levels. Further, the presence of solvents in the crosslinker composition will reduce the formulation latitude of the formulator of the coating composition and is therefore undesirable. It would therefore be beneficial to deliver multi-aziridine crosslinkers in water. At the same time, crosslinker performance needs to be preserved, in terms of crosslinking efficiency and storage stability, to remain commercially feasible in a variety of polymeric resins.

However, current state-of-the-art multi-aziridine crosslinkers lack stability in aqueous environment. For example, CX-100 (trimethylolpropane tris(2-methyl-1-aziridinepropionate; CAS number 64265-57-2) and XAMA-7 (pentaerythritol tris[3-(1-aziridinyl)propionate; CAS No. 57116-45-7) provide very efficient reaction with carboxylic acids, but these crosslinkers are unstable in water and hence have a limited shelf life in water. This is for example described in U.S. Pat. No. 5,133,997. Additionally, these polyaziridines have an unfavourable genotoxic profile.

The object of the present invention is to provide multi-aziridine crosslinkers which can be delivered and stored in water with a longer shelf life while maintaining sufficient reactivity towards carboxylic acid functional polymers.

This object has surprisingly been achieved by providing a multi-aziridine crosslinker composition, characterized in that the multi-aziridine crosslinker composition is an aqueous dispersion having a pH ranging from 8 to 14 and comprising a multi-aziridine compound in dispersed form, wherein said multi-aziridine compound has:

a. from 2 to 6 of the following structural units A:

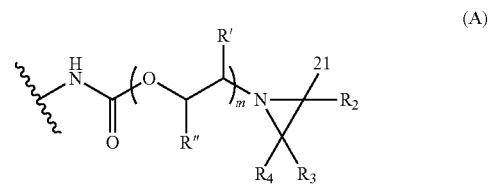

(A)

whereby
$R_1$ is H,
$R_2$ and $R_4$ are independently chosen from H or an aliphatic hydrocarbon group containing from 1 to 4 carbon atoms,
$R_3$ is an aliphatic hydrocarbon group containing from 1 to 4 carbon atoms, mist,
R' and R" are according to (1) or (2):
(1) R'=H or an aliphatic hydrocarbon group containing from 1 to 14 carbon atoms, and
R"=H, an aliphatic hydrocarbon group containing from 1 to 14 carbon atoms, a cycloaliphatic hydrocarbon group containing from 5 to 12 carbon atoms, an aromatic hydrocarbon group containing from 6 to 12 carbon atoms, $CH_2$—O—(C=O)—R''', $CH_2$—O—R'''', or $CH_2$—(OCR''''HCR''''H)$_n$—OR''''', whereby R''' is an aliphatic hydrocarbon group containing from 1 to 14 carbon atoms and R'''' is an aliphatic hydrocarbon group containing from 1 to 14 carbon atoms or an aromatic hydrocarbon group containing from 6 to 12 carbon atoms, n being from 1 to 35, R''' independently being H or an aliphatic hydrocarbon group containing from 1 to 14 carbon atoms and R''''' being an aliphatic hydrocarbon group containing from 1 to 4 carbon atoms,
(2) R' and R" form together a saturated cycloaliphatic hydrocarbon group containing from 5 to 8 carbon atoms;
b. one or more linking chains wherein each one of these linking chains links two of the structural units A; and
c. a molecular weight in the range from 500 to 10000 Daltons.

It has surprisingly been found that the aqueous crosslinker composition of the present invention has prolonged storage-stability, while at the same time still having good crosslinking efficiency towards carboxylic acid functional polymers, in particular in aqueous carboxylic acid functional polymer dispersions. The compositions according to the invention shows efficient reaction with carboxylic acid groups at room temperature. The compositions of the invention are also easy to use, its aqueous nature yielding good compatibility with waterborne binders and hence good mixing and low fouling during formulation. Further, these compositions generally have low viscosities, resulting in facile handling and accurate dosing. The prolonged storage-stability in water, combined with a more favorable hazard profile, allows coatings manufacturers and applicators to easily and safely store and use the crosslinker composition in two-component 2K coating systems, where the binder and crosslinker are mixed shortly before application.

U.S. Pat. No. 3,523,750 describes a process for modifying proteinaceous substrates such as wool with a multi-aziridine compound. U.S. Pat. No. 5,258,481 describes multifunctional water-dispersible crosslink agents which is an oligomeric material containing carbodiimide functionalities and reactive functional groups which are different from said carbodiimide functional group. U.S. Pat. No. 5,241,001 discloses multi-aziridine compounds obtained by the reaction of 1-(2-hydroxyethyl)-ethyleneimine with a polyisocyanate.

For all upper and/or lower boundaries of any range given herein, the boundary value is included in the range given, unless specifically indicated otherwise. Thus, when saying from x to y, means including x and y and also all intermediate values.

The term "coating composition" encompasses, in the present description, paint, coating, varnish, adhesive and ink compositions, without this list being limiting. The term "aliphatic hydrocarbon group" refers to optionally branched alkyl, alkenyl and alkynyl group. The term "cycloaliphatic hydrocarbon group" refers to cycloalkyl and cycloalkenyl group optionally substituted with at least one aliphatic hydrocarbon group. The term "aromatic hydrocarbon group" refers to a benzene ring optionally substituted with at least one aliphatic hydrocarbon group. These optional aliphatic hydrocarbon group substituents are preferably alkyl groups.

Examples of cycloaliphatic hydrocarbon groups with 7 carbon atoms are cycloheptyl and methyl substituted cyclohexyl. An example of an aromatic hydrocarbon group with 7 carbon atoms is methyl substituted phenyl. Examples of aromatic hydrocarbon groups with 8 carbon atoms are xylyl and ethyl substituted phenyl.

An aziridinyl group has the following structural formula:

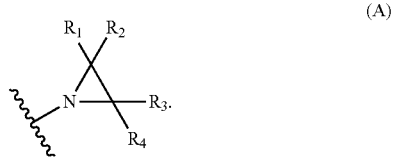

(A)

Multi-Aziridine Compound $R_1$ is H. $R_2$ and $R_4$ are independently chosen from H or an aliphatic hydrocarbon group containing from 1 to 4 carbon atoms. Preferably, $R_2$ and $R_4$ are independently chosen from H or an aliphatic hydrocarbon group containing from 1 to 2 carbon atoms.

$R_3$ is an aliphatic hydrocarbon group containing from 1 to 4 carbon atoms, preferably an aliphatic hydrocarbon group containing from 1 to 2 carbon atoms.

In a preferred embodiment of the invention, $R_2$ is H, $R_3$ is $C_2H_5$ and $R_4$ is H. In another and more preferred embodiment of the invention, $R_2$ is H, $R_3$ is $CH_3$ and $R_4$ is H or $CH_3$.

In another and even more preferred embodiment of the invention, $R_2$ is H, $R_3$ is $CH_3$ and $R_4$ is H.

Whilst the structural units A present in the multi-aziridine compound may independently have different $R_2$, $R_3$, $R_4$, R' and/or R", the structural units A present in the multi-aziridine compound are preferably identical to each other.

Preferably, R' and R" are according to (1) or (2):

(1) R'=H or an alkyl group containing from 1 to 2 carbon atoms;

R"=H, an aliphatic hydrocarbon group containing from 1 to 4 carbon atoms, a cycloaliphatic hydrocarbon group containing from 5 to 12 carbon atoms, an aromatic hydrocarbon group containing from 6 to 12 carbon atoms, $CH_2$—O—(C=O)—R'", $CH_2$—O—R"", or $CH_2$—(OCR""'HCR""'H)$_n$—OR""', whereby R'" is an alkyl group containing from 1 to 14 carbon atoms and R"" is an alkyl group containing from 1 to 14 carbon atoms, n being from 1 to 35, R""' independently being H or a methyl group and R""" being an alkyl group containing from 1 to 4 carbon atoms;

(2) R' and R" form together a saturated cycloaliphatic hydrocarbon group containing from 5 to 8 carbon atoms.

In a preferred embodiment of the invention, $R_2$ is H, $R_3$ is an aliphatic hydrocarbon group containing from 1 to 2 carbon atoms, $R_4$ is H, R' is H and R" is H, an aliphatic hydrocarbon group containing from 1 to 14 carbon atoms, a cycloaliphatic hydrocarbon group containing from 5 to 12 carbon atoms, an aromatic hydrocarbon group containing from 6 to 12 carbon atoms, $CH_2$—O—(C=O)—R'" or $CH_2$—O—R"", whereby R'" is an aliphatic hydrocarbon group containing from 1 to 14 carbon atoms, preferably R'" is an aliphatic hydrocarbon group containing from 3 to 12 carbon atoms and R"" is an aliphatic hydrocarbon group containing from 1 to 14 carbon atoms. More preferably, R' is H and R" is an alkyl group containing from 1 to 4 carbon atoms, $CH_2$—O—(C=O)—R'", $CH_2$—O—R"", whereby R'" is an alkyl group containing from 3 to 12 carbon atoms, such as for example neopentyl or neodecyl. Most preferably R'" is a branched C9 alkyl. R"" is preferably an alkyl group containing from 1 to 14 carbon atoms, more preferably from 1 to 12 carbon atoms. Non-limited examples for R"" are ethyl, butyl and 2-ethylhexyl.

The multi-aziridine compound contains from 2 to 6 of the structural units A, preferably from 2 to 4 of the structural units A, more preferably 2 or 3 structural units A.

The multi-aziridine compound comprises one or more linking chains wherein each one of these linking chains links two of the structural units A. The linking chains present in the multi-aziridine compound preferably consist of from 4 to 300 atoms, more preferably from 5 to 250, more preferably from 6 to 100 atoms and most preferably from 6 to 20 atoms. The atoms of the linking chains are preferably C and optionally N, O, S and/or P, preferably C and optionally N and/or O. The linking chains are preferably a collection of atoms covalently connected which collection of atoms consists of i) carbon atoms, ii) carbon and nitrogen atoms, or iii) carbon, oxygen and nitrogen atoms.

A linking chain is defined as the shortest chain of consecutive atoms that links two structural units A. The following drawings show examples of multi-aziridine compounds, and the linking chains between two structural units A.

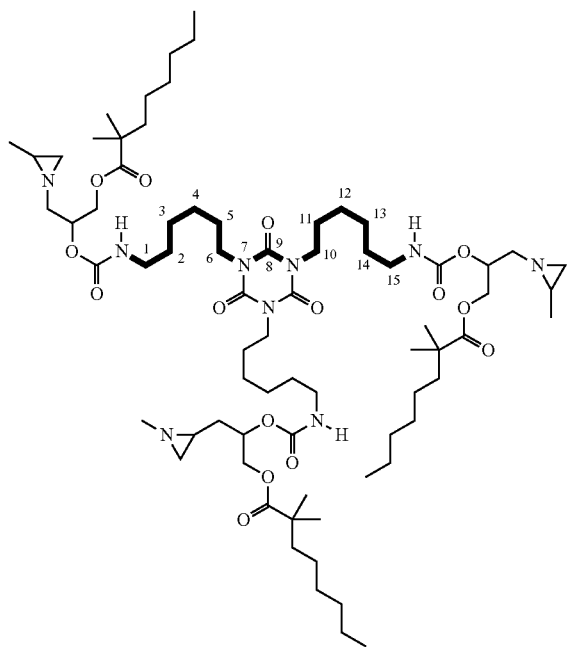

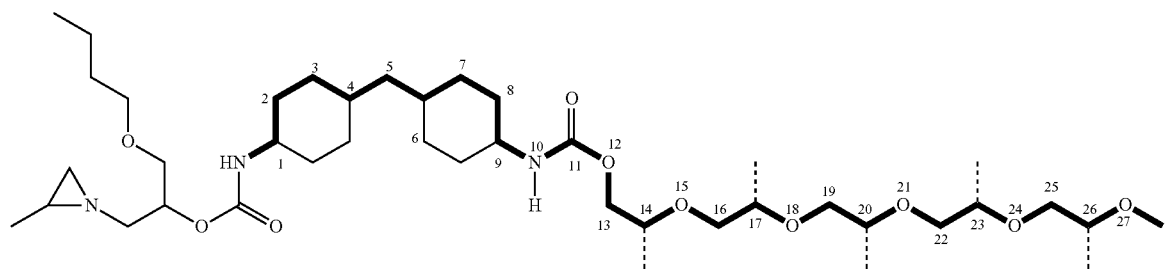

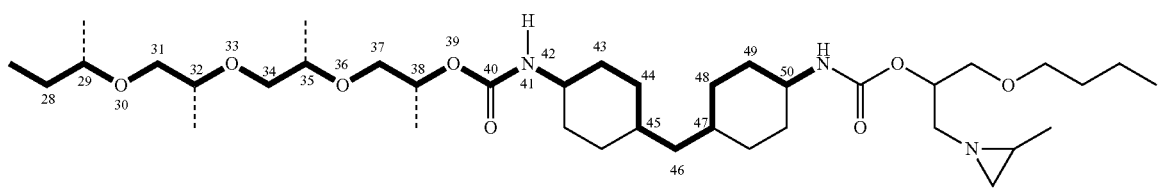

Any two of the structural units A present in the multi-aziridine compound are linked via a linking chain as defined herein. Accordingly, each structural unit A present in the multi-aziridine compound is linked to every other structural unit A via a linking chain as defined herein. In case the multi-aziridine compound has two structural units A, the multi-aziridine compound has one such linking chain linking these two structural units.

In case the multi-aziridine compound has three structural units A, the multi-aziridine compound has three linking chains, whereby each of the three linking chains is linking a structural unit A with another structural unit A, i.e. a first structural unit A is linked with a second structural unit A via a linking chain and the first and second structural units A are both independently linked with a third structural unit A via their respective linking chains.

The following drawings show for an example of a multi-aziridine compound having three structural units A, the three linking chains whereby each one of the three linking chains links two structural units A.

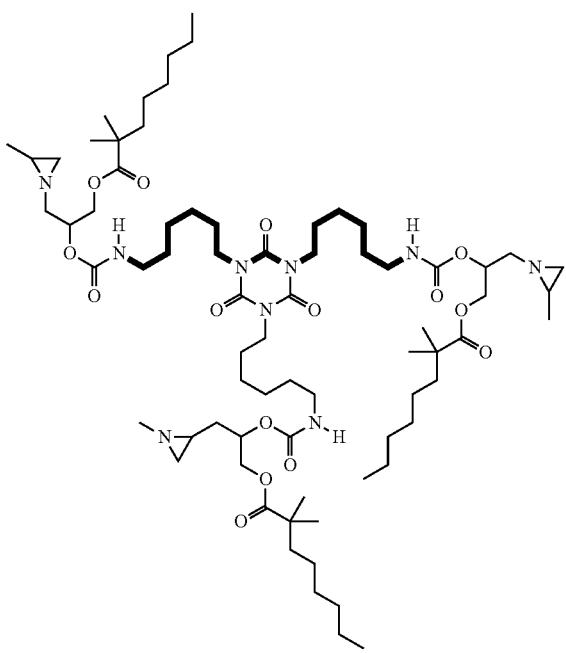
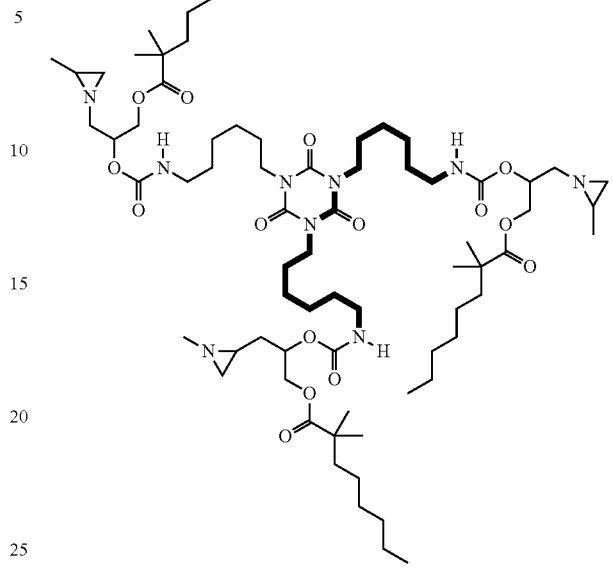
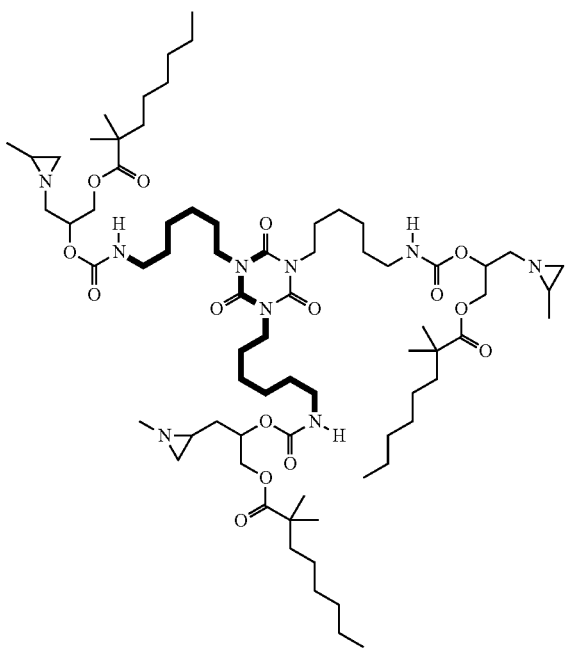

Multi-aziridine compounds with more than two structural units A have a number of linking chains according to the following equation:

LC={(AN−1)×AN)}/2, whereby LC=the number of linking chains and AN=the number of structural units A in the multi-aziridine compound. So for example if there are 5 structural units A in the multi-aziridine compound, AN=5; which means that there are {(5−1)×5}/2=10 linking chains.

The molecular weight of the multi-aziridine compound according to the invention is preferably from 600 to 5000 Daltons. The molecular weight of the multi-aziridine compound according to the invention is preferably at most 3800 Daltons, more preferably at most 3600 Daltons, more preferably at most 3000 Daltons, more preferably at most 1600 Daltons, even more preferably at most 1400 Daltons. The molecular weight of the multi-aziridine compound according to the invention is preferably at least 700 Daltons, more preferably at least 800 Daltons, even more preferably at least 840 Daltons and most preferably at least 1000 Daltons. As used herein, the molecular weight of the multi-aziridine compound is the calculated molecular weight. The calculated molecular weight is obtained by adding the atomic masses of all atoms present in the structural formula of the multi-aziridine compound. If the multi-aziridine compound is present in a composition comprising more than one multi-aziridine compound according to the invention, for example when one or more of the starting materials to prepare the multi-aziridine compound is a mixture, the molecular weight calculation can be performed for each compound individually present in the composition. The molecular weight of the multi-aziridine compound according to the invention can be measured using MALDI-TOF mass spectrometry as described in the experimental part below.

The multi-aziridine compound preferably comprises one or more connecting groups, whereby each one of these connecting groups connects two of the structural units A and whereby each one of these connecting groups consists of at least one functionality selected from the group consisting of aliphatic hydrocarbon functionality (preferably containing from 1 to 8 carbon atoms), cycloaliphatic hydrocarbon functionality (preferably containing from 4 to 10 carbon atoms), aromatic hydrocarbon functionality (preferably containing from 6 to 12 carbon atoms), isocyanurate functionality, iminooxadiazindione functionality, ether functionality, ester functionality, amide functionality, carbonate functionality, urethane functionality, urea functionality, biuret functionality, allophanate functionality, uretdione functionality and any combination thereof. More preferably, the connecting groups are an array of consecutive functionalities whereby each functionality is selected from the group consisting of aliphatic hydrocarbon functionality (preferably containing from 1 to 8 carbon atoms), cycloaliphatic hydrocarbon functionality (preferably containing from 4 to 10 carbon atoms), aromatic hydrocarbon functionality (preferably containing from 6 to 12 carbon atoms), isocyanurate functionality, iminooxadiazindione functionality, ether functionality, ester functionality, amide functionality, carbonate functionality, urethane functionality, urea functionality, biuret functionality, allophanate functionality, uretdione functionality.

The term "aliphatic hydrocarbon functionality" refers to optionally branched alkyl, alkenyl and alkynyl groups. Whilst the optional branches of C atoms are part of the connecting group, they are not part of the linking chain.

The term "cycloaliphatic hydrocarbon functionality" refers to cycloalkyl and cycloalkenyl groups optionally substituted with at least one aliphatic hydrocarbon group. Whilst the optional aliphatic hydrocarbon group substituents are part of the connecting group, they are not part of the linking chain. The optional aliphatic hydrocarbon group substituents are preferably alkyl groups.

The term "aromatic hydrocarbon functionality" refers to a benzene ring optionally substituted with at least one aliphatic hydrocarbon group. Whilst the optional aliphatic hydrocarbon group substituents are part of the connecting group, they are not part of the linking chain. The optional aliphatic hydrocarbon group substituents are preferably alkyl groups.

An isocyanurate functionality is defined as

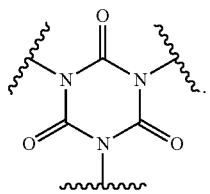 [SMILES: *n1c(=O)n(*)c(=O)n(*)c1=O]

An iminooxadiazindione functionality is defined as

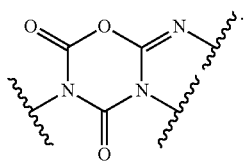 [SMILES: */N=c1/oc(=O)n(*)c(=O)n1*]

A biuret functionality is defined as

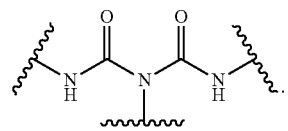 [SMILES: *NC(=O)N(*)C(=O)N*]

An allophanate functionality is defined as

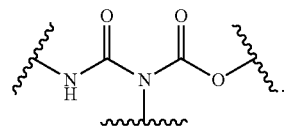 [SMILES: *NC(=O)N(*)C(=O)O*]

An uretdione functionality is defined as

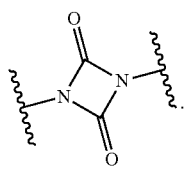 [SMILES: *N1C(=O)N(*)C1=O]

The following drawing shows in bold a connecting group for an example of a multi-aziridine compound as defined herein. In this example, the connecting group connecting two of the structural units A consists of the array of the following consecutive functionalities: aliphatic hydrocarbon functionality 1 (a linear $C_6H_{12}$), isocyanurate 2 (a cyclic $C_3N_3O_3$) functionality and aliphatic hydrocarbon functionality 3 (a linear $C_6H_{12}$).

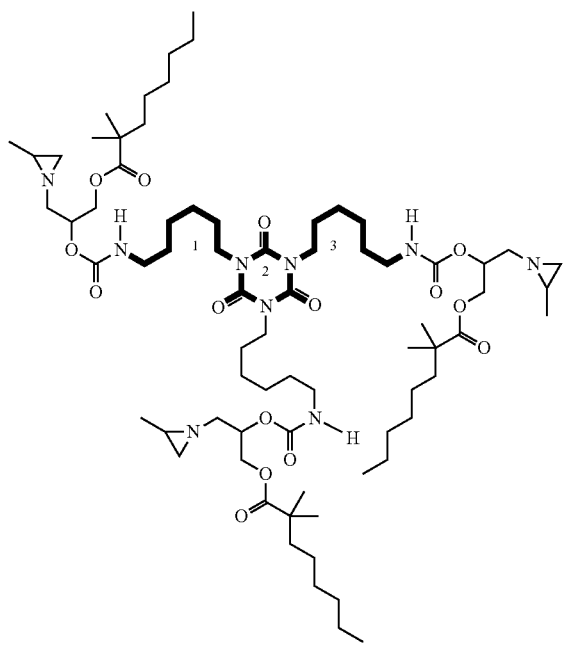

The following drawing shows in bold the connecting group for the following example of a multi-aziridine compound as defined herein. In this example, the connecting group connecting the two structural units A consists of the array of the following consecutive functionalities: aliphatic hydrocarbon functionality 1 (a linear $C_6H_{12}$), isocyanurate 2 (a cyclic $C_3N_3O_3$) and aliphatic hydrocarbon functionality 3 (a linear $C_6H_{12}$).

Any two of the structural units A present in the multi-aziridine compound as defined herein are preferably connected via a connecting group which connecting group is as defined herein. Accordingly, each structural unit A present in the multi-aziridine compound is preferably connected to every other structural unit A with a connecting group which connecting group is as defined in the invention. In case the multi-aziridine compound has two structural units A, the multi-aziridine compound has one such connecting group connecting these two structural units. In case the multi-aziridine compound has three structural units A, the multi-aziridine compound has three such connecting groups, whereby each one of the three connecting groups is connecting a structural unit A with another structural unit A.

The following drawing shows, for an example of a multi-aziridine compound having three structural units A,

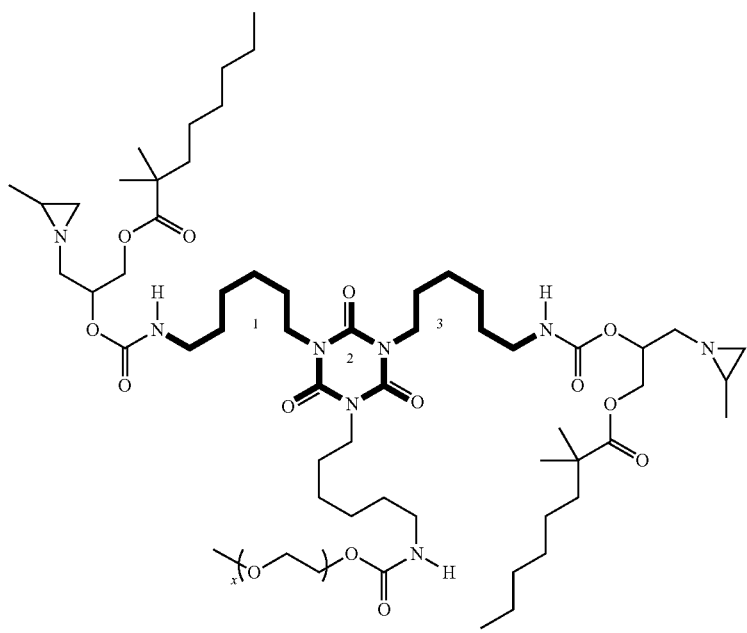

the three connecting groups whereby each one of the three connecting groups is connecting two structural units A. One connecting group consists of the array of the following consecutive functionalities: aliphatic hydrocarbon functionfollowing consecutive functionalities: aliphatic hydrocarbon functionality 3 (a linear $C_6H_{12}$), isocyanurate 2 (a cyclic $C_3N_3O_3$) and aliphatic hydrocarbon functionality 4 (a linear $C_6H_{12}$).

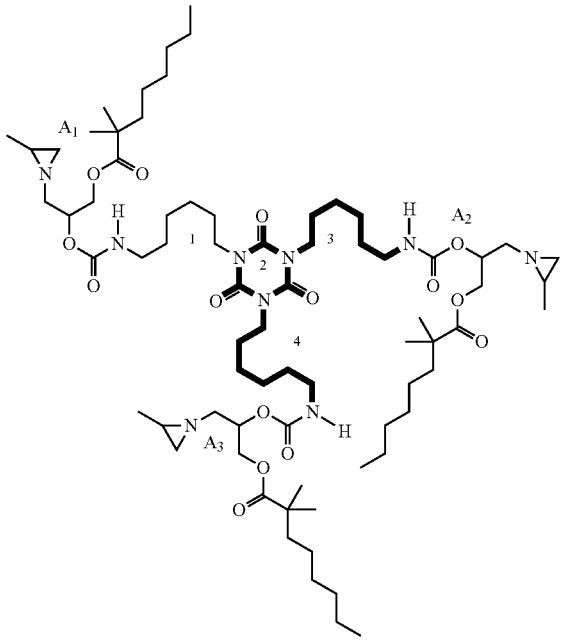

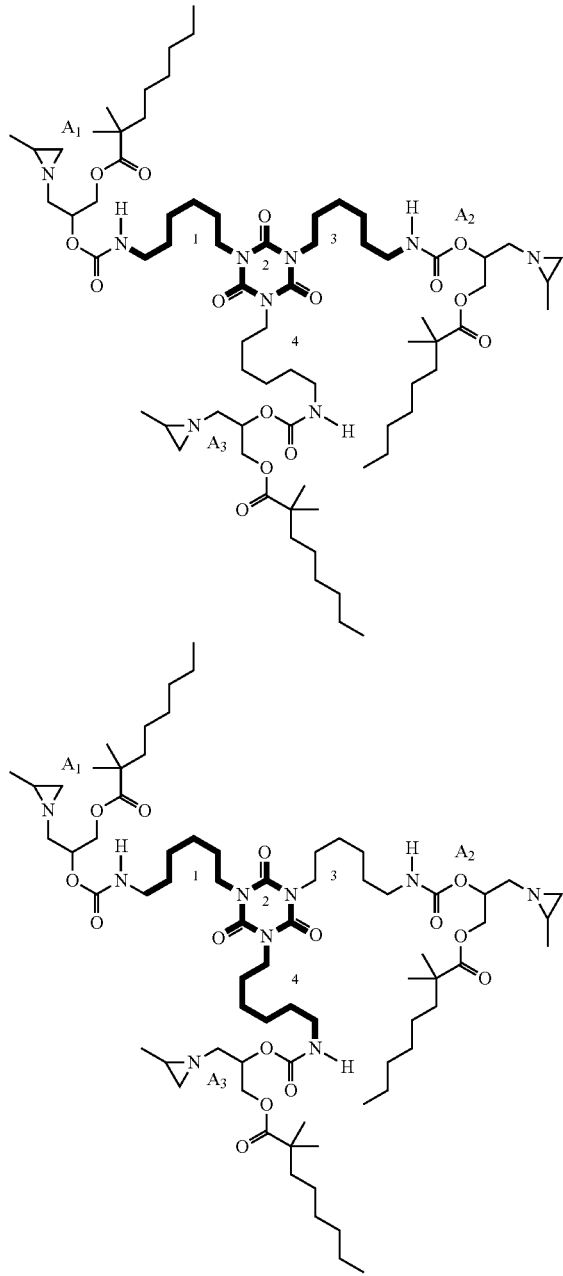

ality 1 (a linear $C_6H_{12}$), isocyanurate 2 (a cyclic $C_3N_3O_3$) and aliphatic hydrocarbon functionality 3 (a linear $C_6H_{12}$) connecting the structural units A which are labelled as A1 and A2. For the connection between structural units A which are labelled as A1 and A3, the connecting group consists of the array of the following consecutive functionalities: aliphatic hydrocarbon functionality 1 (a linear $C_6H_{12}$), isocyanurate 2 (a cyclic $C_3N_3O_3$) and aliphatic hydrocarbon functionality 4 (a linear $C_6H_{12}$), while for the connection between the structural units A which are labelled as A2 and A3, the connecting group consists of the array of the Preferably, the connecting groups consist of at least one functionality selected from the group consisting of aliphatic hydrocarbon functionality (preferably containing from 1 to 8 carbon atoms), cycloaliphatic hydrocarbon functionality (preferably containing from 4 to 10 carbon atoms), aromatic hydrocarbon functionality (preferably containing from 6 to 12 carbon atoms), isocyanurate functionality, iminooxadiazindione functionality, urethane functionality, urea functionality, biuret functionality and any combination thereof. The connecting groups preferably contain an isocyanurate functionality, an iminooxadiazindione functionality, a biuret functionality, allophanate functionality or an uretdione functionality. More preferably, the connecting groups contain an isocyanurate functionality or an iminooxadiazindione functionality. For the sake of clarity, the multi-aziridine compound may be obtained from the reaction product of one or more suitable compound B as defined herein below and a hybrid isocyanurate such as for example a HDI/IPDI isocyanurate, resulting in a multi-aziridine compound with a connecting group consisting of the array of the following consecutive functionalities: a linear $C_6H_{12}$ (i.e. an aliphatic hydrocarbon functionality with 6 carbon atoms), an isocyanurate functionality (a cyclic $C_3N_3O_3$) and

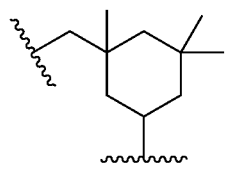 [SMILES: *CC1(C)CC(*)CC(C)(C)C1]

(i.e. a cycloaliphatic hydrocarbon functionality with 9 carbon atoms and an aliphatic hydrocarbon functionality with 1 carbon atom). Even more preferably, the connecting groups consist of the following functionalities: at least one aliphatic hydrocarbon functionality and/or at least one cycloaliphatic hydrocarbon functionality, and further an isocyanurate functionality or an iminooxadiazindione functionality.

On the connecting groups, one or more substituents may be present as pendant groups on the connection group, as shown in bold in for example the following multi-aziridine compound. These pendant groups are not part of the connecting groups.

The pendant group preferably contains

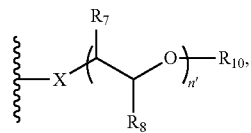

in which X, $R_7$, $R_8$, n' and $R_{10}$ are as described below. In an embodiment of the invention, the multi-aziridine compound comprises one or more connecting groups wherein each one of these connecting groups connects two of the structural units A, wherein the connecting groups consist of (i) at least two aliphatic hydrocarbon functionality or at least two cycloaliphatic hydrocarbon functionality and (ii) an isocyanurate functionality or an iminooxadiazindione functionality, and wherein a pendant group is present on a connecting group, whereby the pendant group has the following structural formula:

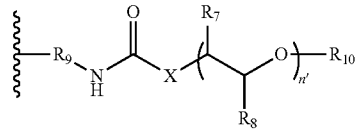

n' is the number of repeating units and is an integer from 1 to 50, preferably from 2 to 30, more preferably from 5 to 20. X is O or NH, preferably X is O,
$R_7$ and $R_8$ are independently H or $CH_3$ in each repeating unit, $R_9$ is an aliphatic hydrocarbon group, preferably containing from 1 to 8 carbon atoms, or a cycloaliphatic hydrocarbon group, preferably containing from 4 to 10 carbon atoms, and $R_{10}$ contains at most 20 carbon atoms and is an aliphatic, cycloaliphatic or aromatic hydrocarbon group or a combination thereof. In a preferred embodiment, $R_7$ and $R_8$ are H.

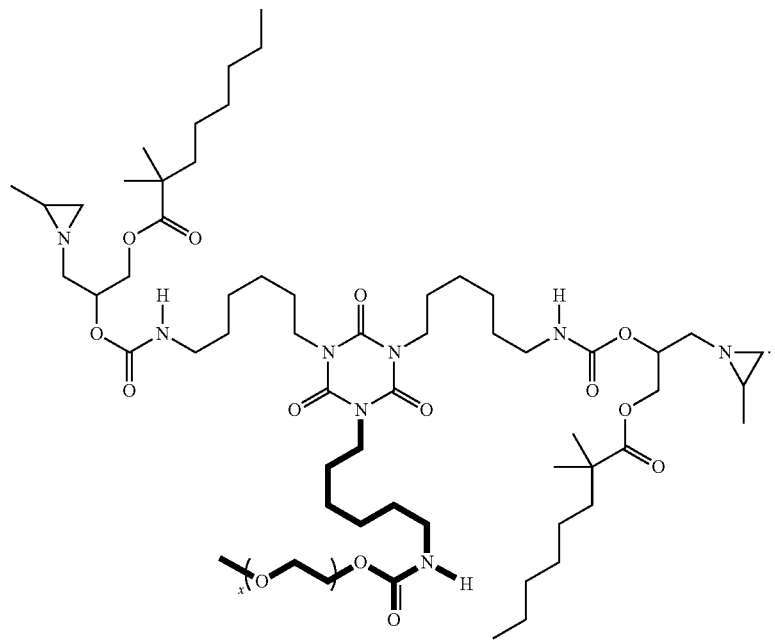

In another and more preferred embodiment, one of $R_7$ and $R_8$ is H and the other $R_7$ or $R_8$ is $CH_3$. $R_{10}$ preferably is an aliphatic hydrocarbon group containing from 1 to 20 carbon atoms (preferably $CH_3$), a cycloaliphatic hydrocarbon group containing from 5 to 20 carbon atoms or an aromatic hydrocarbon group containing from 6 to 20 carbon atoms. The presence of the pendant group results in a decreased viscosity of the multi-aziridine compound and hence easier dispersibility in the aqueous medium. In this embodiment, the multi-aziridine compound preferably contains 2 structural units A. In this embodiment the connecting group preferably consists of the array of the following consecutive functionalities: a first cycloaliphatic hydrocarbon functionality, an isocyanurate functionality or an iminooxadiazindione functionality, and a second cycloaliphatic hydrocarbon functionality, and $R_9$ is a cycloaliphatic hydrocarbon group, whereby the first and second cycloaliphatic hydrocarbon functionality and $R_9$ are identical, more preferably the connecting group consists of the array of the following consecutive functionalities: a first aliphatic hydrocarbon functionality, an isocyanurate functionality or an iminooxadiazindione functionality, and a second aliphatic hydrocarbon functionality, and $R_9$ is an aliphatic hydrocarbon group, whereby the first and second aliphatic hydrocarbon functionality and $R_9$ are identical.

In a preferred embodiment of the invention, the connecting groups present in the multi-aziridine compound as defined herein consist of the following functionalities: (i) at least one aliphatic hydrocarbon functionality and/or at least one cycloaliphatic hydrocarbon functionality and (ii) optionally at least one aromatic hydrocarbon functionality and (iii) optionally an isocyanurate functionality or iminooxadiazindione functionality or allophanate functionality or uretdione functionality. Preferably, the connecting groups present in the multi-aziridine compound of the invention consist of the following functionalities: (i) at least one aliphatic hydrocarbon functionality and/or at least one cycloaliphatic hydrocarbon functionality and (ii) optionally at least one aromatic hydrocarbon functionality and (iii) optionally an isocyanurate functionality or iminooxadiazindione functionality. A very suitable way of obtaining such multi-aziridine compound is reacting compound B with the following structural formula:

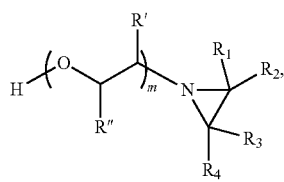

wherein $R_1$, $R_2$, $R_3$, $R_4$, R' and R" and its preferments are as defined above, with a polyisocyanate with aliphatic reactivity. The term "a polyisocyanate with aliphatic reactivity" being intended to mean compounds in which all of the isocyanate groups are directly bonded to aliphatic or cycloaliphatic hydrocarbon groups, irrespective of whether aromatic hydrocarbon groups are also present. The polyisocyanate with aliphatic reactivity can be a mixture of polyisocyanates with aliphatic reactivity. Compounds based on polyisocyanate with aliphatic reactivity have a reduced tendency of yellowing over time when compared to a similar compound but based on polyisocyanate with aromatic reactivity. The term "a polyisocyanate with aromatic reactivity" being intended to mean compounds in which all of the isocyanate groups are directly bonded to a benzene or a naphthalene group, irrespective of whether aliphatic or cycloaliphatic groups are also present. Preferred polyisocyanates with aliphatic reactivity are 1,5-pentamethylene diisocyanate PDI, 1,6-hexamethylene diisocyanate HDI, isophorone diisocyanate IPDI, 4,4'-dicyclohexyl methane diisocyanate H12MDI, 2,2,4-trimethyl hexamethylene diisocyanate, 2,4,4-trimethyl hexamethylene diisocyanate, tetramethylxylene diisocyanate TMXDI (all isomers) and higher molecular weight variants like for example their isocyanurates, allophanates or iminooxadiazindiones. In this embodiment, preferably the connecting groups consist of the array of the following consecutive functionalities: aliphatic hydrocarbon functionality, aromatic hydrocarbon functionality and aliphatic hydrocarbon functionality (for example when using TMXDI for preparing the multi-aziridine compound) or the connecting groups consist of the array of the following consecutive functionalities: cycloaliphatic hydrocarbon functionality, aliphatic hydrocarbon functionality and cycloaliphatic hydrocarbon functionality (for example when using H12MDI for preparing the multi-aziridine compound) or more preferably, the connecting groups consist of the array of the following consecutive functionalities: aliphatic hydrocarbon functionality, isocyanurate functionality or iminooxadiazindione functionality, and aliphatic hydrocarbon functionality. Most preferably, in this embodiment, the connecting group consists of the array of the following consecutive functionalities: aliphatic hydrocarbon functionality, isocyanurate functionality, and aliphatic hydrocarbon functionality (for example when using an isocyanurate of 1,6-hexamethylene diisocyanate and/or an isocyanurate of 1,5-pentamethylene diisocyanate for preparing the multi-aziridine compound).

Preferably, the number of consecutive C atoms and optionally O atoms between the N atom of the urethane group in a structural unit A and the next N atom which is either present in the linking chain or which is the N atom of the urethane group of another structural unit A is at most 9, as shown in for example the following multi-aziridine compounds having 2 resp. 3 structural units A.

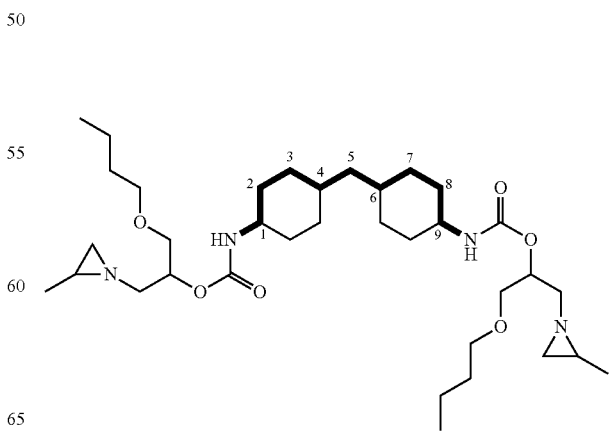

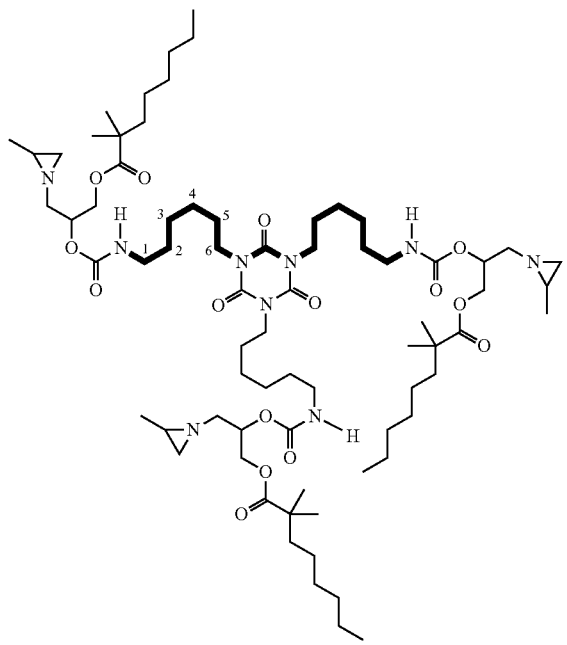

The multi-aziridine compound preferably contains at least 5 wt. %, more preferably at least 5.5. wt. %, more preferably at least 6 wt. %, more preferably at least 9 wt. %, more preferably at least 12 wt. % and preferably less than 25 wt. %, preferably less than 20 wt. % of urethane bonds. The multi-aziridine compound preferably has an aziridine equivalent weight (molecular weight of the multi-aziridine compound divided by number of aziridinyl groups present in the multi-aziridine compound) of at least 200, more preferably at least 230 and even more preferably at least 260 Daltons and preferably at most 2500, more preferably at most 1000 and even more preferably at most 500 Daltons.

The multi-aziridine compound is preferably obtained by reacting at least a polyisocyanate and a compound B as defined above with the following structural formula:

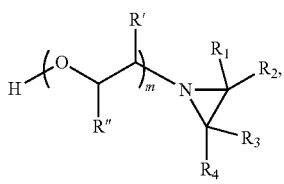

whereby the molar ratio of compound B to polyisocyanate is from 2 to 6, more preferably from 2 to 4 and most preferably from 2 to 3, and whereby m, R', R'', $R_1$, $R_2$, $R_3$ and $R_4$ are as defined above. Reacting the polyisocyanate with compound B may be carried out by bringing equivalent amounts of the polyisocyanate into contact with the compound B at a temperature in the range of from 0 to 110° C., more suitable from 20° C. to 110° C., more suitable from 40° C. to 95° C., even more suitable from 60 to 85° C. in the presence of for example a tin catalyst such as for example dibutyltin dilaureate or a bismuth catalyst such as for example bismuth neodecanoate. A solvent may be used, such as for example dimethylformamide DMF, acetone and/or methyl ethyl ketone. The polyisocyanate contains at least 2 isocyanate groups, preferably at least 2.5 isocyanate groups on average and more preferably at least 2.8 isocyanate groups on average. Mixtures of polyisocyanates may also be used as starting materials. Preferred polyisocyanates are polyisocyanates with aliphatic reactivity. The term "a polyisocyanate with aliphatic reactivity" being intended to mean compounds in which all of the isocyanate groups are directly bonded to aliphatic or cycloaliphatic hydrocarbon groups, irrespective of whether aromatic hydrocarbon groups are also present. The polyisocyanate with aliphatic reactivity can be a mixture of polyisocyanates with aliphatic reactivity. Preferred polyisocyanates with aliphatic reactivity are 1,5-pentamethylene diisocyanate PDI, 1,6-hexamethylene diisocyanate HDI, isophorone diisocyanate IPDI, 4,4'-dicyclohexyl methane diisocyanate H12MDI, 2,2,4-trimethyl hexamethylene diisocyanate, 2,4,4-trimethyl hexamethylene diisocyanate, p-tetra-methylxylene diisocyanate (p-TMXDI) and its meta isomer, and higher molecular weight variants like for example their isocyanurates or iminooxadiazindiones or allophanates or uretdiones. More preferred polyisocyanates with aliphatic reactivity are 4,4'-dicyclohexyl methane diisocyanate H12MDI, m-TMXDI, an isocyanurate or iminooxadiazindione or allophanate or uretdione of 1,6-hexamethylene diisocyanate and an isocyanurate of 1,5-pentamethylene diisocyanate. A suitable HDI containing iminooxadiazindione trimer is Desmodur® N3900, obtainable from Covestro. A suitable HDI containing allophonate is Desmodur® XP2860, obtainable from Covestro. A suitable HDI containing uretdione is Desmodur® N3400, obtainable from Covestro. Suitable HDI based isocyanurates trimers can for example be obtained from Covestro (Desmodur® N3600), Vencorex (Tolonate™ HDT LV), Asahi Kasei (Duranate™ TPA-100), Evonik (Vestanat® HT 2500/LV) and Tosoh (Coronate® HXR LV). Methods for preparing compound (B) and derivatives are known in the art. For example, synthesis of 1-(2-methyl-aziridin-1-yl)propan-2-ol is described by S. Lesniak, M. Rachwalski, S. Jarzynski, E. Obijalska *Tetrahedron Asymm.* 2013, 24 1336-1340. Synthesis of 1-(aziridin-1-yl)propan- 2-ol is described by A. Baklien, M. V. Leeding, J. Kolm *Aust. J. Chem.* 1968, 21, 1557-1570. Preferred aziridine compounds used for preparing compound B are propylene imine and ethylaziridine. Synthesis of ethylaziridine is for example described in EP0227461B1. Most preferred aziridine compounds used for preparing compound B is propylene imine.

The multi-aziridine compound can also be obtained by reacting at least a compound B with a polyisocyanate as defined above and a polyol and/or a polyamine. The multi-aziridine compound can also be obtained by reacting the polyisocyanate as defined above with a polyol and/or a polyamine and reacting the so-obtained compound with compound B. The multi-aziridine compound can also be obtained by reacting compound B with the polyisocyanate and reacting the so obtained compound with a polyol and/or a polyamine. The multi-aziridine compound can also be obtained by reacting at least a compound B with an isocyanate terminated polyurethane and/or a polyurethane urea. The (isocyanate terminated) polyurethane (urea) is obtained by reacting at least one polyol and/or polyamine with at least one polyisocyanate. Preferred polyisocyanates are as described above. The polyol is preferably selected from the group consisting of polyether polyols, polyester polyols, polythioether polyols, polycarbonate polyols, polyacetal polyols, polyvinyl polyols, polysiloxane polyols and any mixture thereof. More preferably the polyol is selected from the group consisting of polyether polyols and any mixture thereof. Preferred polyether polyols are polytetrahydrofuran, polyethylene oxide, polypropylene oxide or any mixture thereof. More preferred polyether polyol is poly(propyleneglycol). The amount of polyoxyethylene (—O—CH2-CH2)$_x$, polyoxypropylene (—O—CHCH3-CH2-)$_x$ or (—O—CH2-CH2-CH2-)$_x$ group(s) and/or polytetrahydrofurane (—O—CH2-CH2-CH2-CH2)$_x$ groups in the multi-aziridine compound is preferably at least 6 wt. %, more preferably at least 10 wt. % and preferably less than 45 wt. %, more preferably less than 40 wt. % and most preferably less than 35 wt. %, relative to the multi-aziridine compound. x represents an average addition mole number of oxyethylene, oxypropylene resp. tetrahydrofurane and x is preferably an integer from 5 to 20. An example of such a multi-aziridine compound is shown below:

polyamines are Jeffamine® D-230, Jeffamine® D-400 and Jeffamine® D-2000. The use of a polyol is preferred over the use of a polyamine.

Compound B is preferably obtained by reacting at least a non-OH functional monoepoxide compound with an aziridine compound with the following structural formula (E):

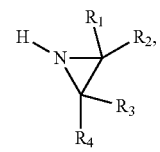

whereby $R_1$, $R_2$, $R_3$ and $R_4$ are as defined above. The non-OH functional monoepoxide may be a mixture of different non-OH functional monoepoxides. Non-limited examples of non-OH functional monoepoxide are ethylene oxide, propylene oxide, 2-ethyl oxirane, n-butylglycidylether, 2-ethylhexylglycidylether, phenyl glycidyl ether, 4-tert-butylphenyl 2,3-epoxypropyl ether (=t-butyl phenyl glycidyl ether), cresol glycidyl ether (ortho or para) and glycidyl neodecanoate. The non-OH functional monoepoxide is preferably selected from the group consisting of ethylene oxide (CAS number 75-21-8), propylene oxide (CAS number 75-56-9), 2-ethyl oxirane (CAS number 106-88-7), n-butylglycidylether (CAS number 2426-08-6), 2-ethylhexylglycidylether (CAS number 2461-15-6), glycidyl neodecanoate (CAS number 26761-45-5) and any mixture thereof. More preferably, the non-OH functional monoepoxide is selected from the group consisting of propylene oxide (CAS number 75-56-9), 2-ethyl oxirane (CAS number 106-88-7), n-butylglycidylether (CAS number 2426-08-6), 2-ethylhexylglycidylether (CAS number 2461-15-6), glycidyl neodecanoate (CAS number 26761-45-5) and any mixture thereof.

The multi-aziridine compound is preferably obtained in a process comprising at least the following steps (i) and (ii):
(i) Reacting an aziridine of formula (E) with at least a non-OH functional monoepoxide compound to obtain compound B, and
(ii) Reacting compound B with a polyisocyanate.

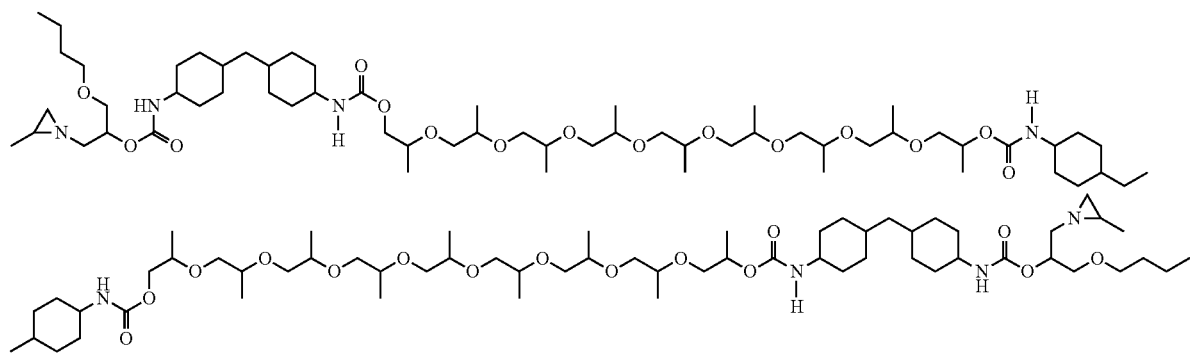

The polyamine is preferably selected from the group consisting of polyether polyamines, polyester polyamines, polythioether polyamines, polycarbonate polyamines, polyacetal polyamines, polyvinyl polyamines, polysiloxane polyamines and any mixture thereof. More preferably the polyamine is selected from the group consisting of polyether polyamines and any mixture thereof. Preferred polyether Step (i) can be carried out, for example, by bringing one equivalent of the epoxide compound into contact with one equivalent of the aziridine at a temperature in the range of from 20° C. to 110° C., more suitable from 40° C. to 95° C., even more suitable from 60 to 85° C. at atmospheric pressure. The reaction (step (ii)) of the adduct (compound B)

obtained in step (i) with the polyisocyanate can be carried out, for example, by bringing equivalent amounts of the polyisocyanate into contact with the adduct at a temperature in the range of from 20° C. to 110° C., more suitable from 40° C. to 95° C. at atmospheric pressure, in the presence of for example a tin catalyst such as for example dibutyltin dilaureate.

Examples of preferred multi-aziridine compounds present in the multi-aziridine crosslinker composition of the invention are

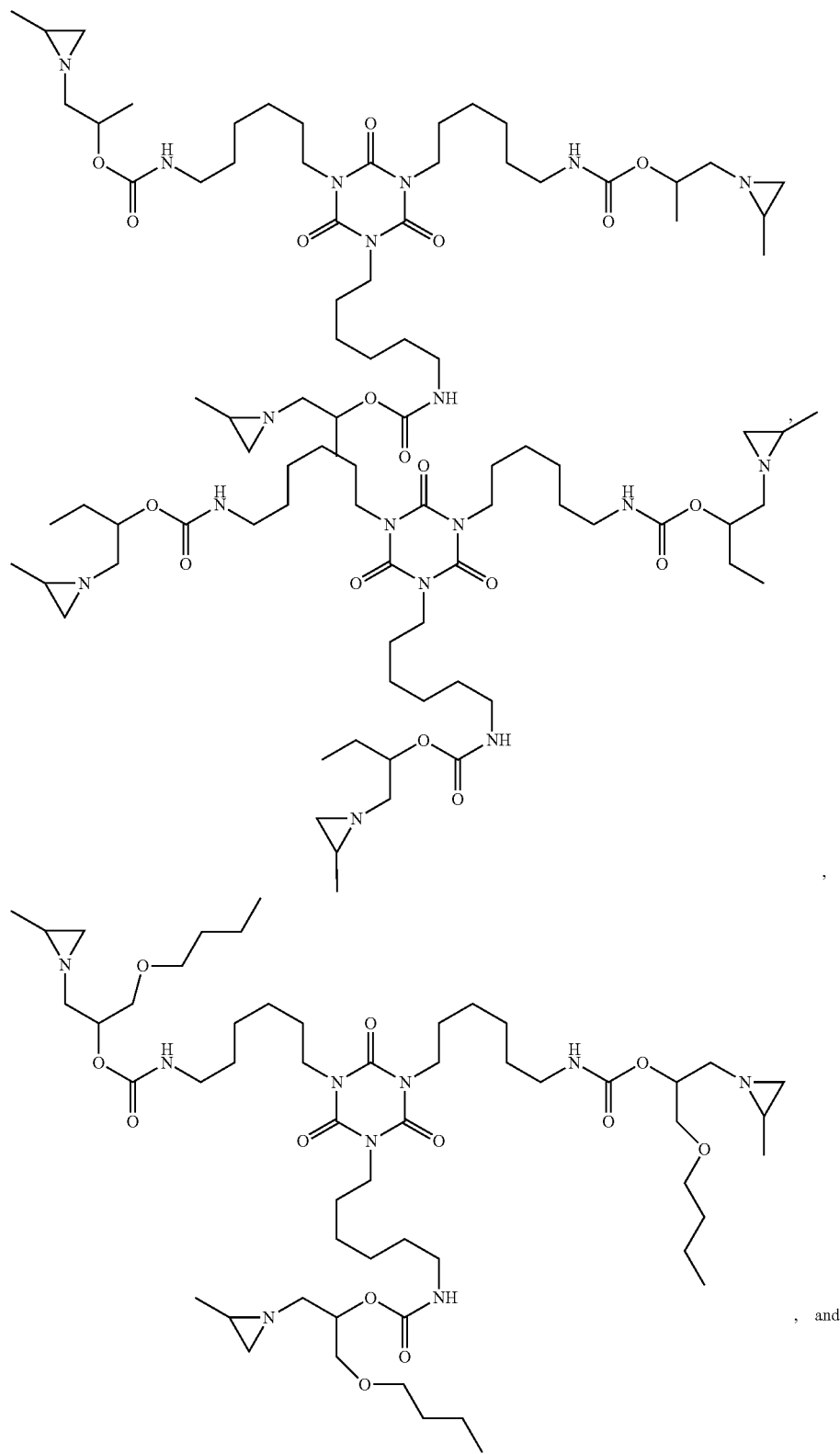

-continued

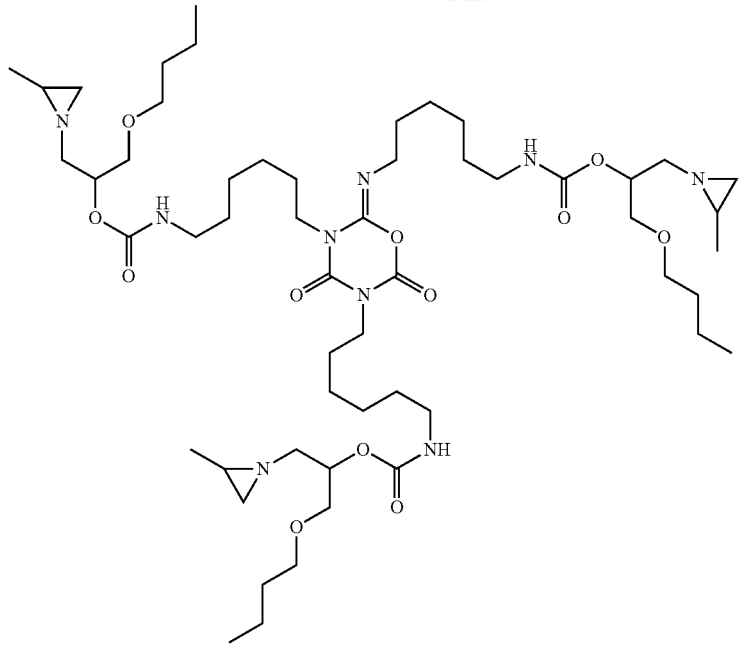 [SMILES: CCCCOCC(CN1CC1C)OC(=O)NCCCCCC/N=c1\oc(=O)n(CCCCCCNC(=O)OC(COCCCC)CN2CC2C)c(=O)n1CCCCCCNC(=O)OC(COCCCC)CN1CC1C]

In a preferred embodiment of the invention, the multi-aziridine compound present in dispersed form in the aqueous dispersion of the invention has
a. from 2 to 6 the structural units according to structural formula A

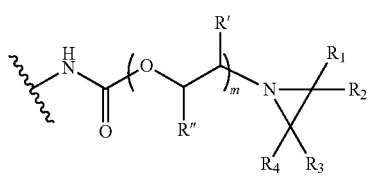

(A)

whereby $R_1$, $R_2$, $R_3$, $R_4$, $R_5$, R' and R" and its preferments are as defined above,
b. one or more linking chains wherein each one of these linking chains links two of the structural units A, whereby the one or more linking chains are preferably as defined above, and
c. a molecular weight from 600 to 5000 Daltons, preferably a molecular weight of at least 700 Daltons, more preferably at least 800 Daltons, even more preferably at least 840 Daltons and most preferably at least 1000 Daltons and preferably a molecular weight of at most 3800 Daltons, more preferably at most 3600 Daltons, more preferably at most 3000 Daltons, more preferably at most 1600 Daltons, even more preferably at most 1400 Daltons.

It has surprisingly been found that such multi-aziridine compounds have reduced genotoxicity compared to the very often used trimethylolpropane tris(2-methyl-1-aziridinepropionate). The multi-aziridine compounds show either only weakly positive induced genotoxicity or even they do not show genotoxicity, i.e. they show a genotoxicity level comparable with the naturally occurring background. Accordingly, the multi-aziridine compounds with reduced genotoxicity compared to trimethylolpropane tris(2-methyl-1-aziridinepropionate) have a more favourable hazard profile than trimethylolpropane tris(2-methyl-1-aziridinepropionate) greatly reducing safety, health and environmental risks associated with their use, resulting in reduction or even removal of the operational and administrative burden of handling of the multi-aziridine compounds with reduced genotoxicity. The multi-aziridine compound preferably comprises one or more connecting groups whereby each one of the connecting groups connects two of the structural units A and whereby the connecting groups and its preferments are as defined above, In this embodiment, the amount of aziridinyl group functional molecules (also referred to as aziridine functional molecules), present in the multi-aziridine crosslinker composition according to the invention, having a molecular weight lower than 250 Daltons, more preferably lower than 350 Daltons, even more preferably lower than 450 Daltons, even more preferably lower than 550 Daltons and even more preferably lower than 580 Daltons is preferably lower than 5 wt. %, more preferably lower than 4 wt. %, more preferably lower than 3 wt. %, more preferably lower than 2 wt. %, more preferably lower than 1 wt. %, more preferably lower than 0.5 wt. %, more preferably lower than 0.1 wt. % and most preferably 0 wt. %, relative to the total weight of the multi-aziridine crosslinker composition, whereby the molecular weight is determined using LC-MS as described in the experimental part below. Such aziridinyl group functional molecules may be obtained as side-products during preparation of the multi-aziridine compound as defined herein.

The average number of aziridinyl groups per aziridinyl-containing molecule in the composition is preferably at least 1.8, more preferably at least 2, more preferably at least 2.2 and preferably less than 10, more preferably less than 6 and most preferably less than 4. Most preferably, the average number of aziridinyl groups per aziridinyl-containing molecule in the composition is from 2.2 to 3.

pH of the Aqueous Dispersion

The pH of the aqueous dispersion is at least 8. For further prolonging the shelf-life of the aqueous dispersion of the invention, it is beneficial that the pH is at least 8.5, preferably at least 9, more preferably at least 9.5. The pH of the aqueous dispersion is at most 14, preferably at most 13, more preferably at most 12 and even more preferably at most 11.5, since this allows to lower the amount of base present in the aqueous dispersion of the invention while the shelf-life of the aqueous dispersion remains sufficiently long. Most preferably, the pH of the aqueous dispersion is in the range from 9.5 to 11.5.

The aqueous dispersion preferably comprises ammonia, a secondary amine, a tertiary amine, LiOH, NaOH and/or KOH to adjust the pH to the desired value. Preferred amines are ammonia, secundairy amines and/or tertiary amines. Examples of such secundairy amines are, but not limited to, diisopropylamine, di-sec-butylamine and di-t-butylamine. More preferred amines are tertiary amines. Examples of such tertiary amines are, but not limited to, n-ethylmorpholine, n-methyl piperidine, n,n-dimethyl butyl amine, dimethyl isopropyl amine, dimethyl n-propyl amine, dimethyl ethylamine, triethylamine, dimethyl benzyl amine, n,n-dimethyl ethanolamine, 2-(diethylamino)ethanol, n,n-dimethyl isopropanol amine, 1-dimethylamino-2-propanol, 3-dimethylamino-1-propanol, 2-(dimethylamino)ethanol, 2-[2-(dimethylamino)ethoxy] ethanol. Preferred tertiary amines are n-ethylmorpholine, n-methyl piperidine, n,n-dimethyl butyl amine, dimethyl isopropyl amine, dimethyl n-propyl amine, dimethyl ethylamine, triethylamine and/or dimethyl benzyl amine. Most preferred is triethylamine.

The amount of water in the aqueous dispersion is preferably at least 15 wt. %, more preferably at least 20 wt. %, more preferably at least 30 wt. %, even more preferably at least 40 wt. %, on the total weight of the aqueous dispersion. The amount of water in the aqueous dispersion is preferably at most 95 wt. %, more preferably at most 90 wt. %, more preferably at most 85 wt. %, more preferably at most 80 wt. %, even more preferably at most 70 wt. %, even more preferably at most 60 wt. %, on the total weight of the aqueous dispersion.

The multi-aziridine compound as defined herein is present in the aqueous dispersion in an amount of preferably at least 5 wt. %, more preferably at least 10 wt. %, more preferably at least 15 wt. %, more preferably at least 20 wt. %, even more preferably at least 25 wt. %, even more preferably at least 30 wt. %, even more preferably at least 35 wt. %, on the total weight of the aqueous dispersion. The multi-aziridine compound as defined herein is present in the aqueous dispersion in an amount of preferably at most 70 wt. %, preferably at most 65 wt. %, more preferably at most 60 wt. %, even more preferably at most 55 wt. %, on the total weight of the aqueous dispersion.

Preferably at least 50 wt. %, more preferably at least 80 wt. %, more preferably at least 95 wt. %, even more preferably at least 99 wt. % of the multi-aziridine compound as defined herein is present in the multi-aziridine crosslinker composition in dispersed form. Accordingly, the multi-aziridine crosslinker composition of the invention comprises particles comprising multi-aziridine compound as defined herein. Said particles preferably have a scatter intensity based average hydrodynamic diameter from 30 to 650 nanometer, more preferably from 50 to 500 nm, even more preferably from 70 to 350 nm, even more preferably from 120 to 275 nm. The scatter intensity based average hydrodynamic diameter of said particles may be controlled via a number of ways. For example, the scatter intensity based average hydrodynamic diameter of said particles may be controlled during the preparation of an aqueous dispersion of the invention by using different types of dispersants, and/or different amounts of dispersant(s), and/or by applying different shear stress, and/or by applying different temperature. For example, the scatter intensity based average hydrodynamic diameter of the particles is inversely dependent to the amount of the dispersant used in the preparation of an aqueous dispersion of the invention; for example, the scatter intensity based average hydrodynamic diameter of the particles decreases by increasing the amount of a dispersant. For example, the scatter intensity based average hydrodynamic diameter of the particles is inversely dependent to the shear stress applied during the preparation of an aqueous dispersion of the invention; for example, the scatter intensity based average hydrodynamic diameter of the particles decreases by increasing the shear stress. Exemplary dispersants include but are not limited to ATLAS™ G-5000, ATLAS™ G-5002L-LQ, Maxemul™ 7101 supplied by Croda.

The solids content of the aqueous dispersion is preferably at least 5, more preferably at least 10, even more preferably at least 20, even more preferably at least 30, even more preferably at least 35 wt. %. The solids content of the aqueous dispersion is preferably at most 70, preferably at most 65 and more preferably at most 55 wt. %. The solids content of the aqueous dispersion is most preferably in the range of from 35 to 55 wt. %.

The multi-aziridine compound as defined above is usually obtained in a composition in which, next to the multi-aziridine compound, remaining starting materials, side-products and/or solvent used in the preparation of the multi-aziridine compounds may be present. The composition may contain only one multi-aziridine compound as defined above but may also contain more than one multi-aziridine compound as defined above. Mixtures of multi-aziridine compounds are for example obtained when a mixture of polyisocyanates as starting material are used. The aqueous dispersion of the invention can be obtained by dispersing the multi-aziridine compound into water and adjusting the pH of the aqueous dispersion to the desired value or by dispersing the multi-aziridine compound into a mixture of water and at least one base which mixture has a pH such as to obtain an aqueous dispersion with the desired pH value or by adding a mixture of water and base to the multi-aziridine compound. Dispersing of the multi-aziridine in water or into a mixture of water and at least one base can be done using techniques well-known in the art. Solvents and/or high shear can be utilized in order to assist in the dispersion of the multi-aziridine compound.

The aqueous dispersion may further comprise organic solvent in an amount of at most 35 wt. %, preferably at most 30, for example at most 25, for example at most 20, for example at most 12, for example at most 10, for example at most 8, for example at most 5, for example at most 4, for example at most 3, for example at most 2, for example at most 1, for example at most 0.5, for example at most 0.2, for example at most 0.1 wt % on the total weight of the aqueous dispersion. Organic solvent may optionally be added before, during and/or after synthesis of the multi-aziridine(s). Organic solvent can be utilized in order to assist in dispersing the multi-aziridine compound in water. If desired, organic solvent can be removed afterwards from the multi-aziridine crosslinker composition by reduced pressure and/or increased temperatures. Typical organic solvents are glycols, ethers, alcohols, cyclic carbonates, pyrrolidones, dimethylformamide, dimethylsulfoxide, n-formylmorpholine, dimethylacetamide, and ketones. Preferred solvents are glycols, ethers, alcohols, cyclic carbonates and ketones.

Preferably the dispersing of the multi-aziridine compound is done in the presence of a dispersant. Accordingly, the aqueous dispersion of the invention preferably comprises a dispersant. In the context of the present invention, a dispersant is a substance that promotes the formation and colloidal stabilisation of a dispersion. In the present invention, said dispersant is preferably a species that is non-covalently attached to the multi-aziridine compound and/or said dispersant is a separate molecule component that is surface-active. Examples of species non-covalently attached to the multi-aziridine compound are urethane and/or urea containing amphiphilic compounds such as HEUR thickeners.

More preferably, said dispersant is at least one separate molecule component that is surface-active. Preferred separate surface-active molecule components are:
  (i) multi-aziridine compounds as defined above containing functional groups such as sulphonate, sulphate, phosphate and/or phosphonate functional groups, preferably sulphonate and/or phosphonate groups, more preferably sulphonate groups, and/or
  (ii) a polymer preferably having a number average molecular weight as measured with MALDI-ToF-MS as described below of at least 2000 Daltons, more preferably at least 2500 Daltons, more preferably at least 3000 Daltons, more preferably at least 3500 Daltons, more preferably at least 4000 Daltons, and preferably at most 1000000 Daltons, more preferably at most 100000, at most 10000 Daltons.

More preferred separate surface-active molecule components are polymers having a number average molecular weight as measured with MALDI-ToF-MS as described below of at least 2000 Daltons, more preferably at least 2500 Daltons, more preferably at least 3000 Daltons, more preferably at least 3500 Daltons, more preferably at least 4000 Daltons, and preferably at most 1000000 Daltons, more preferably at most 100000, even more preferably at most 10000 Daltons. Preferred polymers are polyethers, more preferably polyether copolymers, even more preferably polyether block copolymers, even more preferably poly(alkylene oxide) block copolymers, even more preferably poly(ethylene oxide)-co-poly(propylene oxide) block copolymers. Non-limited examples of preferred separate surface-active molecule dispersants are Atlas™ G-5000 obtainable from Croda, Maxemul™ 7101 from Croda and/or Pluronic® P84 from BASF. The amount of separate surface-active molecule component is generally in the range of from 0.1 to 20 wt. %, preferably at least 0.5, more preferably at least 1, even more preferably at least 2, even more preferably at least 3 wt. %, based on the total weight of the aqueous dispersion.

Multi-aziridine compounds as defined under (i) containing functional groups such as sulphonate, sulphate, phosphate and/or phosphonate functional groups, preferably containing sulphonate functional groups, are preferably obtained by reacting part of the isocyanate groups of the polyisocyanates used to prepare the multi-aziridine compound with a hydroxy or amine functional ionic building block (preferably neutralized with an inorganic base). Examples of hydroxy or amine functional ionic building blocks include 2-(cyclohexylamino)ethanesulfonic acid, 3-cyclohexyl-amino)propanesulfonic acid, methyltaurine, taurine, Tegomer® DS-3404. Preferably sulfonic acid salts are used as hydroxy or amine functional ionic building block.

Crosslinking efficiency of a crosslinker can be assessed by assessing the chemical resistance defined and determined as described below.

Storage stability of an aqueous dispersion according to the invention can be assessed by storing the aqueous dispersion in particular at increased temperature, e.g. 50° C., and assessing the change of viscosity, defined and determined as described below, of the stored aqueous dispersion and/or assessing the change of the chemical resistance, defined and determined as described below, in particular the ethanol resistance, of the stored aqueous dispersion.

The aqueous dispersion of the present invention preferably has a storage stability of at least 2 weeks, more preferably at least 3 weeks and even more preferably at least 4 weeks at 50° C. Storage stable for at least x week(s) at 50° C. means that after the dispersion has been stored for x week at 50° C. (i) the end viscosity of the aqueous dispersion is at most 50 times higher than the starting viscosity, preferably at most 45 times higher than the starting viscosity, more preferably at most 40 times higher than the starting viscosity, more preferably at most 35 times higher than the starting viscosity, more preferably at most 30 times higher than the starting viscosity, more preferably at most 25 times higher than the starting viscosity, more preferably at most 20 times higher than the starting viscosity, more preferably at most 15 times higher than the starting viscosity, more preferably at most 10 times higher than the starting viscosity and most preferably at most 5 times higher than the starting viscosity and/or (ii) the chemical resistance, defined and determined as described below, of the aqueous dispersion decreases with at most 3 points, preferably with at most 2 points, and even more preferably with at most 1 point. Preferably, storage stable for at least x week(s) at 50° C. means that after the dispersion has been stored for x week at 50° C. (i) the end viscosity of the aqueous dispersion is at most 50 times higher than the starting viscosity, preferably at most 45 times higher than the starting viscosity, more preferably at most 40 times higher than the starting viscosity, more preferably at most 35 times higher than the starting viscosity, more preferably at most 30 times higher than the starting viscosity, more preferably at most 25 times higher than the starting viscosity, more preferably at most 20 times higher than the starting viscosity, more preferably at most 15 times higher than the starting viscosity, more preferably at most 10 times higher than the starting viscosity and most preferably at most 5 times higher than the starting viscosity and (ii) the chemical resistance, defined and determined as described below, of the aqueous dispersion decreases with at most 3 points, preferably with at most 2 points, and even more preferably with at most 1 point. By 'starting viscosity' of an aqueous dispersion is meant the viscosity (defined and determined as described below) of the aqueous dispersion determined upon its preparation and just before the aqueous dispersion is stored at 50° C. By 'end viscosity' of an aqueous dispersion is meant the viscosity (defined and determined as described below) of the aqueous dispersion determined after the aqueous dispersion was stored for x weeks at 50° C.

The present invention further relates to a process for preparing the multi-aziridine crosslinker composition according to the invention, wherein the process comprises dispersing the multi-aziridine compound as defined herein into water to obtain an aqueous dispersion and adjusting the pH of the aqueous dispersion to the desired value or preferably wherein the process comprises dispersing the multi-aziridine compound as defined herein into a mixture of water and at least one base which mixture has a pH such as to obtain an aqueous dispersion with the desired pH value.

In a preferred embodiment of the invention, the dispersant is a separate surface-active polymer having a number average molecular weight of at least 2000 Daltons (ii). In this preferred embodiment, the process for preparing the multi-aziridine crosslinker composition according to the invention preferably comprises A) optionally but preferably mixing the multi-aziridine compound as defined above in an organic solvent,
B) mixing the multi-aziridine compound as defined above or the solution obtained in step A) with a dispersant as described above to obtain a composition comprising the multi-aziridine compound and dispersant,
C) mixing water and base or mixing basic aqueous medium into said composition comprising the multi-aziridine compound and dispersant, to obtain a dispersion
D) optionally, but preferably, evaporating organic solvent from said dispersion to obtain a further dispersion, and optionally mixing additional water or basic aqueous medium into said further dispersion, to obtain the aqueous dispersion of the present invention.

Step C) is preferably effected using a high-shear dispersion equipment

The present invention further relates to the use of the multi-aziridine crosslinker composition according to the invention for crosslinking a carboxylic acid functional polymer dissolved and/or dispersed, preferably dispersed, in water whereby the amounts of aziridinyl groups and of carboxylic acid groups are chosen such that the stoichiometric amount (SA) of aziridinyl groups on carboxylic acid groups is from 0.1 to 2.0, more preferably from 0.2 to 1.5, even more preferably from 0.25 to 0.95, most preferably from 0.3 to 0.8. The carboxylic acid functional polymer contains carboxylic acid groups and/or carboxylate groups which are preferably free of a covalent bond that blocks these groups to chemically react with the aziridine moiety present in the multi-aziridine compound. As used herein, the amount of carboxylic acid groups present in the carboxylic acid functional polymer is the summed amount of deprotonated and protonated carboxylic acid groups present in the polymer to be crosslinked, i.e. in the carboxylic acid functional polymer. Thus, the amount of carboxylic acid groups present in the carboxylic acid functional polymer is the summed amount of carboxylate groups and carboxylic acid groups present in the carboxylic acid functional polymer. The polymer to be crosslinked preferably comprises carboxylate groups which are at least partially neutralized with base. Preferably at least part of the base is a volatile base. Preferably, at least a part of the carboxylic acid groups present in the carboxylic acid functional polymer to be crosslinked are subjected to deprotonation to obtain carboxylate groups. The deprotonation is effected by neutralizing the carboxylic acid functional polymer with a base. Examples of suitable bases are ammonia, secondary amines, tertiary amines, LiOH, NaOH and/or KOH. Examples of secondary amines and tertiary amines are described above. Preferred bases are tertiary amines. Preferred tertiary amines are as described above. Most preferred is triethylamine.

In order to avoid undesirable premature crosslinking reaction between the crosslinking agent and the polymer to be crosslinked during the storage of the multi-aziridine crosslinker composition, the skilled person knows that the multi-aziridine crosslinking composition is preferably not to be mixed with the polymer to be crosslinked during the storage of the multi-aziridine crosslinker composition; the reason being the crosslinking reaction between the crosslinking agent and the polymer to be crosslinked may start immediately after mixing the crosslinking agent and the polymer to be crosslinked. Therefore, it is preferred that the multi-aziridine crosslinker composition of the invention does not contain the polymer(s) to be crosslinked. The present invention therefore further also relates to a two-component coating system comprising a first component and a second component each of which is separate and distinct from each other and wherein the first component comprises a carboxylic acid functional polymer dissolved and/or dispersed, preferably dispersed, in an aqueous medium and the second component comprises the multi-aziridine crosslinker composition of the present invention, whereby the first and second component are separately stored, since the crosslinking reaction between the crosslinking agent and the polymer to be crosslinked may start immediately after mixing the crosslinking agent with the aqueous composition of polymer to be crosslinked. As used herein, a coating composition refers to the composition comprising the polymer(s) which is (are) to be crosslinked which polymer(s) is dissolved and/or dispersed, preferably dispersed, in water and further comprising the multi-aziridine crosslinker composition of the present invention.

The present invention further also relates to a coating composition obtained by mixing the first and second component of the two-component system just prior to application of the coating composition, whereby the coating composition comprises aziridinyl groups Q and carboxylic acid groups in an amount such that the stoichiometric amount (SA) of aziridinyl groups Q on carboxylic acid groups is preferably from 0.1 to 2.0, more preferably from 0.2 to 1.5, even more preferably from 0.25 to 0.95, most preferably from 0.3 to 0.8.

The present invention further relates to a substrate having a coating obtained by (i) applying a coating composition as described above to a substrate and (ii) drying the coating composition by evaporation of volatiles. The drying of the coating composition is preferably effected at a temperature lower than 160° C., preferably at a temperature lower than 90° C., more preferably at a temperature lower than 50° C. and most preferably at ambient temperature. The coating composition according to the invention can be applied to any kind of substrate, such as for example wood, leather, concrete, textile, plastic, vinyl floors, glass, metal, ceramics, paper, wood plastic composite, glass fiber reinforced materials. The thickness of the dry coating on the substrate is preferably from 1 to 200 micron, more preferably from 5 to 150 micron and most preferably from 15 to 90 microns. In case the coating composition is an ink composition, the thickness of the dry ink is preferably from 0.005 to 35 micron, more preferably from 0.05 to 25 micron and most preferably from 4 to 15 microns.

Non-limited examples of crosslinkable carboxylic acid functional polymers are vinyl polymers like styrene-acrylics, (meth)acrylic copolymers, vinyl acetate (co)polymers such as for example vinyl acetate vinyl chloride ethylene polymers, polyurethanes, polycondensates like polyesters, polyamides, polycarbonates and hybrids of any of these polymers where at least one of the two polymers have a carboxylic acid functionality.

The carboxylic acid functional polymer is preferably selected from the group consisting of polyesters, polycarbonates, polyamides, vinyl polymers, polyacrylates, polymethacrylates, poly(acrylate-co-methacrylate)s, polyurethanes, poly(urethane-co-acrylate)s, poly(urethane-co-methacrylate)s, poly(urethane-co-acrylate-co-methacrylate), polyureas, and mixtures thereof. In an embodiment of the invention, preferred crosslinkable carboxylic acid functional polymers are selected from the group consisting of vinyl polymers, polyacrylates, polymethacrylates, poly (acrylate-co-methacrylate)s and mixtures thereof. Preferably by vinyl polymer is meant a polymer comprising reacted residues of styrene and acrylates and/or methacrylates. In another embodiment, the carboxylic acid functional polymer is selected from the group consisting of polyurethanes, poly(urethane-co-acrylate)s, poly(urethane-co-methacrylate)s, poly(urethane-co-acrylate-co-methacrylate), polyureas, and mixtures thereof The acid value of the carboxylic acid functional polymer is preferably from 2 to 135 mg KOH/gram of the carboxylic acid functional polymer, more preferably from 3 to 70 mg KOH/g carboxylic acid functional polymer, even more preferably from 10 to 50 mg KOH/g carboxylic acid functional polymer and even more preferably from 15 to 50 mg KOH/g carboxylic acid functional polymer. In case high crosslink density is required, the acid value of the carboxylic acid functional polymer is preferably from 50 to 200 mg KOH/g carboxylic acid functional polymer. As used herein, the acid value of the carboxylic acid functional polymer(s) is calculated according to the formula AV=((total molar amount of carboxylic acid components included in the carboxylic acid functional polymer(s) per gram of total amount of components included in the carboxylic acid functional polymer(s)) *56.1*1000) and is denoted as mg KOH/gram carboxylic acid functional polymer(s). The acid value of the carboxylic acid functional polymer(s) can thus be controlled by the molar amount of carboxylic acid components that is used to prepare the carboxylic acid functional polymer(s). In case the acid value cannot be properly calculated, the acid value is determined by ASTM D1639-90(1996)e1.

The ratio of number-average molecular weight $M_n$ of the carboxylic acid functional polymer to acid value of the carboxylic acid functional polymer is preferably at least 150, more preferably at least 300, even more preferably at least 600, even more preferably at least 1000, even more preferably at least 5000 and most preferably at least 15000. As used herein, the number-average molecular weight $M_n$ of the carboxylic acid functional polymer is determined by Size Exclusion Chromatography with NMP-MEK.

The invention is further defined by the set of exemplary embodiments as listed hereafter. Any one of the embodiments, aspects and preferred features or ranges as disclosed in this application may be combined in any combination, unless otherwise stated herein or if technically clearly not feasible to a skilled person.

[1] A multi-aziridine crosslinker composition, wherein the multi-aziridine crosslinker composition is an aqueous dispersion having a pH ranging from 8 to 14 and comprising a multi-aziridine compound in dispersed form, wherein said multi-aziridine compound has:
a. from 2 to 6 of the following structural units A:

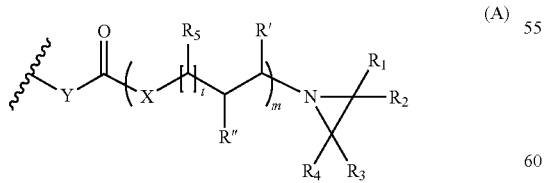

(A)

whereby
$R_1$ is H,
$R_2$ and $R_4$ are independently chosen from H or an aliphatic hydrocarbon group containing from 1 to 4 carbon atoms,
$R_3$ is an aliphatic hydrocarbon group containing from 1 to 4 carbon atoms, mist,
R' and R" are according to (1) or (2):
(1) R'=H or an aliphatic hydrocarbon group containing from 1 to 14 carbon atoms, and
R"=H, an aliphatic hydrocarbon group containing from 1 to 14 carbon atoms, a cycloaliphatic hydrocarbon group containing from 5 to 12 carbon atoms, an aromatic hydrocarbon group containing from 6 to 12 carbon atoms, $CH_2$—O—(C=O)—R''', $CH_2$—O—R'''', or $CH_2$—(OCR''''HCR''''H)$_n$—OR''''', whereby R''' is an aliphatic hydrocarbon group containing from 1 to 14 carbon atoms and R'''' is an aliphatic hydrocarbon group containing from 1 to 14 carbon atoms or an aromatic hydrocarbon group containing from 6 to 12 carbon atoms, n being from 1 to 35, R'''' independently being H or an aliphatic hydrocarbon group containing from 1 to 14 carbon atoms and R''''' being an aliphatic hydrocarbon group containing from 1 to 4 carbon atoms,
(2) R' and R" form together a saturated cycloaliphatic hydrocarbon group containing from 5 to 8 carbon atoms,
t is 0,
$R_5$ is H or $CH_3$,
X is O and Y is NH;
b. one or more linking chains wherein each one of these linking chains links two of the structural units A; and
c. a molecular weight in the range from 500 to 10000 Daltons.

[2] The multi-aziridine crosslinker composition of embodiment 1, wherein $R_2$ is H, $R_3$ is $C_2H_5$ and $R_4$ is H.

[3] The multi-aziridine crosslinker composition of embodiment 1, wherein $R_2$ is H, $R_3$ is $CH_3$ and $R_4$ is H.

[4] The multi-aziridine crosslinker composition of embodiment 1, wherein $R_2$ is H, $R_3$ is $CH_3$ and $R_4$ is $CH_3$.

[5] The multi-aziridine crosslinker composition of any of embodiments [1] to [4], wherein the linking chains consist of from 4 to 300 atoms, more preferably from 5 to 250 and most preferably from 6 to 100 atoms and the linking chains are a collection of atoms covalently connected which collection of atoms consists of i) carbon atoms, ii) carbon and nitrogen atoms, or iii) carbon, oxygen and nitrogen atoms.

[6] The multi-aziridine crosslinker composition of any of embodiments [1] to [5], wherein the multi-aziridine compound contains 2 or 3 structural units A.

[7] The multi-aziridine crosslinker composition of any of embodiments [1] to [6], wherein
R' and R" are according to (1) or (2):
(1) R'=H or an alkyl group containing from 1 to 2 carbon atoms; R"=H, an aliphatic hydrocarbon group containing from 1 to 4 carbon atoms, $CH_2$—O—(C=O)—R''', $CH_2$—O—R'''', or $CH_2$—(OCR''''HCR''''H)$_n$—OR''''', whereby R''' is an alkyl group containing from 1 to 14 carbon atoms and R'''' is an alkyl group containing from 1 to 14 carbon atoms, n being from 1 to 35, R'''' independently being H or a methyl group and R''''' being an alkyl group containing from 1 to 4 carbon atoms;
(2) R' and R" form together a saturated cycloaliphatic hydrocarbon group containing from 5 to 8 carbon atoms.

[8] The multi-aziridine crosslinker composition of any of embodiments [1] to [7], wherein R' is H and R"=an alkyl group containing from 1 to 4 carbon atoms, CH$_2$—O—(C=O)—R''', CH$_2$—O—R'''', whereby R''' is an alkyl group containing from 3 to 12 carbon atoms and R'''' is an alkyl group containing from 1 to 14 carbon atoms.

[9] The multi-aziridine crosslinker composition of any of embodiments [1] to [8], wherein the multi-aziridine compound comprises one or more connecting groups wherein each one of these connecting groups connects two of the structural units A, whereby the connecting groups consist of at least one functionality selected from the group consisting of aliphatic hydrocarbon functionality (preferably containing from 1 to 8 carbon atoms), cycloaliphatic hydrocarbon functionality (preferably containing from 4 to 10 carbon atoms), aromatic hydrocarbon functionality (preferably containing from 6 to 12 carbon atoms), isocyanurate functionality, iminooxadiazindione functionality, ether functionality, ester functionality, amide functionality, carbonate functionality, urethane functionality, urea functionality, biuret functionality, allophanate functionality, uretdione functionality and any combination thereof.

[10] The multi-aziridine crosslinker composition of embodiment [9], wherein the connecting groups consist of at least one aliphatic hydrocarbon functionality and/or at least one cycloaliphatic hydrocarbon functionality and optionally at least one aromatic hydrocarbon functionality and optionally an isocyanurate functionality or an iminooxadiazindione functionality.

[11] The multi-aziridine crosslinker composition of embodiment [9], wherein the connecting groups consist of at least one aliphatic hydrocarbon functionality and/or at least one cycloaliphatic hydrocarbon functionality and an isocyanurate functionality or an iminooxadiazindione functionality.

[12] The multi-aziridine crosslinker composition of any of embodiments [1] to [8], wherein the multi-aziridine compound comprises one or more connecting groups wherein each one of these connecting groups connects two of the structural units A, wherein the connecting groups consist of (i) at least two aliphatic hydrocarbon functionality and (ii) an isocyanurate functionality or an iminooxadiazindione functionality, and wherein a pendant group is present on a connecting group, whereby the pendant group has the following structural formula:

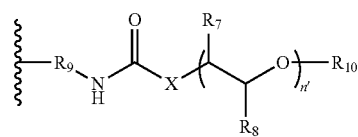

n' is the number of repeating units and is an integer from 1 to 50, preferably from 2 to 30, more preferably from 5 to 20.

X is O or NH, preferably X is O,

R$_7$ and R$_8$ are independently H or CH$_3$ in each repeating unit,

R$_9$ is an aliphatic hydrocarbon group, preferably containing from 1 to 8 carbon atoms, and R$_{10}$ preferably is an aliphatic hydrocarbon group containing from 1 to 20 carbon atoms (preferably CH$_3$), a cycloaliphatic hydrocarbon group containing from 5 to 20 carbon atoms or an aromatic hydrocarbon group containing from 6 to 20 carbon atoms.

[13] A multi-aziridine crosslinker composition, wherein the composition is an aqueous dispersion having a pH ranging from 8 to 14 and comprising a multi-aziridine compound in dispersed form, wherein said multi-aziridine compound has from 2 to 6 of the structural units A as defined in embodiment [1], whereby R$_1$, R$_2$, R$_3$, R$_4$, R', R'', m, t, R$_5$, X and Y are as defined in any of embodiment [1] to [12], wherein the multi-aziridine compound having a molecular weight from 500 Daltons to 10000 Daltons and wherein the multi-aziridine compound further comprises one or more connecting groups wherein each one of these connecting groups connects two of the structural units A, in which the connecting groups consist of at least one functionality selected from the group consisting of aliphatic hydrocarbon functionality (preferably containing from 1 to 8 carbon atoms), cycloaliphatic hydrocarbon functionality (preferably containing from 4 to 10 carbon atoms), aromatic hydrocarbon functionality (preferably containing from 6 to 12 carbon atoms), isocyanurate functionality, iminooxadiazindione functionality, ether functionality, ester functionality, amide functionality, carbonate functionality, urethane functionality, urea functionality, biuret functionality, allophanate functionality, uretdione functionality and any combination thereof.

[14] The multi-aziridine crosslinker composition of any of embodiments [1] to [13], wherein structural units A are according to the following structural formula D:

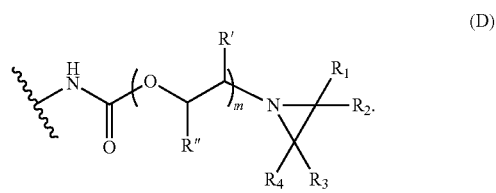

[15] The multi-aziridine crosslinker composition of any of embodiments [1] to [14], wherein the multi-aziridine compound is obtained by reacting at least a polyisocyanate and a compound B with the following structural formula:

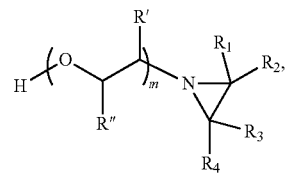

whereby the molar ratio of compound B to polyisocyanate is from 2 to 6, more preferably from 2 to 4 and most preferably from 2 to 3, and whereby m, R', R'', R$_1$, R$_2$, R$_3$ and R$_4$ are defined as in the preceding embodiments.

[16] The multi-aziridine crosslinker composition of embodiment [15], wherein the polyisocyanate is a polyisocyanate with aliphatic reactivity.

[17] The multi-aziridine crosslinker composition of embodiment [15] or [16], wherein compound B is obtained by reacting at least a non-OH functional monoepoxide compound with an aziridine with the following structural formula:

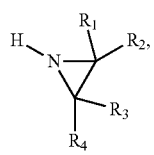

whereby $R_1$, $R_2$, $R_3$ and $R_4$ are defined as in the preceding embodiments.

[18] The multi-aziridine crosslinker composition of embodiment [17], wherein the non-OH functional monoepoxide compound is selected from the group consisting of ethylene oxide, propylene oxide, 2-ethyl oxirane, n-butylglycidylether, 2-ethylhexylglycidylether, glycidyl neodecanoate and any mixture thereof.

[19] The multi-aziridine crosslinker composition of any of embodiments [15] to [18], wherein the multi-aziridine compound is the reaction product of a least compound (B), a polyisocyanate and alkoxy poly(propyleneglycol) and/or poly(propyleneglycol).

[20] The multi-aziridine crosslinker composition of any of embodiments [1] to [19], wherein the multi-aziridine compound has a molecular weight of from 600 to 5000 Daltons, more preferably the multi-aziridine compound has a molecular weight of at least 800 Daltons, even more preferably at least 840 Daltons, even more preferably at least 1000 Daltons and preferably at most 3800 Daltons, more preferably at most 3600 Daltons, more preferably at most 3000 Daltons, more preferably at most 1600 Daltons, even more preferably at most 1400 Daltons.

[21] The multi-aziridine crosslinker composition of any of embodiments [1] to [20], wherein the aqueous dispersion comprises aziridinyl group functional molecules having a molecular weight lower than 580 Daltons in an amount lower than 5 wt. %, on the total weight of the aqueous dispersion, whereby the molecular weight is determined using LC-MS as described in the description.

[22] The multi-aziridine crosslinker composition of any of embodiments [1] to [21], wherein the pH of the aqueous dispersion is at least 8.5, more preferably at least 9, more preferably at least 9.5.

[23] The multi-aziridine crosslinker composition of any of embodiments [1] to [22], wherein the pH of the aqueous dispersion is at most 14, more preferably at most 13, even more preferably at most 12, even more preferably at most 11.5.

[24] The multi-aziridine crosslinker composition of any of embodiments [1] to [23], wherein the pH of the aqueous dispersion is in the range from 9.5 to 11.5.

[25] The multi-aziridine crosslinker composition of any of embodiments [1] to [24], wherein the aqueous dispersion comprises comprises ammonia, a secondary amine(s), a tertiary amine(s), LiOH, NaOH and/or KOH to adjust the pH to the desired value, preferably the aqueous dispersion comprises a tertiary amine selected from n-ethylmorpholine, n-methyl piperidine, n,n-dimethyl butyl amine, dimethyl isopropyl amine, dimethyl n-propyl amine, dimethyl ethylamine, triethylamine and/or dimethyl benzyl amine, most preferably comprises triethylamine to adjust the pH to the desired value

[26] The multi-aziridine crosslinker composition of any of embodiments [1] to [25], wherein the amount of water in the aqueous dispersion is at least 15 wt. %, preferably at least 20 wt. %, more preferably at least 30 wt. %, even more preferably at least 40 wt. %, on the total weight of the aqueous dispersion.

[27] The multi-aziridine crosslinker composition of any of embodiments [1] to [26], wherein the amount of water in the aqueous dispersion is at most 95 wt. %, preferably at most 90 wt. %, more preferably at most 85 wt. %, more preferably at most 80 wt. %, even more preferably at most 70 wt. %, even more preferably at most 60 wt. %, on the total weight of the aqueous dispersion.

[28] The multi-aziridine crosslinker composition of any of embodiments [1] to [27], wherein the amount of said multi-aziridine compound in the aqueous dispersion is at least 5 wt. %, preferably at least 10 wt. %, more preferably at least 15 wt. %, more preferably at least 20 wt. %, even more preferably at least 25 wt. %, even more preferably at least 30 wt. %, even more preferably at least 35 wt. %, on the total weight of the aqueous dispersion.

[29] The multi-aziridine crosslinker composition of any of embodiments [1] to [28], wherein the amount of said multi-aziridine compound in the aqueous dispersion is at most 70 wt. %, preferably at most 65 wt. %, more preferably at most 60 wt. %, even more preferably at most 55 wt. %, on the total weight of the aqueous dispersion.

[30] The multi-aziridine crosslinker composition of any of embodiments [1] to [29], wherein the aqueous dispersion further comprises an organic solvent in an amount of at most 35 wt. %, preferably at most 30, for example at most 25, for example at most 20, for example at most 12, for example at most 10, for example at most 8, for example at most 5, for example at most 4, for example at most 3, for example at most 2, for example at most 1, for example at most 0.5, for example at most 0.2, for example at most 0.1 wt % on the total weight of the aqueous dispersion.

[31] The multi-aziridine crosslinker composition of any of embodiments [1] to [30], wherein the solids content of the aqueous dispersion is at least 5, preferably at least 10, even more preferably at least 20, even more preferably at least 30, even more preferably at least 35 and at most 70, more preferably at most 65 and even more preferably at most 55 wt. %.

[32] The multi-aziridine crosslinker composition of any of embodiments [1] to [31], wherein the particles have a scatter intensity based average hydrodynamic diameter from 30 to 650 nanometer, preferably from 50 to 500 nm, more preferably from 70 to 350 nm, even more preferably from 120 to 275 nm.

[33] The multi-aziridine crosslinker composition of any of embodiments [1] to [32], wherein the aqueous dispersion comprises a dispersant.

[34] The multi-aziridine crosslinker composition of any of embodiments [1] to [32], wherein the aqueous dispersion comprises a separate surface-active molecule component as dispersant in an amount ranging from 0.1 to 20 wt. %, preferably at least 0.5, more preferably at least 1, even more preferably at least 2, even more preferably at least 3 wt. %, on the total weight of the aqueous dispersion.

[35] The multi-aziridine crosslinker composition of embodiment [34], wherein the dispersant is a polymer having a number average molecular weight of at least 2000 Daltons, more preferably at least 2500 Daltons, more preferably at least 3000 Daltons, more preferably at least 3500 Daltons, more preferably at least 4000 Daltons, and preferably at most 1000000 Daltons, more preferably at most 100000, at most 10000 Daltons.

[36] The multi-aziridine crosslinker composition of any of embodiments [33] to [35], wherein the dispersant is a polyether, more preferably a polyether copolymer, even more preferably a polyether block copolymer, even more preferably a poly(alkylene oxide) block copolymer, even more preferably a poly(ethylene oxide)-co-poly(propylene oxide) block copolymer.

[37] The multi-aziridine crosslinker composition of any of embodiments [1] to [36], wherein the aqueous dispersion has a storage stability of at least 2 weeks, more preferably of at least 3 weeks and even more preferably of at least 4 weeks at 50° C.

[38] The multi-aziridine crosslinker composition of any of embodiments [1] to [37], wherein the number of consecutive C atoms and optionally O atoms between the N atom of the urethane group in a structural unit D and the next N atom which is either present in the linking chain or which is the N atom of the urethane group of another structural unit D is at most 9.

[39] The multi-aziridine crosslinker composition of any of embodiments [1] to [38], wherein the multi-aziridine crosslinker composition is used for crosslinking a carboxylic acid functional polymer dissolved and/or dispersed, preferably dispersed, in an aqueous medium, whereby the carboxylic acid functional polymer contains carboxylic acid groups and/or carboxylate groups.

[41] The multi-aziridine crosslinker composition of any of embodiments [1] to [36], wherein the multi-aziridine crosslinker composition does not contain polymer to be crosslinked with the multi-aziridine crosslinker composition.

A process for preparing the multi-aziridine crosslinker composition of any of embodiments [1] to [40], wherein the process comprises dispersing the multi-aziridine compound as defined in any of the preceding embodiments into water to obtain an aqueous dispersion and adjusting the pH of the aqueous dispersion to the desired value or wherein the process comprises dispersing the multi-aziridine compound as defined in any of the preceding embodiments into a mixture of water and at least one base which mixture has a pH such as to obtain an aqueous dispersion with the desired pH value.

[42] The process of embodiment [41], wherein the process comprises mixing basic aqueous medium into the multi-aziridine compound as defined in any of the preceding embodiments, whereby the pH of the basic aqueous medium is chosen such as to obtain an aqueous dispersion with the desired pH value.

[43] The process of embodiment [41] or [42], wherein the process comprises
A) optionally, but preferably, mixing the multi-aziridine compound as defined in any of the preceding embodiments in an organic solvent,
B) mixing the multi-aziridine compound as defined in any of the preceding embodiments or the solution obtained in step A) with a dispersant to obtain a composition comprising the multi-aziridine compound and dispersant,
C) mixing water and base or mixing basic aqueous medium into said composition comprising the multi-aziridine compound and dispersant, to obtain a dispersion
D) optionally, but preferably, evaporating organic solvent from said dispersion to obtain a further dispersion, and optionally mixing additional water or basic aqueous medium into said further dispersion, to obtain the aqueous dispersion of any of embodiments [1] to [39].

[44] Use of the multi-aziridine crosslinker composition of any of embodiments [1] to [40] or obtained with the process according to any of embodiments [41] to [43] for crosslinking a carboxylic acid functional polymer dissolved and/or dispersed, preferably dispersed, in an aqueous medium, whereby the amounts of aziridinyl groups and of carboxylic acid groups are chosen such that the stoichiometric amount (SA) of aziridinyl groups on carboxylic acid groups is from 0.1 to 2.0, more preferably from 0.2 to 1.5, even more preferably from 0.25 to 0.95, most preferably from 0.3 to 0.8.

[45] A two-component coating system comprising a first component and a second component each of which is separate and distinct from each other and wherein the first component comprises a carboxylic acid functional polymer dissolved and/or dispersed, preferably dispersed, in an aqueous medium and the second component comprises the multi-aziridine crosslinker composition of any of embodiments [1] to [40] or obtained with the process according to any of embodiments [41] to [43].

[47] A substrate having a coating obtained by (i) applying a coating composition obtained by mixing the first and second component of the two-component coating system of embodiment [45] to a substrate and (ii) drying the coating composition by evaporation of volatiles.

The present invention is now illustrated by reference to the following examples. Unless otherwise specified, all parts, percentages and ratios are on a weight basis.

Particle Size Measurement

The scatter intensity based average hydrodynamic diameter of the particles was determined using a method derived from the ISO 22412:2017 standard with a Malvern Zetasizer Nano S90 DLS instrument that was operated under the following settings: as material, a polystyrene latex was defined with a RI of 1.590 and an absorption of 0.10 with a continuous medium of demineralized water with a viscosity of 0.8812 cP and a RI of 1.332 at 25° C. Measurements were performed in DTS0012 disposable cuvettes, obtained from Malvern Instruments (Malvern, Worcestershire, United Kingdom). Measurements were performed under a 173° backscatter angle as an average of 3 measurements after 120 seconds equilibration, consisting of 10-15 subruns—optimized by the machine itself. The focus point of the laser was at a fixed position of 4.65 cm and data was analyzed using a general-purpose data fitting process. Samples were prepared by diluting 0.05 g (1 droplet) sample dispersion in approximately 5 mL of demineralized water. If the sample still looked hazy it was further diluted with distilled water until it becomes almost clear. This method is suitable for determining particle sizes from 2 nm to 3 μm.

pH Measurement

The pH of a sample is determined based on the ISO 976:2013 standard. Samples are measured at 23° C. using a Metrohm 691 pH-meter equipped with combined glass electrode and PT-1000 temperature sensor. The pH-meter is calibrated using buffer solutions of pH 7.00 and 9.21 prior to use.

NCO Determination

The NCO content of a sample is determined based on the ASTM D2572-19 standard. In the procedure, the sample is reacted with excess n-dibutylamine. The excess of n-dibutylamine is subsequently back-titrated with standard 1N hydrochloric acid (HCl). The difference in titration volume between the sample and a blank is the measure of the isocyanate content on solids, according to the following formula: % $NCO_{solids}$=[(Vb−Vm)*N*4.2]/(A*s/100), where % $NCO_{solids}$ is the isocyanate content on solids, Vb is the volume of HCl used in the blank, Vm is the volume of HCl used in the sample, N is the normality of the HCl solution, A is the sample weight in grams and s is the solids content of the sample in %. Measurements are performed in duplicate using a potentiometric endpoint on a Metrohm 702SM Titrino titrator (accepting the measurement if the difference between duplicates is <0.1%$_{NCO}$).

AV Determination

The acid value on solid material (AV) of a sample is determined based on the ASTM D1639-90(1996)e1 standard. In the procedure, the sample, dissolved in a good solvent, is titrated with alcoholic potassium hydroxide solution of a known concentration (KOH). The difference in titration volume between the sample and a blank is the measure of the acid value on solids, according to the following formula: AV=[(Vblank−Vsample)*N$_{KOH}$*56.1]/(W*S/100), where AV is acid number on solids in mg KOH/g solid material, Vblank is the volume of KOH solution used in the blank, Vsample is the volume of KOH solution used in the sample, N$_{KOH}$ is the normality of the KOH solution, W is the sample weight in grams and S is the solids content of the sample in %. Measurements are performed in duplicate using a potentiometric endpoint on a Metrohm 702SM Titrino titrator (accepting the measurement if the difference between duplicates is <0.1 mg KOH/g solid material).

Chemical Resistance

Chemical resistance testing based on DIN 68861-1:2011-01 standard.

Unless indicated otherwise the chemical resistance is tested as follows:

Coating compositions are composed at 0.9 stoichiometric amounts (SA) of total carboxylic acid-reactive functional groups (e.g. aziridine) compared to carboxylic acid functional groups. Coating compositions are treated as described in the examples, and then cast at 100 μm wet layer thickness using a wire bar applicator. After casting, films were dried for 1 hour at 25° C., then annealed at 50° C. for 16 hours. Subsequently, a piece of cotton wool was soaked in 1:1 Ethanol:demineralized water (by weight) and placed on the film for 60 minutes (unless indicated otherwise). After removal of the cotton wool and overnight recovery, the spots were scored according to the following ranks:

1 Complete coating degradation
2 Structural damage to the coating
3 Severe marking on coating, visible from multiple directions
4 Slight marking on coating, visible from specific angles
5 No observed marking or gloss change Viscosity Measurements:

The apparent viscosity is determined according to ISO 2555:2018. The measurement is performed at 23° C. on a Brookfield DVE-LV viscometer (single-cylinder geometry) at 60 rpm. The spindle is selected from S62, S63 or S64, using the lowest numbered spindle (i.e. the largest spindle) that yields a reading between 10% and 100% torque.

Size Exclusion Chromatography with NMP-MEK

The molecular weight distribution is measured with an Alliance Separation Module (Waters e2695), including a pump, autoinjector, degasser, and column oven. The eluent is n-Methyl pyrrolidone (NMP) 80%/methylethylketone 20% (MEK) with the addition of 0.01 M lithium bromide. The injection volume was 150 μl. The flow was established at 1.0 ml/min. Three PL Mixed B (Polymer Laboratories) with a guard column (5 μm PL) were applied at a temperature of 70° C. The detection was performed with a differential refractive index detector (Waters 2414) at 50° C. The samples are dissolved in the eluent using a concentration of 5 mg polymer per mL solvent. The solubility is judged with a laser pen after 24 hours stabilization at room temperature; if any scattering is visible the samples are filtered first. The calculation was performed with eight polystyrene standards (polymer standard services), ranging from 160 to 1,737,000 Dalton. The calculation was performed with Empower software (Waters) with a third order calibration curve. The obtained molar masses are polystyrene equivalent molar masses (Dalton).

T$_g$ Measurement by DSC

The glass transition temperature (T$_g$) of a polymer is measured by Differential Scanning calorimetry (DSC) at a heating rate of 10° C./min in N$_2$ atmosphere at a flow rate of 50 mL/minute, on a TA Instruments Discovery DSC 250 apparatus according to the following method: a sample of 5±0.5 mg was weighed and placed in the DSC cell at a temperature between 20 and 25° C. The sample was cooled down to −120° C. and equilibrated at that temperature; upon equilibration the sample was heated up from −120° C. up to 160° C. at a heating rate of 5° C./minute; the sample was kept at that temperature for 2 minutes and it was subsequently cooled down to −120° C. at a cooling rate of 20° C./min; once the sample reached −120° C. the temperature was maintained for 5 minutes; subsequently, the sample was heated up from −120° C. up to 220° C. at a heating rate of 5° C./minute (thermograph A). The T$_g$ was measured from this last thermograph (thermograph A) as the half width of the step in the DSC signal (DSC thermograph, Heat Flow vs. Temperature) observed for a T$_g$. The processing of the DSC signal and the determination of the T$_g$ was carried out using TRIOS software package version 5.0 provided by TA instruments.

Low Molecular Weight Fraction by LC-MS

LC system: Agilent 1290 Infinity II; Detector #1: Agilent 1290 Infinity II PDA; Detector #2: Agilent iFunnel 6550 Q-TOF-MS.

LC-MS analysis for the low molecular weight fraction was performed using the following procedure. A solution of ~100 mg/kg of material was prepared gravimetrically in methanol and stirred. 0.5 μl of this solution was injected into a UPLC equipped with ESI-TOF-MS detection. The column used was a 100×2.1 mm, 1.8 um, Waters HSS T3 C18 operated at 40° C. Flow rate was 0.5 ml·min$^{-1}$. Solvents used were 10 mM NH$_4$CH$_3$COO in water set to pH 9.0 with NH$_3$ (Eluent A), Acetonitrile (B) and THF (C). Two binary gradients were applied from 80/20 A/B to 1/99 A/B in 10 minutes and from 1/99 A/B to 1/49/50 A/B/C in 5 minutes, after which starting conditions are applied (80/20 A/B). Assuming linear MS response of all components over all response ranges and an equal ionization efficiency for all components, Total Ion Current signals were integrated. In case of coelution extracted ion chromatograms of that particular species were integrated. Dividing the integrated signal of a particular low-molecular weight peak by the total integrated sample signal yields the fraction of that low molecular weight species.

MALDI-ToF-MS

All MALDI-ToF-MS spectra were acquired using a Bruker Ultraflextreme MALDI-ToF mass spectrometer. The instrument is equipped with a Nd:YAG laser emitting at 1064 nm and a collision cell (not used for these samples). Spectra were acquired in the positive-ion mode using the reflectron, using the highest resolution mode providing accurate masses (range 60-7000 m/z). Cesium Tri-iodide (range 0.3-3.5 kDa) was used for mass calibration (calibration method: IAV Molecular Characterisation, code MC-MS-05). The laser energy was 20%. The samples were dissolved in THF at approx. 50 mg/mL. The matrix used was: DCTB (trans-2-[3-(4-tert-Butylphenyl)-2-methyl-2- propenylidene]malononitrile), CAS Number 300364-84-5. The matrix solution was prepared by dissolving 20 mg in 1 mL of THF.

Sodium iodide was used as salt (NaI, CAS Number 7681-82-5); 10 mg was dissolved in 1 ml THF with a drop of MeOH added. Ratio sample:matrix:salt=10:200:10 (μl), after mixing, 0.5 μL was spot on MALDI plate and allowed to air-dry. The peaks measured in the MALDI spectrum are sodium adducts of multi-aziridine compounds, and in the context of this specification the molecular weight (MW) of the multi-aziridine compound corresponds to MW=Obs. [M+M$_{cation}$]−M$_{cation}$, where Obs. [M+M$_{cation}$] is the MALDI-TOF MS peak and M$_{cation}$ is the exact mass of the cation used for making the adduct (in this case sodium with M$_{cation}$=23.0 Da). Multi-aziridine compounds can be identified by comparing the MW with the exact molecular mass (i.e. the sum of the—non-isotopically averaged—atomic masses of its constituent atoms) of a theoretical structure, using a maximum deviation of 0.6 Da.

Genotoxicity Testing

Genotoxicity of was evaluated by the ToxTracker® assay (Toxys, Leiden, the Netherlands). The ToxTracker assay is a panel of several validated Green Fluorescent Protein (GFP)-based mouse embryonic stem (mES) reporter cell lines that can be used to identify the biological reactivity and potential carcinogenic properties of newly developed compounds in a single test. This methodology uses a two step-approach.

In the first step a dose range finding was performed using wild-type mES cells (strain B4418). 20 different concentrations for each compound was tested, starting at 10 mM in DMSO as highest concentration and nineteen consecutive 2-fold dilutions. Next, genotoxicity of was evaluated using specific genes linked to reporter genes for the detection of DNA damage; i.e. Bscl2 (as elucidated by U.S. Pat. No. 9,695,481B2 and EP2616484B1) and Rtkn (Hendriks et. al. Toxicol. Sci. 2015, 150, 190-203) biomarkers. Genotoxicity was evaluated at 10, 25 and 50% cytotoxicity in absence and presence of rat S9 liver extract-based metabolizing systems (aroclor1254-induced rats, Moltox, Boone, NC, USA). The independent cell lines were seeded in 96-well cell culture plates, 24 h after seeding the cells in the 96-well plates, fresh ES cell medium containing the diluted test substance was added to the cells. For each tested compound, five concentrations are tested in 2-fold dilutions. The highest sample concentration will induce significant cytotoxicity (50-70%). In case of no or low cytotoxicity, 10 mM or the maximum soluble mixture concentration is used as maximum test concentration. Cytotoxicity is determined by cell count after 24 h exposure using a Guava easyCyte 10HT flow cytometer (Millipore).

GFP reporter induction is always compared to a vehicle control treatment. DMSO concentration is similar in all wells for a particular compound and never exceeds 1%. All compounds were tested in at least three completely independent repeat experiments. Positive reference treatment with cisplatin (DNA damage) were included in all experiments. Metabolic was evaluated by addition of S9 liver extract. Cells are exposed to five concentrations of the test compound in the presence of S9 and required co-factors (RegenSysA+B, Moltox, Boone, NC, USA) for 3 h. After washing, cells are incubated for 24 h in fresh ES cell medium. Induction of the GFP reporters is determined after 24 h exposure using a Guava easyCyte 10HT flow cytometer (Millipore). Only GFP expression in intact single cells is determined. Mean GFP fluorescence and cell concentrations in each well is measured, which is used for cytotoxicity assessment. Data was analyzed using ToxPlot software (Toxys, Leiden, the Netherlands). The induction levels reported are at compound concentrations that induce 10%, 25% and 50% cytotoxicity after 3 h exposure in the presence of S9 rat liver extract and 24 h recovery or alternatively after 24 h exposure when not in the presence of S9 rat liver extract.

A positive induction level of the biomarkers is defined as equal to or higher than a 2-fold induction at at least one of 10, 25 and 50% cytotoxicity in the absence or presence of the metabolizing system rat S9 liver extract; a weakly positive induction as higher than 1.5-fold and lower than 2-fold induction at at least one of 10, 25 and 50% cytotoxicity (but lower than 2-fold at 10, 25 and 50% cytotoxicity) in the absence or presence of the metabolizing system rat S9 liver extract and a negative as lower than or equal to a 1.5-fold induction at 10, 25 and 50% cytotoxicity in the absence and presence of rat S9 liver extract-based metabolizing systems.

Components and Abbreviations Used:

Dimethylol propionic acid (DMPA, CAS No. 4767-03-7) was obtained from Perstop Polyols.

Polypropylene glycol with an average Mn of 2000 Da and polypropylene glycol with an average Mn of 1000 Da (CAS No. 25322-69-4) were obtained from BASF.

IPDI (5-Isocyanato-1-(isocyanatomethyl)-1,3,3-trimethylcyclohexane, Desmodur® I, isophorone diisocyanate, CAS No. 4098-71-9) was obtained from Covestro.

DBTDL (dibutyltin dilaurate, CAS No. 77-58-7) was obtained from Reaxis.

Triethylamine (TEA, CAS No. 121-44-8) was obtained from Arkema.

Nonylphenol ethoxylate 9 eo (CAS No. 68412-54-4) was obtained from Sigma-Aldrich.

Hydrazine (16% solution in water, CAS No. 302-01-2) was obtained from Honeywell.

2-Methylaziridine (propyleneimine, CAS No. 75-55-8) was obtained from Menadiona S.L. (Palafolls, Spain).

n-butylglycidyl ether (CAS No. 2426-08-6) was obtained from Alfa Aesar (a division of Thermo Fisher Scientific).

Potassium carbonate (CAS No. 584-08-7) was obtained from Alfa Aesar (a division of Thermo Fisher Scientific).

Bismuth neodecanoate (CAS No. 34364-26-6) obtained from TIB chemicals AG (Mannheim, Germany).

2-Methyltetrahydrofuran (CAS No. 96-47-9) was obtained from Merck KgaA.

Desmodur® N3600, Desmodur® N3900, Desmodur® N3800 and Desmodur® N3400 were obtained from Covestro.

Acetone (CAS No. 67-64-1) was obtained from Sigma-Aldrich.

Maxemul™ 7101 was obtained from Croda Int. PLC.

Sodium lauryl sulphate (30% solution in water, CAS No. 73296-89-6) was obtained from BASF.

Methyl methacrylate (CAS No. 80-62-6) was obtained from Lucite Int.

n-Butyl acrylate (CAS No. 141-32-2) was obtained from Dow Chemical.

Methacrylic acid (CAS No. 79-41-4) was obtained from Lucite Int.

Ammonium persulphate (CAS No. 7727-54-0) was obtained from United Initiators.

Ammonia (25% solution in water, CAS No. 1336-21-6) was obtained from Merck.

Polytetrahydrofuran with an average Mn of 650 Da (pTHF650, polytetramethylene ether glycol with an OH-number of 172 mg KOH/g) and polytetrahydrofuran with an average Mn of 1000 Da (pTHF1000, CAS No. 25190-06-1)

were obtained from BASF. 2-Methyl-1,3-propane diol (CAS No. 2163-42-0) was obtained from Lyondell. Cyclohexanedimethanol (CAS No. 105-08-8) was obtained from Alfa Aesar (a division of Thermo Fisher Scientific).

TMP (1,1,1-Tris(hydroxymethyl)propane, CAS No. 77-99-6) was obtained from Sigma-Aldrich (a division of Merck KGaA).

Isophthalic acid (CAS No. 121-91-5) was obtained from Alfa Aesar (a division of Thermo Fisher Scientific).

Sorbic acid (CAS No. 110-44-1) was obtained from Alfa Aesar (a division of Thermo Fisher Scientific).

Methylethylketone (MEK, 2-butanone, CAS No. 78-93-3) was obtained from Alfa Aesar (a division of Thermo Fisher Scientific).

Terephthalic acid (CAS No. 100-21-0) was obtained from Sigma-Aldrich (a division of Merck KGaA).

Decane dioic acid (Sebacic acid, CAS No. 111-20-6) was obtained from Acros Organics (a division of Thermo Fisher Scientific).

Butyl stannoic acid (CAS No. 2273-43-0) was obtained from Sigma-Aldrich (a division of Merck KGaA).

o-xylene (CAS No. 95-47-6) was obtained from Alfa Aesar (a division of Thermo Fisher Scientific).

Maleic anhydride (CAS No. 108-31-6) was obtained from Alfa Aesar (a division of Thermo Fisher Scientific).

Dimethylethanolamine (CAS No. 108-01-0) was obtained from Sigma-Aldrich (a division of Merck KGaA).

Trimethylolpropane tris(2-methyl-1-aziridinepropionate), CAS No. 64265-57-2, CX-100 was obtained from DSM.

Atlas™ G-5000 was obtained from Croda Int. PLC.

Atlas™ G-5002L-LQ was obtained from Croda Int. PLC.

Di(propylene glycol) dimethyl ether (Proglyde DMM, CAS No. 111109-77-4) was obtained from Dow Inc.

Pluronic® P84 (CAS No. 9003-11-6) was obtained from BASF.

Pluronic® PE9400 (CAS No. 9003-11-6) was obtained from BASF.

Sodium hydroxide (CAS No. 1310-73-2) was obtained from Merck.

N-methylpiperidine (CAS No. 626-67-5) was obtained from Sigma-Aldrich (a division of Merck KGaA).

1-Butanol (CAS No. 71-36-3) was obtained from Sigma-Aldrich (a division of Merck KGaA).

2,2-Dimethylaziridine (CAS No. 2658-24-4) was obtained from Enamine LLC (Monmouth Jct., NJ, United States of America).

Toluene (CAS No. 108-88-3) was obtained from Sigma-Aldrich.

Dimethylformamide (CAS No. 68-12-2) was obtained from Acros Organics (a division of Thermo Fisher Scientific).

1-(2-hydroxyethyl)ethyleneimine) (CAS No. 1072-52-2) was obtained from Tokyo Chemical Industry Co., Ltd.

Pluronic® PE6800 (CAS No. 9003-11-6) was obtained from BASF.

Vestanat® T 1890/100, an isophorone diisocyanate based isocyanurate (CAS No. 67873-91-0) was obtained from Evonik.

1-methoxy-2-propyl acetate (MPA, propylene glycol methyl ether acetate, CAS No. 108-65-6) was obtained from Shell Chemicals.

Polyethylene Glycol Monomethyl Ether (CAS No. 9004-74-4) with a number average molecular weight of 500 Da was obtained from Acros Organics (a division of Thermo Fisher Scientific).

Jeffamine® XTJ-436 (CAS No. 118270-87-4) was obtained from Huntsman.

2-Ethylhexyl glycidyl ether (CAS No. 2461-15-6) was obtained from Sigma-Aldrich (a division of Merck KGaA).

Cardura E10P (CAS No. 26761-45-5) was obtained from Hexion Inc.

H12MDI (4,4'-Methylenebis(phenyl isocyanate, Desmodur® W, CAS No. 101-66-8) was obtained from Covestro.

Durez-ter S105-110 (a polyester polyol with an OH-number of 110 mg KOH/g, based on adipic acid and hexane diol) obtained from Sumitomo Bakelite.

Ymer™ N-120 was obtained from Perstorp.

Vestamin A-95 (CAS No. 34730-59-1) was obtained from Evonik.

Voranol CP450 (CAS No. 25791-96-2) was obtained from Dow Inc.

Bisphenol A diglycidyl ether (CAS No. 1675-54-3) was obtained from Tokyo Chemical Industry Co., Ltd.

Voranol™ P-400 was obtained from Dow Inc.

Tin 2-ethylhexanoate (CAS No. 301-10-0) was obtained from Sigma-Aldrich.

Tegomer® D3403 was obtained from Evonik.

3-Methyl-1-phenyl-2-phospholene-1-oxide (CAS No. 707-61-9) was obtained from Sigma-Aldrich.

Toluene diisocyanate (TDI, CAS No. 26471-62-5) was obtained from Covestro.

Triton X-100 (CAS No. 9002-93-1) was obtained from Sigma-Aldrich.

Synthesis of P1, a Waterborne Polyurethane

A one-liter flask (equipped with a thermometer and an overhead stirrer), was charged with 29.9 grams of dimethylol propionic acid, 282.1 grams of a polypropylene glycol with a calculated average molecular weight (M) of 2000 Da and an OH-value of 56±2 mg KOH/g polypropylene glycol), 166.5 grams of a polypropylene glycol with a calculated average molecular weight (M) of 1000 Da and an OH-value of 112±2 mg KOH/g polypropylene glycol, and 262.8 grams of isophorone diisocyanate (the average molecular weight of each of the polyols is calculated from its OH-value according to the equation: $M=2*56100/[$OH-value in mg KOH/g polypropylene glycol). The reaction mixture was placed under $N_2$ atmosphere, heated to 50° C. and subsequently 0.07 g dibutyltin dilaurate were added to the reaction mixture. An exothermic reaction was observed; however proper care was taken in order for the reaction temperature not to exceed 97° C. The reaction was maintained at 95° C. for an hour. The NCO content of the resultant polyurethane P1' was 7.00% on solids as determined according to the method described herein (theoretically 7.44%) and the acid value of the polyurethane P1' was 16.1±1 mg KOH/g polyurethane P1'. The polyurethane P1' was cooled down to 60° C. and 18.7 grams of triethylamine were added, and the resulting mixture was stirred for 30 minutes. Subsequently, an aqueous dispersion of the polyurethane P1' (the aqueous dispersion of the polyurethane P1' is further referred to as P1) was prepared as follows: the thus prepared mixture of the polyurethane P1' and triethylamine was fed—at room temperature over a time period of 60 minutes—to a mixture of 1100 grams of demineralized water, 19.5 grams of nonylphenol ethoxylate (9 ethoxylate groups), and 4.0 grams of triethylamine. After the feed was completed, the mixture was stirred for additional 5 minutes, and subsequently 111.2 grams of hydrazine (16 wt % solution in water) were added to the mixture. The aqueous dispersion of the polyurethane P1' thus prepared was stirred for an additional 1 h and P1 was obtained.

EXAMPLE 1

A 1 L round bottom flask equipped with a condensor was placed under a $N_2$ atmosphere and charged with propylene imine (120 gram), n-butyl glycidyl ether (189.0 gram) and K$_2$CO$_3$ (15.0 gram) and heated to 80° C. in 30 min, after which the mixture was stirred for 21 h at T=80° C. After filtration the excess of PI was removed in vacuo, followed by further purification via vacuum distillation, resulting in a colorless low viscous liquid.

186.2 grams of the resulting material (1-butoxy-3-(2-methylaziridin-1-yl)propan-2-ol) was charged to a reaction flask equipped with a thermometer, together with 0.02 grams of bismuth neodecanoate and 77.8 grams of 2-methyltetrahydrofuran. The mixture was stirred with a mechanical upper stirrer under a nitrogen atmosphere and heated to 50° C. A solution of 200 grams of Desmodur N 3600 in 77.8 grams of 2-methyltetrahydrofuran was then added dropwise in 45 minutes to the reaction flask, whereafter the mixture was heated further to 70° C. Samples were taken at regular intervals and the reaction progress was monitored using a Bruker Alpha FT-IR spectrometer until no NCO-stretch at 2200-2300 cm$^{-1}$ was observed. The solvent was removed in vacuo to obtain a clear, yellowish highly viscous liquid. The calculated molecular weight of the theoretical main component was 1065.74 Da, chemical structure is shown below.

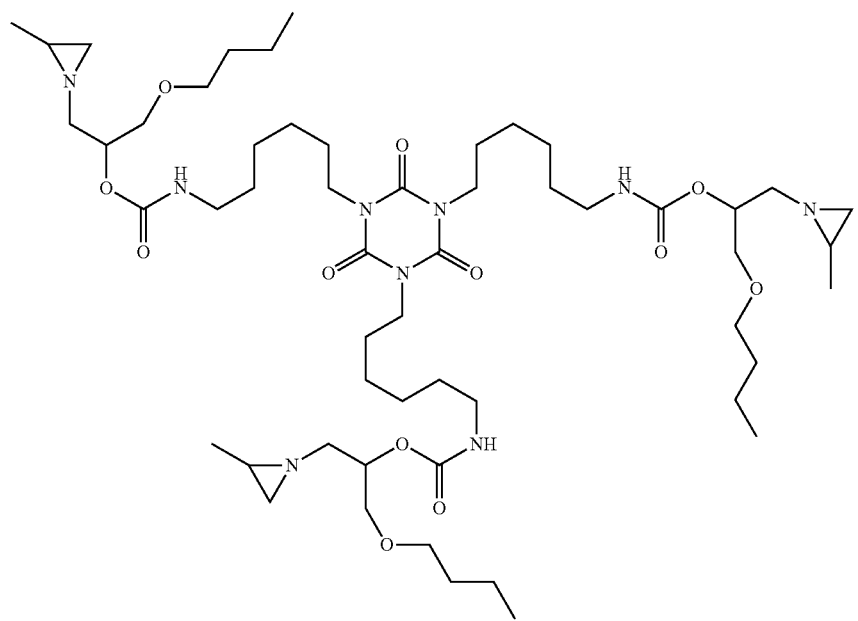 [SMILES: CCCCOCC(CN1CC1C)OC(=O)NCCCCCCn1c(=O)n(CCCCCCNC(=O)OC(COCCCC)CN2CC2C)c(=O)n(CCCCCCNC(=O)OC(COCCCC)CN2CC2C)c1=O]

Molecular weight was confirmed by Maldi-TOF-MS: Calcd. [M+Na+]=1088.74 Da; Obs. [M+Na+]=1088.78 Da. The following components with a mass below 580 Da were determined by LC-MS and quantified:

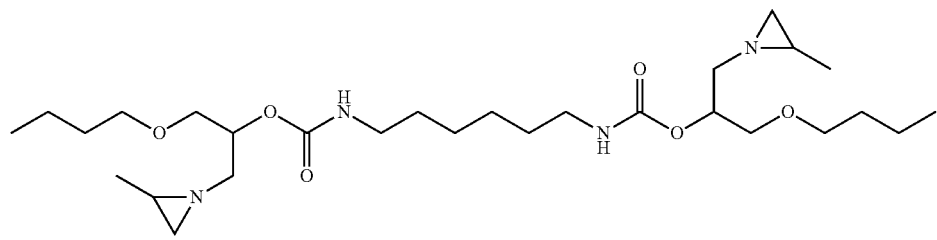 [SMILES: CCCCOCC(CN1CC1C)OC(=O)NCCCCCCNC(=O)OC(COCCCC)CN1CC1C]

was present in the composition at 0.21 wt. % and

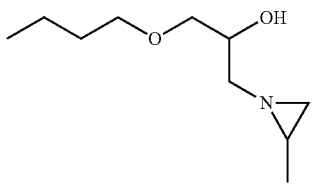

was present at less than 0.01 wt. %.
Genotoxicity Test

|  | Without S9 rat liver extract | | | | | | With S9 rat liver extract | | | | | |
|---|---|---|---|---|---|---|---|---|---|---|---|---|
|  | Bscl 2 | | | Rtkn concentration | | | Bscl 2 | | | Rtkn | | |
|  | 10 | 25 | 50 | 10 | 25 | 50 | 10 | 25 | 50 | 10 | 25 | 50 |
| Composition 1 | 1.1 | 1.1 | 1.1 | 0.8 | 0.8 | 0.6 | 1.0 | 1.0 | 0.9 | 0.9 | 0.8 | 0.6 |

The genotoxicity test results show that the crosslinker composition of Example 1 is non-genotoxic.

Subsequently, 15 grams of the viscous liquid obtained in the previous step was mixed with 7.5 grams of acetone and incubated at 50° C. until a homogeneous solution was obtained. To this solution was added 0.03 grams of triethylamine (TEA) and then 1.5 grams of molten Maxemul™ 7101 dispersant. The resulting mixture was stirred for 5 minutes at room temperature using an IKA T25 Digital Ultra-Turrax® mixer with S 25 N-18G head at 2,000 rpm. Then, stirring was increased to 10,000 rpm and 15 grams of demineralized water, brought to pH 11 using triethylamine, was added gradually to the mixture over 15 minutes. During this addition process, the mixer was moved around the reaction vessel continuously. After completion of the addition, the resulting dispersion was stirred at 5,000 rpm for 10 more minutes, and the pH of the dispersion was set to 11 with TEA.
Genotoxicity Test

|  | Without S9 rat liver extract | | | | | | With S9 rat liver extract | | | | | |
|---|---|---|---|---|---|---|---|---|---|---|---|---|
|  | Bscl 2 | | | Rtkn concentration | | | Bscl 2 | | | Rtkn | | |
|  | 10 | 25 | 50 | 10 | 25 | 50 | 10 | 25 | 50 | 10 | 25 | 50 |
| Dispersion 1 | 1.0 | 1.1 | 1.1 | 1.3 | 1.3 | 1.3 | 1.1 | 1.2 | 1.2 | 0.9 | 1.2 | 1.2 |

The genotoxicity test results show that the dispersion of Example 1 is non-genotoxic.

Functional performance and stability of the crosslinker dispersion were assessed using spot tests on coating surfaces, based on procedures from the DIN 68861-1 standard, and viscosity measurements as well as particle size measurements. For these tests, the crosslinker dispersion was stored in an oven at 50° C. for 4 weeks. Every week, the viscosity and the particle size of the crosslinker dispersion were determined. Additionally, every week, 2.0 grams of the aged crosslinker dispersion was mixed with 21 grams of Polymer P1 under continuous stirring, and the resulting mixture was further stirred for 30 minutes. This coating composition was filtered and applied to Leneta test cards using 100 µm wire rod applicators (Test 1). For reference, films were also cast from the same composition lacking the crosslinker dispersion (Test Blank). The films were dried for 1 hour at 25° C., then annealed at 50° C. for 16 hours. Subsequently, a piece of cotton wool was soaked in 1:1 EtOH:demineralized water and placed on the film for 1 hour. After removal of the EtOH and 60 minutes recovery, the following results were obtained (a score of 1 indicates complete degradation of the film, 5 indicates no damage visible):
Performance and Stability Test

| Sample | Week 0 | Week 1 | Week 2 | Week 3 | Week 4 |
|---|---|---|---|---|---|
| Particle size 1 (nm) | 183 | 178 | 174 | 187 | 175 |
| Viscosity 1 (mPa · s) | 208 | 230 | 202 | 211 | 206 |
| Test 1 | 5 | 5 | 5 | 5 | 4 |
| Test Blank | 1 | 1 | 1 | 1 | 1 |

Performance of the synthesized compound as a crosslinker was further assessed using spot tests on coating surfaces with different binder systems.

Waterborne acrylic binder 1 was synthesized as follows.

A 2 L four-necked flask equipped with a thermometer and overhead stirrer was charged with sodium lauryl sulphate (30% solids in water, 18.6 grams of solution) and demineralized water (711 grams). The reactor phase was placed under $N_2$ atmosphere and heated to 82° C. A mixture of demineralized water (112 grams), sodium lauryl sulphate (30% solids in water, 37.2 grams of solution), methyl methacrylate (209.3 grams), n-butyl acrylate (453.56 grams) and methacrylic acid (34.88 grams) was placed in a large feeding funnel and emulsified with an overhead stirrer (monomer feed). Ammonium persulphate (1.75 grams) was dissolved in demineralized water (89.61 grams) and placed in a small feeding funnel (initiator feed). Ammonium persulphate (1.75 grams) was dissolved in demineralized water (10.5 grams), and this solution was added to the reactor phase. Immediately afterwards, 5% by volume of the monomer feed was added to the reactor phase. The reaction mixture then exothermed to 85° C. and was kept at 85° C. for 5 minutes. Then, the residual monomer feed and the initiator feed were fed to the reaction mixture over 90 minutes, maintaining a temperature of 85° C. After completion of the feeds, the monomer feed funnel was rinsed with demineralized water (18.9 grams) and reaction temperature maintained at 85° C. for 45 minutes. Subsequently, the mixture was cooled to room temperature and brought to pH=7.2 with ammonia solution (6.25 wt. % in demineralized water), and brought to 40% solids with further demineralized water.

Waterborne acrylic binder 2 was synthesized as Waterborne acrylic binder 1, but using 174.4 grams of methyl methacrylate instead of 209.3 grams, and using 488.4 grams of n-butyl acrylate instead of 453.56 grams.

Waterborne acrylic binder 3 was synthesized as Waterborne acrylic binder 1, but using 139.5 grams of methyl methacrylate instead of 209.3 grams, and using 523.3 grams of n-butyl acrylate instead of 453.56 grams.

For further spot tests, additional crosslinker dispersion, synthesized as described earlier, was stored in an oven at 50° C. for 4 weeks. Every week, for each of the aforementioned waterborne acrylic binders 1, 2 and 3, 4.1 grams of the aged crosslinker dispersion was mixed with 21 grams of the binder under continuous stirring, and the resulting mixture was further stirred for 30 minutes. This coating composition was filtered and applied to Leneta test cards using 100 µm wire rod applicators (Tests 1-WA1, 1-WA2 and 1-WA3, for the corresponding binders). For reference, films were also cast from the same composition lacking the crosslinker dispersion (Tests Blank-WA1, Blank-WA2 and Blank-WA3). The films were dried for 1 hour at 25° C., then annealed at 50° C. for 16 hours. Subsequently, a piece of cotton wool was soaked in 1:1 EtOH:demineralized water and placed on the film for 1 hour. After removal of the EtOH and 60 minutes recovery, the following results were obtained (a score of 1 indicates complete degradation of the film, 5 indicates no damage visible):

| Sample | Week 0 | Week 1 | Week 2 | Week 3 | Week 4 |
| --- | --- | --- | --- | --- | --- |
| Test 1-WA1 | 5 | 4 | 4 | 4 | 4 |
| Test Blank-WA1 | 1 | 1 | 1 | 1 | 1 |
| Test 1-WA2 | 5 | 5 | 5 | 5 | 4 |
| Test Blank-WA2 | 1 | 1 | 1 | 1 | 1 |
| Test 1-WA3 | 5 | 5 | 5 | 5 | 4 |
| Test Blank-WA3 | 1 | 1 | 1 | 1 | 1 |

A waterborne polyurethane binder was synthesized as follows.

A 1 L flask equipped with a thermometer and overhead stirrer was charged with DMPA (12.9 grams), pTHF650 (168.4 grams) and IPDI (140.5 grams). The reaction mixture was placed under $N_2$ atmosphere, heated to 50° C. and 0.03 g of bismuth neodecanoate was added. The mixture was allowed to exotherm and kept at 90° C. for 2.5 hours. The NCO content of the resultant urethane prepolymer was 8.00% on solids (theoretically 8.80%). The prepolymer was cooled down to 75° C. and TEA (8.73 grams) was added and the resulting mixture was stirred for 15 minutes. A dispersion of the resultant prepolymer was made by feeding 290 gram of this prepolymer to demineralized water (686 grams) at room temperature in 30 minutes. After the feed was completed, the mixture was stirred for 5 minutes and hydrazine (16% solution in water, 51.0 grams) was added. The dispersion was stirred for a further 1 h. Subsequently, the mixture was cooled to room temperature and brought to 30% solids with further demineralized water.

For further spot tests, additional crosslinker dispersion, synthesized as described earlier, was stored in an oven at 50° C. for 4 weeks. Every week, 1.6 grams of the aged crosslinker dispersion was mixed with 21 grams of the waterborne polyurethane binder under continuous stirring, and the resulting mixture was further stirred for 30 minutes. This coating composition was filtered and applied to Leneta test cards using 100 μm wire rod applicators (Test 1-WU1). For reference, films were also cast from the same composition lacking the crosslinker dispersion (Test Blank-WU1). The films were dried for 1 hour at 25° C., then annealed at 50° C. for 16 hours. Subsequently, a piece of cotton wool was soaked in 1:1 EtOH:demineralized water and placed on the film for 1 hour. After removal of the EtOH and 60 minutes recovery, the following results were obtained (a score of 1 indicates complete degradation of the film, 5 indicates no damage visible):

| Sample | Week 0 | Week 1 | Week 2 | Week 3 | Week 4 |
| --- | --- | --- | --- | --- | --- |
| Test 1-WU1 | 5 | 5 | 5 | 5 | 5 |
| Test Blank-WU1 | 3 | 3 | 3 | 3 | 3 |

A waterborne polyester binder was synthesized as follows.

A 3-liter flask equipped with a thermometer, overhead stirrer and a fractionating column for distillation was charged with 2-methyl-1,3-propanediol (795 grams), 1,4-cyclohexanedimethanol (139 grams), trimethylolpropane (10.4 grams), isophthalic acid (288 grams), terephthalic acid (859 grams), decane dioic acid (189 grams) and butyl stannoic acid (2.26 grams). The reaction mixture was placed under $N_2$ atmosphere and gradually heated to 240° C. while removing water. The reaction was monitored by acid value and stopped when an acid number of 1.0 was reached. Subsequently, the reaction mixture was cooled to 120° C. and the fractionating column was replaced by a Dean-Stark trap. Next, 120 grams of xylene was added to the reaction mixture, followed by 181 grams of maleic anhydride. The mixture was then heated to 200° C., refluxing the azeotropic mixture to further remove water. During the reaction, further 2-methyl-1,3-propanediol was added to maintain a hydroxyl delta value of 11.0, and the reaction was continued to an acid number of 10.0 was reached. Subsequently, the reaction mixture was cooled to 160° C., and 85.2 grams of sorbic acid was added in 3 doses over 30 minutes, allowing the reaction to exotherm. Reaction temperature was maintained for 3 hours, and then the mixture was cooled to 80° C. and 650 grams of methyl ethyl ketone (MEK) was added slowly.

Of the polyester solution obtained as described above, 300 grams was added to a 1-liter flask equipped with a thermometer, overhead stirrer and a condensor. The reaction mixture was placed under $N_2$ atmosphere and heated to 75° C. Then, under continued stirring, 9.5 grams of dimethylethanolamine (DMEA) was added over 10 minutes, followed by 500 grams of demineralized water over 60 minutes. The reactor contents were then cooled down to 50° C. and the MEK was removed in vacuo. Finally, the mixture was set to pH=8.4 using DMEA and a solids content of 30% using demineralized water, and cooled to room temperature.

For further spot tests, additional crosslinker dispersion, synthesized as described earlier, was stored in an oven at 50° C. for 4 weeks. Every week, 4.5 grams of the aged crosslinker dispersion was mixed with 10.5 grams of the waterborne polyester binder under continuous stirring, and the resulting mixture was further stirred for 30 minutes. This coating composition was filtered and applied to Leneta test cards using 100 μm wire rod applicators (Test 1-WE1). For reference, films were also cast from the same composition lacking the crosslinker dispersion (Test Blank-WE1). The films were dried for 1 hour at 25° C., then annealed at 50° C. for 16 hours. Subsequently, a piece of cotton wool was soaked in 1:1 EtOH:demineralized water and placed on the film for 1 hour. After removal of the EtOH and 60 minutes recovery, the following results were obtained (a score of 1 indicates complete degradation of the film, 5 indicates no damage visible):

| Sample | Week 0 | Week 1 | Week 2 | Week 3 | Week 4 |
| --- | --- | --- | --- | --- | --- |
| Test 1-WE1 | 4 | 4 | 4 | 4 | 4 |
| Test Blank-WE1 | 1 | 1 | 1 | 1 | 1 |

EXAMPLE 2

As example 1, where during the water addition step 15 grams of demineralized water, brought to pH 9 with TEA, was used instead of the demineralized water brought to pH 11, and the dispersion was set to pH 9 with TEA.

Functional performance and stability of the crosslinker dispersion were assessed using spot tests on coating surfaces with Polymer P1 as described for Example 1.

Performance and Stability Test

| Sample | Week 0 | Week 1 | Week 2 | Week 3 | Week 4 |
|---|---|---|---|---|---|
| Particle size 2 (nm) | 192 | 182 | 184 | 187 | 183 |
| Viscosity 2 (mPa · s) | 222 | 254 | 234 | 193 | 168 |
| Test 2 | 5 | 4 | 4 | 4 | 4 |
| Test Blank | 1 | 1 | 1 | 1 | 1 |

EXAMPLE 3

As example 1, where during the water addition step 15 grams of demineralized water, brought to pH 8 with TEA, was used instead of the demineralized water brought to pH 11, and the dispersion was set to pH 8 with TEA.

Functional performance and stability of the crosslinker dispersion was assessed using spot tests on coating surfaces with Polymer P1 as described for Example 1.

Performance and Stability Test

| Sample | Week 0 | Week 1 | Week 2 | Week 3 | Week 4 |
|---|---|---|---|---|---|
| Particle size 3 (nm) | 184 | 176 | 181 | 179 | 176 |
| Viscosity 3 (mPa · s) | 192 | 226 | 268 | 264 | 248 |
| Test 3 | 5 | 4 | 4 | 4 | 4 |
| Test Blank | 1 | 1 | 1 | 1 | 1 |

COMPARATIVE EXAMPLE C1

For Comparative Example C1, crosslinker CX-100-trimethylolpropane tris(2-methyl aziridinepropionate)—was used:

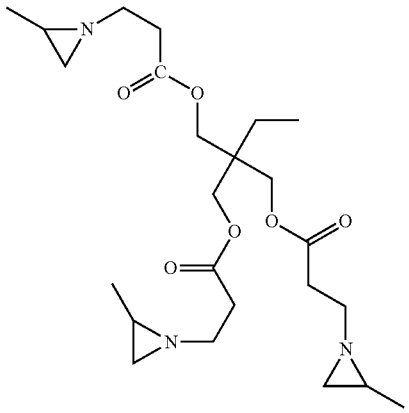

Genotoxicity Test

| | Without S9 rat liver extract | | | | | | With S9 rat liver extract | | | | | |
|---|---|---|---|---|---|---|---|---|---|---|---|---|
| | Bscl 2 | | | Rtkn | | | Bscl 2 | | | Rtkn | | |
| | concentration | | | | | | | | | | | |
| | 10 | 25 | 50 | 10 | 25 | 50 | 10 | 25 | 50 | 10 | 25 | 50 |
| Comp. Ex. 1 | 1.2 | 1.5 | 2.0 | 1.4 | 2.0 | 3.2 | 1.7 | 2.3 | 2.1 | 3.0 | 4.3 | 3.4 |

The genotoxicity test results show that the crosslinker of Comp Ex 1 is genotoxic.

Of this crosslinker, 7.5 grams was mixed with 3.75 grams of acetone and incubated at 50° C. until a homogeneous solution was obtained. To this solution was added 0.03 grams of triethylamine and then 0.75 grams of molten Atlas™ G-5000 dispersant. The resulting mixture was stirred for 5 minutes at room temperature using an IKA T25 Digital Ultra-Turrax® mixer with S 25 N-18G head at 2,000 rpm. Then, stirring was increased to 10,000 rpm and 7.5 grams of demineralized water, brought to pH 11 using triethylamine (TEA), was added gradually to the mixture over 15 minutes. During this addition process, the mixer was moved around the reaction vessel continuously. After completion of the addition, the resulting mixture was stirred at 5,000 rpm for 10 more minutes, and the pH of the mixture was set to 11.

Functional performance and stability of the crosslinker mixture were assessed using spot tests on coating surfaces, based on procedures from the DIN 68861-1 standard, and viscosity measurements as well as particle size measurements. For these tests, the crosslinker dispersion was stored in an oven at 50° C. for 4 weeks. Every week, the viscosity and the particle size of the crosslinker dispersion were determined. Additionally, every week, 0.8 grams of the aged crosslinker mixture was mixed with 21 grams of Polymer P1 under continuous stirring, and the resulting coating composition was further stirred for 30 minutes. This coating composition was filtered and applied to Leneta test cards using 100 μm wire rod applicators (Test C1). For reference, films were also cast from the same composition lacking the crosslinker dispersion (Test Blank). The films were dried for 1 hour at 25° C., then annealed at 50° C. for 16 hours. Subsequently, a piece of cotton wool was soaked in 1:1 EtOH:demineralized water and placed on the film for 1 hour. After removal of the EtOH and 60 minutes recovery, the following results were obtained (a score of 1 indicates complete degradation of the film, 5 indicates no damage visible):

Performance and Stability Test

| Sample | Week 0 | Week 1 | Week 2 | Week 3 | Week 4 |
|---|---|---|---|---|---|
| Particle size C1 (nm) | N/A | —* | —* | —* | —* |
| Viscosity C1 (mPa · s) | 10 | —* | —* | —* | —* |
| Test C1 | 5 | —* | —* | —* | —* |
| Test Blank | 1 | 1 | 1 | 1 | 1 |

*Crosslinker mixture gelled during first week of storage

COMPARATIVE EXAMPLE C2

As example C1, where during the water addition step 7.5 grams of demineralized water, brought to pH 9 with TEA, was used instead of the demineralized water brought to pH 11, and the resulting mixture was set to pH 9 with TEA.

Functional performance and stability of the crosslinker mixture were assessed using spot tests on coating surfaces with Polymer P1 as described for Comparative Example C1.

Performance and Stability Test

| Sample | Week 0 | Week 1 | Week 2 | Week 3 | Week 4 |
|---|---|---|---|---|---|
| Particle size C2 (nm) | N/A | —* | —* | —* | —* |
| Viscosity C2 (mPa · s) | 10 | —* | —* | —* | —* |
| Test C2 | 5 | —* | —* | —* | —* |
| Test Blank | 1 | 1 | 1 | 1 | 1 |

*Crosslinker mixture gelled during first week of storage

COMPARATIVE EXAMPLE C3

As example C1, where during the water addition step 7.5 grams of demineralized water, brought to pH 8 with TEA, was used instead of the demineralized water brought to pH 11, and the resulting mixture was set to pH 8 with TEA.

Functional performance and stability of the crosslinker mixture were assessed using spot tests on coating surfaces with Polymer P1 as described for Comparative Example C1.

Performance and Stability Test

| Sample | Week 0 | Week 1 | Week 2 | Week 3 | Week 4 |
|---|---|---|---|---|---|
| Particle size C3 (nm) | N/A | —* | —* | —* | —* |
| Viscosity C3 (mPa · s) | 20 | —* | —* | —* | —* |
| Test C3 | 5 | —* | —* | —* | —* |
| Test Blank | 1 | 1 | 1 | 1 | 1 |

*Crosslinker mixture gelled during first week of storage

EXAMPLE 4

As Example 1, where 1.5 grams of Atlas™ G-5002L-LQ was used as a dispersant instead of Maxemul™ 7101.

Functional performance and stability of the crosslinker dispersion was assessed using spot tests on coating surfaces with Polymer P1 as described for Example 1.

Performance and Stability Test

| Sample | Week 0 | Week 1 | Week 2 | Week 3 | Week 4 |
|---|---|---|---|---|---|
| Particle size 4 (nm) | 216 | 221 | 220 | 219 | 220 |
| Viscosity 4 (mPa · s) | 196 | 186 | 198 | 218 | 190 |
| Test 4 | 5 | 5 | 5 | 5 | 3 |
| Test Blank | 1 | 1 | 1 | 1 | 1 |

EXAMPLE 5

As Example 1, where the viscous crosslinker liquid was mixed with 7.5 grams of Proglyde™ DMM instead of acetone, and 2.0 grams of Pluronic® P84 was used as a dispersant instead of Maxemul™ 7101.

Functional performance and stability of the crosslinker dispersion was assessed using spot tests on coating surfaces with Polymer P1 as described for Example 1.

Performance and Stability Test

| Sample | Week 0 | Week 1 | Week 2 | Week 3 | Week 4 |
|---|---|---|---|---|---|
| Particle size 5 (nm) | 570 | 496 | 490 | 539 | 511 |
| Viscosity 5 (mPa · s) | 492 | 464 | 460 | 430 | 422 |
| Test 5 | 4 | 4 | 4 | 4 | 4 |
| Test Blank | 1 | 1 | 1 | 1 | 1 |

EXAMPLE 6

Crosslinker was Synthesized as Example 1.

Subsequently, 15 grams of the viscous liquid obtained in the previous step was mixed with 7.5 grams of Proglyde™ DMM and incubated at 50° C. until a homogeneous solution was obtained. To this solution was added 0.02 grams of sodium hydroxide (NaOH) and then 2.0 grams of Atlas™ G-5002L-LQ dispersant. The resulting mixture was stirred for 5 minutes at room temperature using an IKA T25 Digital Ultra-Turrax® mixer with S 25 N-18G head at 2,000 rpm. Then, stirring was increased to 10,000 rpm and 15 grams of demineralized water, brought to pH 11 using NaOH, was added gradually to the mixture over 15 minutes. During this addition process, the mixer was moved around the reaction vessel continuously. After completion of the addition, the resulting dispersion was stirred at 5,000 rpm for 10 more minutes, and the pH of the dispersion was set to 11 with NaOH.

Functional performance and stability of the crosslinker dispersion were assessed using spot tests on coating surfaces with Polymer P1 as described for Example 1.

Performance and Stability Test

| Sample | Week 0 | Week 1 | Week 2 | Week 3 | Week 4 |
|---|---|---|---|---|---|
| Particle size 6 (nm) | 323 | 303 | 307 | 307 | 291 |
| Viscosity 6 (mPa · s) | 520 | 492 | 420 | 507 | 394 |
| Test 6 | 5 | 5 | 5 | 5 | 4 |
| Test Blank | 1 | 1 | 1 | 1 | 1 |

EXAMPLE 7

Crosslinker was Synthesized as Example 1.

Subsequently, 15 grams of the viscous liquid obtained in the previous step was mixed with 7.5 grams of acetone and incubated at 50° C. until a homogeneous solution was obtained. To this solution was added 0.03 grams of triethylamine (TEA) and then 1.5 grams of molten Maxemul™ 7101 dispersant. The resulting mixture was stirred for 5 minutes at room temperature using an IKA T25 Digital Ultra-Turrax® mixer with S 25 N-18G head at 2,000 rpm. Then, stirring was increased to 10,000 rpm and 15 grams of demineralized water, brought to pH 11 using triethylamine, was added gradually to the mixture over 15 minutes. During this addition process, the mixer was moved around the reaction vessel continuously. After completion of the addition, the resulting dispersion was stirred at 5,000 rpm for 10 more minutes, and the pH of the dispersion was set to 11 with TEA. The acetone was then removed from the dispersion using a rotary evaporator, replenishing water and TEA during the process (adding aliquots after every 5 grams of distillate) to maintain solids and pH levels.

Functional performance and stability of the crosslinker dispersion were assessed using spot tests on coating surfaces with Polymer P1 as described for Example 1.

Performance and Stability Test

| Sample | Week 0 | Week 1 | Week 2 | Week 3 | Week 4 |
|---|---|---|---|---|---|
| Particle size 7 (nm) | 172 | 172 | 171 | 171 | 173 |
| Viscosity 7 (mPa · s) | 14 | 10 | 10 | 20 | 18 |
| Test 7 | 5 | 5 | 5 | 5 | 4 |
| Test Blank | 1 | 1 | 1 | 1 | 1 |

EXAMPLE 8

As Example 7, where 7.5 grams of methylethylketone (MEK) was used as a solvent instead of acetone.

Functional performance and stability of the crosslinker dispersion were assessed using spot tests on coating surfaces with Polymer P1 as described for Example 1.

Performance and Stability Test

| Sample | Week 0 | Week 1 | Week 2 | Week 3 | Week 4 |
|---|---|---|---|---|---|
| Particle size 8 (nm) | 308 | 330 | 326 | 313 | 331 |
| Viscosity 8 (mPa · s) | 8 | 10 | 9 | 17 | 18 |
| Test 8 | 5 | 5 | 5 | 5 | 4 |
| Test Blank | 1 | 1 | 1 | 1 | 1 |

EXAMPLE 9

Crosslinker was synthesized and dispersed as example 1. Functional performance and stability of the crosslinker dispersion were assessed as in example 1, except that every week, 1.0 grams of the aged crosslinker dispersion was mixed with 21 grams of Polymer P1 under continuous stirring, instead of 2.0 grams.

Performance and Stability Test

| Sample | Week 0 | Week 1 | Week 2 | Week 3 | Week 4 |
|---|---|---|---|---|---|
| Particle size 9 (nm) | 837 | 679 | 676 | 674 | 667 |
| Viscosity 9 (mPa · s) | 62 | 46 | 68 | 78 | 82 |
| Test 9 | 5 | 5 | 5 | 4 | 4 |
| Test Blank | 1 | 1 | 1 | 1 | 1 |

EXAMPLE 10

As example 9, except that every week, 3.0 grams of the aged crosslinker dispersion was mixed with 21 grams of Polymer P1 under continuous stirring, instead of 1.0 grams.

Performance and Stability Test

| Sample | Week 0 | Week 1 | Week 2 | Week 3 | Week 4 |
|---|---|---|---|---|---|
| Particle size 10 (nm) | 837 | 679 | 676 | 674 | 667 |
| Viscosity 10 (mPa · s) | 62 | 46 | 68 | 78 | 82 |
| Test 10 | 5 | 5 | 5 | 5 | 4 |
| Test Blank | 1 | 1 | 1 | 1 | 1 |

EXAMPLE 11

Crosslinker was Synthesized as Example 1.

Subsequently, 15 grams of the viscous liquid obtained in the previous step was mixed with 7.5 grams of acetone and incubated at 50° C. until a homogeneous solution was obtained. To this solution was added 0.03 grams of triethylamine (TEA) and then 1.5 grams of molten Maxemul™ 7101 dispersant. The resulting mixture was stirred for 30 minutes at room temperature using a three-bladed propeller stirrer with diameter 50 mm at 500 rpm. Then, stirring was increased to 800 rpm and 15 grams of demineralized water, brought to pH 11 using triethylamine, was added gradually to the mixture over 15 minutes. After completion of the addition, the resulting dispersion was stirred at 500 rpm for 10 more minutes, and the pH of the dispersion was set to 11 with TEA.

Functional performance and stability of the crosslinker dispersion were assessed using spot tests on coating surfaces with Polymer P1 as described for Example 1.

Performance and Stability Test

| Sample | Week 0 | Week 1 | Week 2 | Week 3 | Week 4 |
|---|---|---|---|---|---|
| Particle size 11 (nm) | 354 | 359 | 357 | 370 | 357 |
| Viscosity 11 (mPa · s) | 68 | 108 | 84 | 80 | 84 |
| Test 11 | 4 | 4 | 4 | 4 | 4 |
| Test Blank | 1 | 1 | 1 | 1 | 1 |

EXAMPLE 12

Crosslinker was Synthesized as Example 1.

Subsequently, 14.4 grams of the viscous liquid obtained in the previous step was mixed with 6.2 grams of acetone and incubated at 50° C. until a homogeneous solution was obtained. To this solution was added 0.03 grams of triethylamine (TEA) and then 3.0 grams of molten Pluronic® PE9400 dispersant. The resulting mixture was stirred for 5 minutes at room temperature using an IKA T25 Digital Ultra-Turrax® mixer with S 25 N-18G head at 2,000 rpm. Then, stirring was increased to 10,000 rpm and 15 grams of demineralized water, brought to pH 11 using triethylamine, was added gradually to the mixture over 15 minutes. During this addition process, the mixer was moved around the reaction vessel continuously. After completion of the addition, the resulting dispersion was stirred at 5,000 rpm for 10 more minutes, and the pH of the dispersion was set to 11 with TEA.

Functional performance and stability of the crosslinker dispersion were assessed using spot tests on coating surfaces with Polymer P1 as described for Example 1.

Performance and Stability Test

| Sample | Week 0 | Week 1 | Week 2 | Week 3 | Week 4 |
|---|---|---|---|---|---|
| Particle size 12 (nm) | 188 | 225 | 196 | 191 | 201 |
| Viscosity 12 (mPa · s) | 292 | 299 | 346 | 340 | 386 |
| Test 12 | 4 | 4 | 4 | 3 | 3 |
| Test Blank | 1 | 1 | 1 | 1 | 1 |

EXAMPLE 13

Crosslinker was Synthesized as Example 1.

Subsequently, 15 grams of the viscous liquid obtained in the previous step was mixed with 7.5 grams of acetone and incubated at 50° C. until a homogeneous solution was obtained. To this solution was added 0.3 grams of N-methylpiperidine and then 1.5 grams of molten Maxemul™ 7101 dispersant. The resulting mixture was stirred for 5 minutes at room temperature using an IKA T25 Digital Ultra-Turrax® mixer with S 25 N-18G head at 2,000 rpm. Then, stirring was increased to 10,000 rpm and 15 grams of demineralized water was added gradually to the mixture over 15 minutes. During this addition process, the mixer was moved around the reaction vessel continuously. After completion of the addition, the resulting dispersion was stirred at 5,000 rpm for 10 more minutes, and the pH of the dispersion was set to 11 with N-methylpiperidine.

Functional performance and stability of the crosslinker dispersion were assessed using spot tests on coating surfaces with Polymer P1 as described for Example 1.

Performance and Stability Test

| Sample | Week 0 | Week 1 | Week 2 | Week 3 | Week 4 |
|---|---|---|---|---|---|
| Particle size 13 (nm) | 205 | 188 | 197 | 194 | 199 |
| Viscosity 13 (mPa · s) | 394 | 400 | 482 | 499 | 550 |

-continued

| Sample | Week 0 | Week 1 | Week 2 | Week 3 | Week 4 |
|---|---|---|---|---|---|
| Test 13 | 4 | 4 | 4 | 4 | 3 |
| Test Blank | 1 | 1 | 1 | 1 | 1 |

EXAMPLE 14

A 2 L round bottom flask equipped with a condensor was placed under a $N_2$ atmosphere and charged with propylene imine (250 gram), n-butyl glycidyl ether (380 gram) and $K_2CO_3$ (30.0 gram) and heated to 80° C. in 30 min, after which the mixture was stirred for 24 h at T=80° C. After filtration the excess of PI was removed in vacuo, followed by further purification via vacuum distillation, resulting in a colorless low viscous liquid.

530.6 grams of the resulting material (1-butoxy-3-(2-methylaziridin-1-yl)propan-2-ol) was charged to a feed vessel. Separately, 570 grams of Desmodur N 3600 were placed in a reaction flask equipped with a thermometer, together with 0.05 grams of bismuth neodecanoate. This mixture was stirred with a mechanical upper stirrer under a nitrogen atmosphere and heated to 50° C. The solution in the feed vessel was then added dropwise in 90 minutes to the reaction flask, whereafter the mixture was heated further to 70° C. Samples were taken at regular intervals and the reaction progress was monitored using a Bruker Alpha FT-IR spectrometer until no change in NCO-stretch at 2200-2300 $cm^{-1}$ was observed. Subsequently, 12 grams of 1-butanol were added to the mixture, followed by further reaction to complete disappearance of aforementioned NCO-stretch peak. The solvent was removed in vacuo to obtain a highly viscous liquid. The calculated molecular weight of the theoretical main component was 1065.74 Da, chemical structure is shown below.

Subsequently, 3.85 grams of the viscous liquid obtained in the previous step was mixed with 1.92 grams of acetone and incubated at 50° C. until a homogeneous solution was obtained. To this solution was added 0.03 grams of triethylamine (TEA) and then 1.38 grams of molten Maxemul™ 7101 dispersant. The resulting mixture was stirred for 5 minutes at room temperature using an IKA T25 Digital Ultra-Turrax® mixer with S 25 N-18G head at 2,000 rpm. Then, stirring was increased to 10,000 rpm and 77.4 grams of demineralized water, brought to pH 11 using triethylamine, was added gradually to the mixture over 30 minutes. During this addition process, the mixer was moved around the reaction vessel continuously. After completion of the addition, the resulting dispersion was stirred at 5,000 rpm for 10 more minutes, and the pH of the dispersion was set to 11 with TEA.

Functional performance and stability of the crosslinker dispersion were assessed using spot tests on coating surfaces, based on procedures from the DIN 68861-1 standard, and viscosity measurements as well as particle size measurements. For these tests, the crosslinker dispersion was stored in an oven at 50° C. for 4 weeks. Every week, the viscosity and the particle size of the crosslinker dispersion were determined. Additionally, every week, 8.6 grams of the aged crosslinker dispersion was mixed with 10.5 grams of Polymer P1 under continuous stirring, and the resulting mixture was further stirred for 30 minutes. This coating composition was filtered and applied to Leneta test cards using 100 μm wire rod applicators (Test 14). For reference, films were also cast from the same composition lacking the crosslinker dispersion (Test Blank). The films were dried for 1 hour at 25° C., then annealed at 50° C. for 16 hours. Subsequently, a piece of cotton wool was soaked in 1:1 EtOH:demineralized water and placed on the film for 1 hour. After removal of the EtOH and 60 minutes recovery, the following results were obtained (a score of 1 indicates complete degradation of the film, 5 indicates no damage visible):

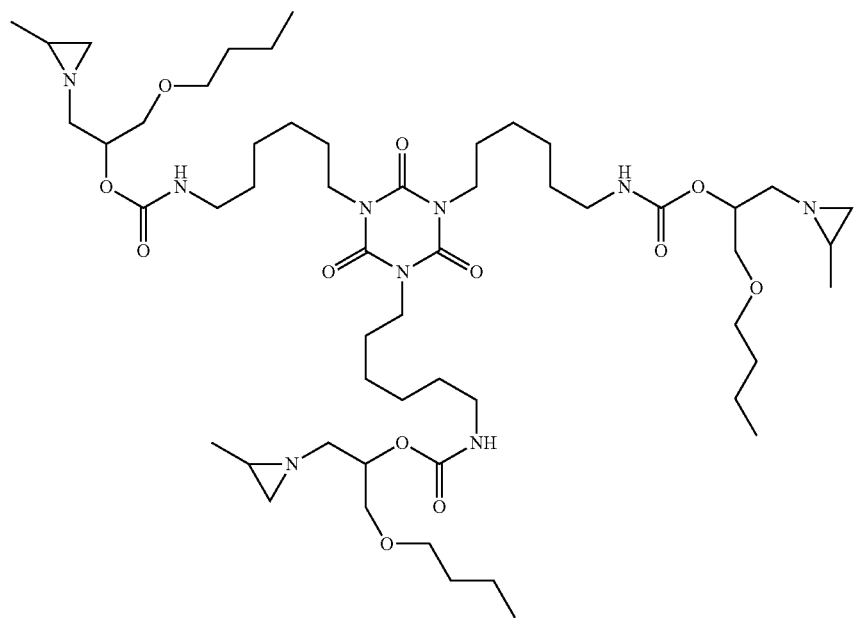 [SMILES: CCCCOCC(CN1CC1C)OC(=O)NCCCCCCn1c(=O)n(CCCCCCNC(=O)OC(COCCCC)CN2CC2C)c(=O)n(CCCCCCNC(=O)OC(COCCCC)CN2CC2C)c1=O]

Performance and Stability Test

| Sample | Week 0 | Week 1 | Week 2 | Week 3 | Week 4 |
|---|---|---|---|---|---|
| Particle size 14 (nm) | 255 | 187 | 194 | 191 | 208 |
| Viscosity 14 (mPa · s) | 1 | 1 | 1 | 1 | 1 |
| Test 14 | 5 | 4 | 4 | 4 | 4 |
| Test Blank | 1 | 1 | 1 | 1 | 1 |

EXAMPLE 15

Two 10 mL vials were placed under a N₂ atmosphere and each was charged with 2,2-dimethylaziridine (4.98 gram), n-butyl glycidyl ether (5.96 gram) and K₂CO₃ (0.3 gram), closed off and heated to 65° C. in a heating block, after which the mixture was stirred for 23 h at 65° C. Subsequently, the reaction mixtures were combined, diluted with 100 mL toluene, and filtered to remove the potassium carbonate. After filtration the excess of dimethylaziridine and the toluene were removed in vacuo, followed by further purification via vacuum distillation, resulting in a slightly yellow low viscous liquid.

12.91 grams of the resulting material (1-butoxy-3-(2,2-dimethylaziridin-1-yl)propan-2-01) was charged to a feed vessel. Subsequently, 42.5 grams of dimethylformamide were added to the feed vessel, and the contents homogenized by stirring. Separately, 12.90 grams of Desmodur N 3600 were placed in a reaction flask equipped with a thermometer, together with 0.002 grams of bismuth neodecanoate and 85 grams of dimethylformamide. This mixture was stirred with a mechanical upper stirrer under a nitrogen atmosphere and heated to 50° C. The solution in the feed vessel was then added dropwise in 30 minutes to the reaction flask, whereafter the mixture was kept at 50° C. Samples were taken at regular intervals and the reaction progress was monitored using a Bruker Alpha FT-IR spectrometer until no NCO-stretch at 2200-2300 cm$^{-1}$ was observed. The solvent was removed in vacuo to obtain a clear, yellowish liquid. The calculated molecular weight of the theoretical main component was 1107.79 Da, chemical structures are shown below.

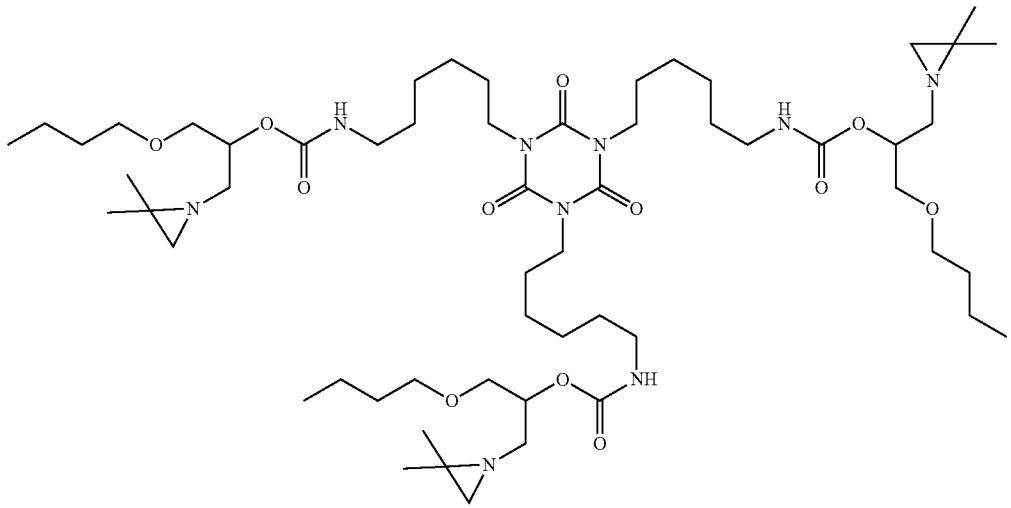 [SMILES: CCCCOCC(CN1CC1(C)C)OC(=O)NCCCCCCn1c(=O)n(CCCCCCNC(=O)OC(COCCCC)CN2CC2(C)C)c(=O)n(CCCCCCNC(=O)OC(COCCCC)CN2CC2(C)C)c1=O]

Molecular weight was confirmed by Maldi-TOF-MS: Calcd. [M+Na+]=1130.79 Da; Obs. [M+Na+]=1130.86 Da. The following components with a mass below 580 Da were determined by LC-MS and quantified:

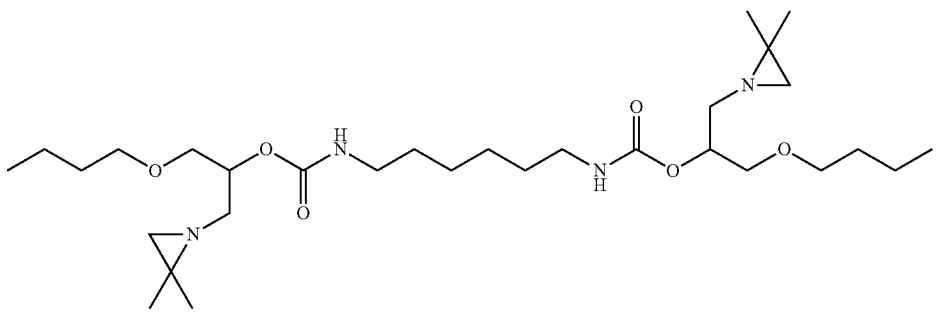 [SMILES: CCCCOCC(CN1CC1(C)C)OC(=O)NCCCCCCNC(=O)OC(COCCCC)CN1CC1(C)C]

was present in the composition at less than 0.01 wt. % and

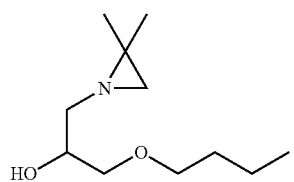

was present in the composition at 0.89 wt. %.

Genotoxicity Test

| | Without S9 rat liver extract | | | | | | With S9 rat liver extract | | | | | |
|---|---|---|---|---|---|---|---|---|---|---|---|---|
| | Bscl 2 | | | Rtkn | | | Bscl 2 | | | Rtkn | | |
| | | | | concentration | | | | | | | | |
| | 10 | 25 | 50 | 10 | 25 | 50 | 10 | 25 | 50 | 10 | 25 | 50 |
| Compound. 15 | 1.2 | 1.2 | 1.1 | 1.2 | 1.2 | 1.2 | 1.1 | 1.1 | 1.1 | 1.2 | 1.2 | 1.3 |

The genotoxicity test results show that the crosslinker of Example 15 is non-genotoxic.

Subsequently, 9.9 grams of the clear liquid obtained in the previous step was mixed with 3.3 grams of acetone and incubated at 50° C. until a homogeneous solution was obtained. To this solution was added 0.03 grams of triethylamine (TEA) and then 1.0 grams of molten Maxemul™ 7101 dispersant. The resulting mixture was stirred for 5 minutes at room temperature using an IKA T25 Digital Ultra-Turrax® mixer with S 25 N-18G head at 2,000 rpm. Then, stirring was increased to 10,000 rpm and 9.9 grams of demineralized water, brought to pH 11 using triethylamine, was added gradually to the mixture over 15 minutes. During this addition process, the mixer was moved around the reaction vessel continuously. After completion of the addition, the resulting dispersion was stirred at 5,000 rpm for 10 more minutes, and the pH of the dispersion was set to 11 with TEA.

Functional performance and stability of the crosslinker dispersion were assessed using spot tests on coating surfaces, based on procedures from the DIN 68861-1 standard, and viscosity measurements as well as particle size measurements. For these tests, the crosslinker dispersion was stored in an oven at 50° C. for 4 weeks. Every week, the viscosity and the particle size of the crosslinker dispersion were determined. Additionally, every week, 1.0 grams of the aged crosslinker dispersion was mixed with 10.5 grams of Polymer P1 under continuous stirring, and the resulting mixture was further stirred for 30 minutes. This coating composition was filtered and applied to Leneta test cards using 100 µm wire rod applicators (Test 15). For reference, films were also cast from the same composition lacking the crosslinker dispersion (Test Blank). The films were dried for 1 hour at 25° C., then annealed at 50° C. for 16 hours. Subsequently, a piece of cotton wool was soaked in 1:1 EtOH:demineralized water and placed on the film for 1 hour. After removal of the EtOH and 60 minutes recovery, the following results were obtained (a score of 1 indicates complete degradation of the film, 5 indicates no damage visible):

Performance and Stability Test

| Sample | Week 0 | Week 1 | Week 2 | Week 3 | Week 4 |
|---|---|---|---|---|---|
| Particle size 15 (nm) | 223 | 243 | 200 | 251 | 249 |
| Viscosity 15 (mPa · s) | 24 | 19 | 14 | 20 | 20 |
| Test 15 | 4 | 4 | 4 | 3 | 3 |
| Test Blank | 1 | 1 | 1 | 1 | 1 |

COMPARATIVE EXAMPLE C4

13.0 grams of 1-(2-hydroxyethyl)ethyleneimine and 175 grams of dimethylformamide were charged to a reaction flask equipped with a thermometer. The mixture was stirred with a mechanical upper stirrer under a nitrogen atmosphere. The mixture was than heated to 50° C., whereafter 0.03 grams of bismuth neodecanoate was charged to the reaction flask. Subsequently, a solution of 30.0 grams of Desmodur N 3600 in 87.5 grams of dimethylformamide was added over 30 minutes. After completion of the feed, the reaction temperature was increased to 80° C. Samples were taken at regular intervals and the reaction progress was monitored using a Bruker Alpha FT-IR spectrometer until no NCO-stretch at 2200-2300 cm$^{-1}$ was observed. The solvent was removed in vacuo to obtain a clear, colorless highly viscous liquid. The calculated molecular weight of the theoretical main component was 765.47 Da, chemical structure is shown below.

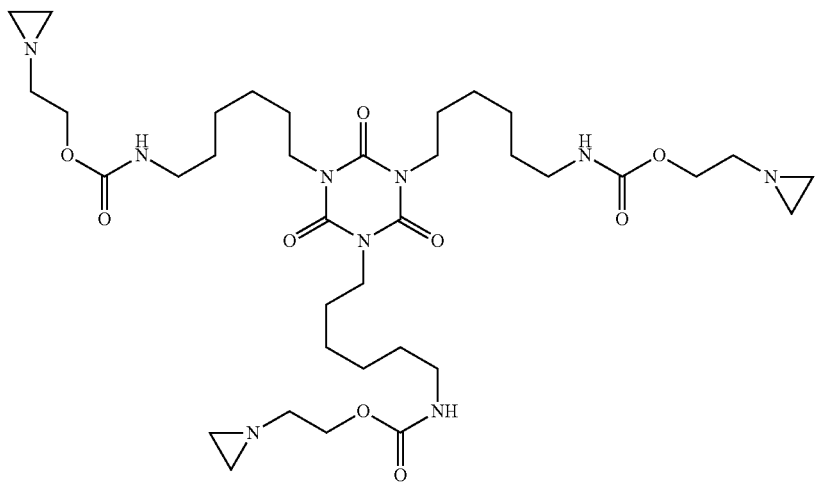 [SMILES: O=C(NCCCCCCn1c(=O)n(CCCCCCNC(=O)OCCN2CC2)c(=O)n(CCCCCCNC(=O)OCCN2CC2)c1=O)OCCN1CC1]

Molecular weight was confirmed by Maldi-TOF-MS: Calcd. [M+Na+]=788.46 Da; Obs. [M+Na+]=788.31 Da.

Subsequently, 7.5 grams of the colorless liquid obtained in the previous step was mixed with 2.5 grams of methylethylketone and incubated at 50° C. until a homogeneous solution was obtained. To this solution was added 0.03 grams of triethylamine (TEA) and then 1.5 grams of Atlas™ G-5002L-LQ dispersant. The resulting mixture was stirred for 5 minutes at room temperature using an IKA T25 Digital Ultra-Turrax® mixer with S 25 N-18G head at 2,000 rpm. Then, stirring was increased to 10,000 rpm and 7.5 grams of demineralized water, brought to pH 11 using triethylamine, was added gradually to the mixture over 15 minutes. During this addition process, the mixer was moved around the reaction vessel continuously. After completion of the addition, the resulting dispersion was stirred at 5,000 rpm for 10 more minutes, and the pH of the dispersion was set to 11 with TEA. Already within 4 hours after conclusion of this 1-(2-hydroxyethyl)ethyleneimine based preparation, severe coagulation was observed. Hence, a storage stable dispersion was not obtained.

COMPARATIVE EXAMPLE C5

Crosslinker was Synthesized as Comparative Example C4.

Subsequently, 7.5 grams of the colorless liquid obtained in the previous step was mixed with 3.8 grams of acetone and incubated at 50° C. until a homogeneous solution was obtained. To this solution was added 0.03 grams of triethylamine (TEA) and then 0.8 grams of molten Maxemul™ 7101 dispersant. The resulting mixture was stirred for 5 minutes at room temperature using an IKA T25 Digital Ultra-Turrax® mixer with S 25 N-18G head at 2,000 rpm. Then, stirring was increased to 10,000 rpm and 7.5 grams of demineralized water, brought to pH 11 using triethylamine, was added gradually to the mixture over 15 minutes. During this addition process, the mixer was moved around the reaction vessel continuously. After completion of the addition, the resulting dispersion was stirred at 5,000 rpm for 10 more minutes, and the pH of the dispersion was set to 11 with TEA. Already within 4 hours after conclusion of this 1-(2-hydroxyethyl)ethyleneimine based preparation, severe coagulation was observed. Hence, a storage stable dispersion was not obtained.

COMPARATIVE EXAMPLE C6

Crosslinker was Synthesized as Comparative Example C4.

Subsequently, 7.5 grams of the colorless liquid obtained in the previous step was mixed with 2.5 grams of Proglyde™ DMM and incubated at 50° C. until a homogeneous solution was obtained. To this solution was added 0.03 grams of triethylamine (TEA) and then 1.5 grams of molten Maxemul™ 7101 dispersant. The resulting mixture was stirred for 5 minutes at room temperature using an IKA T25 Digital Ultra-Turrax® mixer with S 25 N-18G head at 2,000 rpm. Then, stirring was increased to 10,000 rpm and 7.5 grams of demineralized water, brought to pH 11 using triethylamine, was added gradually to the mixture over 15 minutes. During this addition process, the mixer was moved around the reaction vessel continuously. After completion of the addition, the resulting dispersion was stirred at 5,000 rpm for 10 more minutes, and the pH of the dispersion was set to 11 with TEA. Already within 4 hours after conclusion of this 1-(2-hydroxyethyl)ethyleneimine based preparation, severe coagulation was observed. Hence, a storage stable dispersion was not obtained.

EXAMPLE 16

20.0 grams of Desmodur N 3600, 11.98 grams of 1-(2-methylaziridin-1-yl)propan-2-ol and 106 grams of 2-methyltetrahydrofuran were charged to a reaction flask equipped with a thermometer. The mixture was stirred with a mechanical upper stirrer under a nitrogen atmosphere. The mixture was than heated to 50° C., kept at that temperature for 15 minutes and then heated further to 60° C. Samples were taken at regular intervals and the reaction progress was monitored using a Bruker Alpha FT-IR spectrometer until no NCO-stretch at 2200-2300 $cm^{-1}$ was observed. The solvent was removed in vacuo to obtain a clear highly viscous liquid. The calculated molecular weight of the theoretical main component was 849.57 Da, chemical structure is shown below.

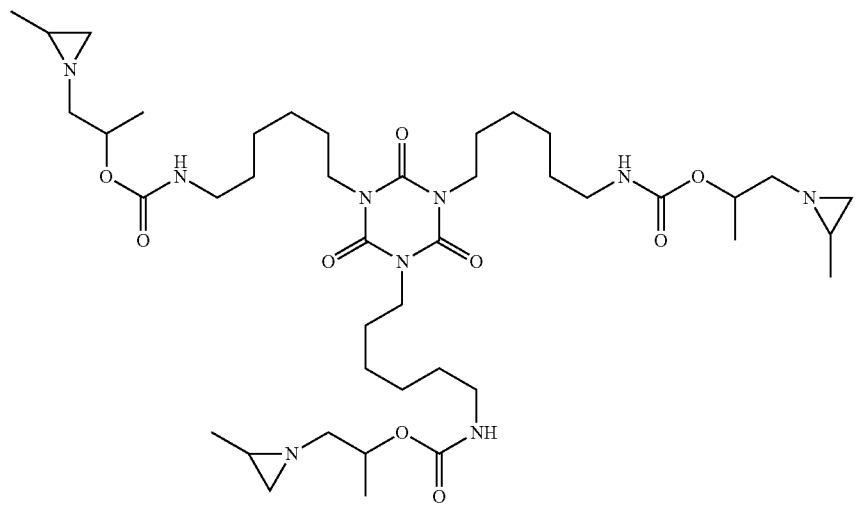 [SMILES: CC(CN1CC1C)OC(=O)NCCCCCCn1c(=O)n(CCCCCCNC(=O)OC(C)CN2CC2C)c(=O)n(CCCCCCNC(=O)OC(C)CN2CC2C)c1=O]

Molecular weight was confirmed by Maldi-TOF-MS: Calcd. [M+Na+]=872.57 Da; Obs. [M+Na+]=872.53 Da. The following components with a mass below 580 Da were determined by LC-MS and quantified:

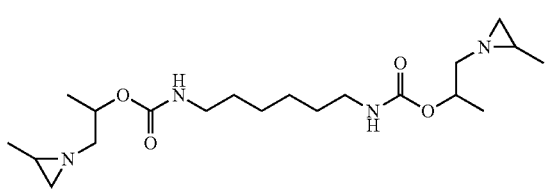

was present in the composition at 0.06 wt. %.

Genotoxicity Test

|  | Without S9 rat liver extract | | | | | | With S9 rat liver extract | | | | | |
|---|---|---|---|---|---|---|---|---|---|---|---|---|
|  | Bscl 2 | | | Rtkn | | | Bscl 2 | | | Rtkn | | |
|  | | | | concentration | | | | | | | | |
|  | 10 | 25 | 50 | 10 | 25 | 50 | 10 | 25 | 50 | 10 | 25 | 50 |
| Composition 16 | 1.2 | 1.3 | 1.3 | 1.2 | 1.2 | 1.4 | 1.2 | 1.3 | 1.2 | 1.2 | 1.1 | 0.9 |

The genotoxicity test results show that the crosslinker composition of Example 16 is non-genotoxic.

Subsequently, 15 grams of the viscous liquid obtained in the previous step was mixed with 7.5 grams of methylethylketone and incubated at 50° C. until a homogeneous solution was obtained. To this solution was added 0.03 grams of triethylamine (TEA) and then 3.0 grams of molten Maxemul™ 7101 dispersant. The resulting mixture was stirred for 5 minutes at room temperature using an IKA T25 Digital Ultra-Turrax® mixer with S 25 N-18G head at 2,000 rpm. Then, stirring was increased to 10,000 rpm and 15 grams of demineralized water, brought to pH 11 using triethylamine, was added gradually to the mixture over 15 minutes. During this addition process, the mixer was moved around the reaction vessel continuously. After completion of the addition, the resulting dispersion was stirred at 5,000 rpm for 10 more minutes, and the pH of the dispersion was set to 11 with TEA.

Functional performance and stability of the crosslinker dispersion were assessed using spot tests on coating surfaces, based on procedures from the DIN 68861-1 standard, and viscosity measurements as well as particle size measurements. For these tests, the crosslinker dispersion was stored in an oven at 50° C. for 4 weeks. Every week, the viscosity and the particle size of the crosslinker dispersion were determined. Additionally, every week, 1.6 grams of the aged crosslinker dispersion was mixed with 21 grams of Polymer P1 under continuous stirring, and the resulting mixture was further stirred for 30 minutes. This coating composition was filtered and applied to Leneta test cards using 100 μm wire rod applicators (Test 16). For reference, films were also cast from the same composition lacking the crosslinker dispersion (Test Blank). The films were dried for 1 hour at 25° C., then annealed at 50° C. for 16 hours. Subsequently, a piece of cotton wool was soaked in 1:1 EtOH:demineralized water and placed on the film for 1 hour. After removal of the EtOH and 60 minutes recovery, the following results were obtained (a score of 1 indicates complete degradation of the film, 5 indicates no damage visible):

Performance and Stability Test

| Sample | Week 0 | Week 1 | Week 2 | Week 3 | Week 4 |
|---|---|---|---|---|---|
| Particle size 16 (nm) | 269 | 204 | 204 | 202 | 209 |
| Viscosity 16 (mPa · s) | 75 | 53 | 60 | 50 | 71 |
| Test 16 | 4 | 4 | 4 | 3 | 3 |
| Test Blank | 1 | 1 | 1 | 1 | 1 |

COMPARATIVE EXAMPLE C7

Crosslinker was Synthesized as Example 16.

Subsequently, 15 grams of the viscous liquid obtained in the previous step was mixed with 15 grams of acetone and incubated at 50° C. until a homogeneous solution was obtained. To this solution was added 15 grams of demineralized water, brought to pH 11 using triethylamine. The resulting mixture, a clear solution with no dispersed phase, was stirred for 30 minutes at room temperature using a three-bladed propeller stirrer with diameter 50 mm at 500 rpm. Finally, the pH of the solution was set to 11 with TEA.

Functional performance and stability of the crosslinker solution were assessed using spot tests on coating surfaces, based on procedures from the DIN 68861-1 standard, and viscosity measurements as well as particle size measurements. For these tests, the crosslinker dispersion was stored in an oven at 50° C. for 4 weeks. Every week, the viscosity and the particle size of the crosslinker dispersion were determined. Additionally, every week, 1.8 grams of the aged crosslinker solution was mixed with 21 grams of Polymer P1 under continuous stirring, and the resulting mixture was further stirred for 30 minutes. This coating composition was filtered and applied to Leneta test cards using 100 μm wire rod applicators (Test C7). For reference, films were also cast from the same composition lacking the crosslinker dispersion (Test Blank). The films were dried for 1 hour at 25° C., then annealed at 50° C. for 16 hours. Subsequently, a piece of cotton wool was soaked in 1:1 EtOH:demineralized water and placed on the film for 1 hour. After removal of the EtOH and 60 minutes recovery, the following results were obtained (a score of 1 indicates complete degradation of the film, 5 indicates no damage visible):

Performance and Stability Test

| Sample | Week 0 | Week 1 | Week 2 | Week 3 | Week 4 |
|---|---|---|---|---|---|
| Particle size C7 (nm) | N/A | N/A | —* | —* | —* |
| Viscosity C7 (mPa · s) | 11 | 10 | —* | —* | —* |
| Test C7 | 5 | 4 | —* | —* | —* |
| Test Blank | 1 | 1 | 1 | 1 | 1 |

*Crosslinker mixture gelled during second week of storage

COMPARATIVE EXAMPLE C8

Crosslinker was Synthesized as Example 16.

Subsequently, 12.4 grams of the highly viscous liquid obtained in the described synthesis was mixed with 10.1 grams of acetone and incubated at 50° C. until a homogeneous solution was obtained. To this solution was added 7.5 grams of demineralized water, brought to pH 10 using triethylamine. The resulting mixture, a clear solution with no dispersed phase, was stirred for 30 minutes at room temperature using a three-bladed propeller stirrer with diameter 50 mm at 500 rpm. Finally, the pH of the solution was set to 10 with TEA.

Functional performance and stability of the crosslinker solution were assessed using spot tests on coating surfaces, based on procedures from the DIN 68861-1 standard, and viscosity measurements as well as particle size measurements. For these tests, the crosslinker dispersion was stored in an oven at 50° C. for 4 weeks. Every week, the viscosity and the particle size of the crosslinker dispersion were determined. Additionally, every week, 1.4 grams of the aged crosslinker solution was mixed with 21 grams of Polymer P1 under continuous stirring, and the resulting mixture was further stirred for 30 minutes. This coating composition was filtered and applied to Leneta test cards using 100 μm wire rod applicators (Test C8). For reference, films were also cast from the same composition lacking the crosslinker dispersion (Test Blank). The films were dried for 1 hour at 25° C., then annealed at 50° C. for 16 hours. Subsequently, a piece of cotton wool was soaked in 1:1 EtOH:demineralized water and placed on the film for 1 hour. After removal of the EtOH and 60 minutes recovery, the following results were obtained (a score of 1 indicates complete degradation of the film, 5 indicates no damage visible):

Performance and Stability Test

| Sample | Week 0 | Week 1 | Week 2 | Week 3 | Week 4 |
|---|---|---|---|---|---|
| Particle size C8 (nm) | N/A | —* | —* | —* | —* |
| Viscosity C8 (mPa · s) | 8 | —* | —* | —* | —* |
| Test C8 | 4 | —* | —* | —* | —* |
| Test Blank | 1 | 1 | 1 | 1 | 1 |

*Crosslinker mixture gelled during first week of storage

EXAMPLE 17

Crosslinker was Synthesized as Example 16.

Subsequently, 15 grams of the viscous liquid obtained in the previous step was mixed with 5.0 grams of methylethylketone (MEK) and incubated at 50° C. until a homogeneous solution was obtained. To this solution was added 0.03 grams of triethylamine (TEA) and then 3.0 grams of molten Pluronic® PE6800 dispersant. The resulting mixture was stirred for 5 minutes at room temperature using an IKA T25 Digital Ultra-Turrax® mixer with S 25 N-18G head at 2,000 rpm. Then, stirring was increased to 10,000 rpm and 15 grams of demineralized water, brought to pH 11 using triethylamine, was added gradually to the mixture over 15 minutes. During this addition process, the mixer was moved around the reaction vessel continuously. After completion of the addition, the resulting dispersion was stirred at 5,000 rpm for 10 more minutes, and the pH of the dispersion was set to 11 with TEA.

Functional performance and stability of the crosslinker dispersion were assessed as in Example 16.

Performance and Stability Test

| Sample | Week 0 | Week 1 | Week 2 | Week 3 | Week 4 |
|---|---|---|---|---|---|
| Particle size 17 (nm) | 500 | 408 | 412 | 472 | 490 |
| Viscosity 17 (mPa · s) | 638 | 640 | 574 | 594 | 595 |
| Test 17 | 5 | 5 | 5 | 5 | 4 |
| Test Blank | 1 | 1 | 1 | 1 | 1 |

EXAMPLE 18

A 1 L round bottom flask equipped with a condensor was placed under a $N_2$ atmosphere and charged with propylene imine (80.0 gram), n-butyl glycidyl ether (126.0 gram) and $K_2CO_3$ (10.00 gram) and heated to 80° C. in 30 min, after which the mixture was stirred for 21 h at T=80° C. After filtration the excess of PI was removed in vacuo, followed by further purification via vacuum distillation, resulting in a colorless low viscous liquid.

46.54 grams of the resulting material (1-butoxy-3-(2-methylaziridin-1-yl)propan-2-ol) and 28.63 grams of 1-(2-methylaziridin-1-yl)propan-2-ol were charged to a reaction flask equipped with a thermometer, together with 0.02 grams of bismuth neodecanoate and 32.54 grams of 2-methyltetrahydrofuran. The mixture was stirred with a mechanical upper stirrer under a nitrogen atmosphere and heated to 50° C. A solution of 100 grams of Desmodur N 3600 in 32.54 grams of 2-methyltetrahydrofuran was then added dropwise in 45 minutes to the reaction flask, a further 10 grams of 2-methyltetrahydrofuran was flushed through the feeding funnel into the reaction mixture, whereafter the mixture was heated further to 70° C. Samples were taken at regular intervals and the reaction progress was monitored using a Bruker Alpha FT-IR spectrometer until no NCO-stretch at 2200-2300 cm$^{-1}$ was observed. The solvent was removed in vacuo to obtain a yellowish highly viscous liquid. The calculated molecular weights of the theoretical main components were 849.57 Da (three methyl side groups), 921.63 Da (two methyl side groups, one butoxymethyl side group), 993.68 Da (one methyl side group, two butoxymethyl side groups) and 1065.74 Da (three butoxymethyl side groups), chemical structures are shown below.

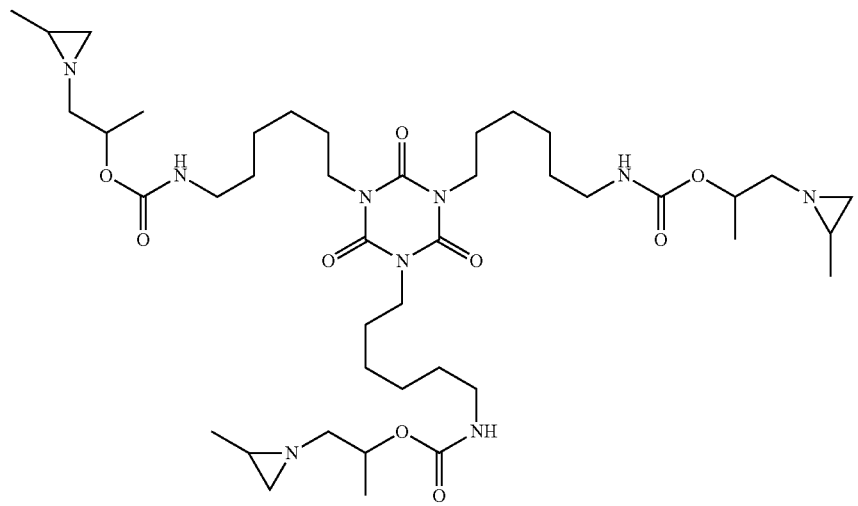 [SMILES: CC(CN1CC1C)OC(=O)NCCCCCCn1c(=O)n(CCCCCCNC(=O)OC(C)CN2CC2C)c(=O)n(CCCCCCNC(=O)OC(C)CN2CC2C)c1=O]

Molecular weight was confirmed by Maldi-TOF-MS:
Calcd. [M+Na+]=872.57 Da; Obs. [M+Na+]=872.59 Da.
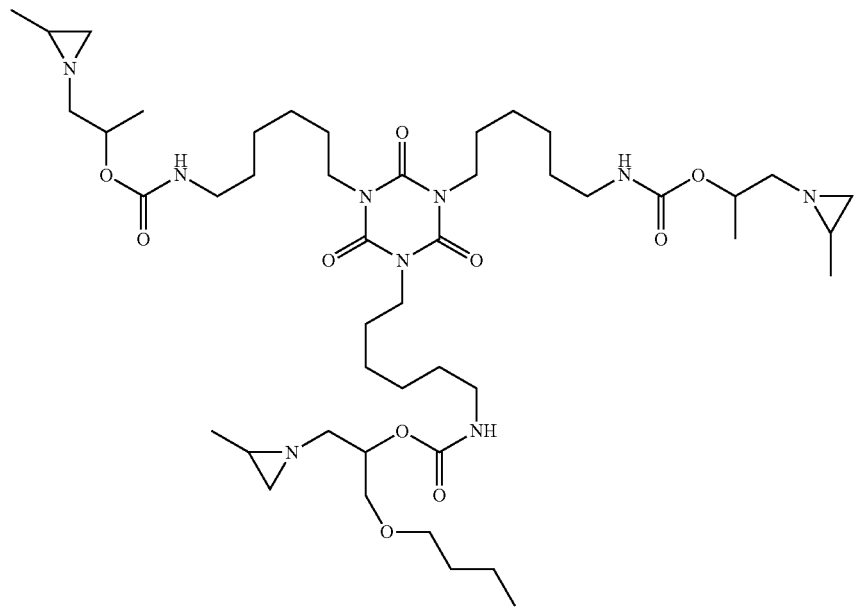 [SMILES: CCCCOCC(CN1CC1C)OC(=O)NCCCCCCn1c(=O)n(CCCCCCNC(=O)OC(C)CN2CC2C)c(=O)n(CCCCCCNC(=O)OC(C)CN2CC2C)c1=O]
Molecular weight was confirmed by Maldi-TOF-MS:
Calcd. [M+Na+]=944.63 Da; Obs. [M+Na+]=944.66 Da.
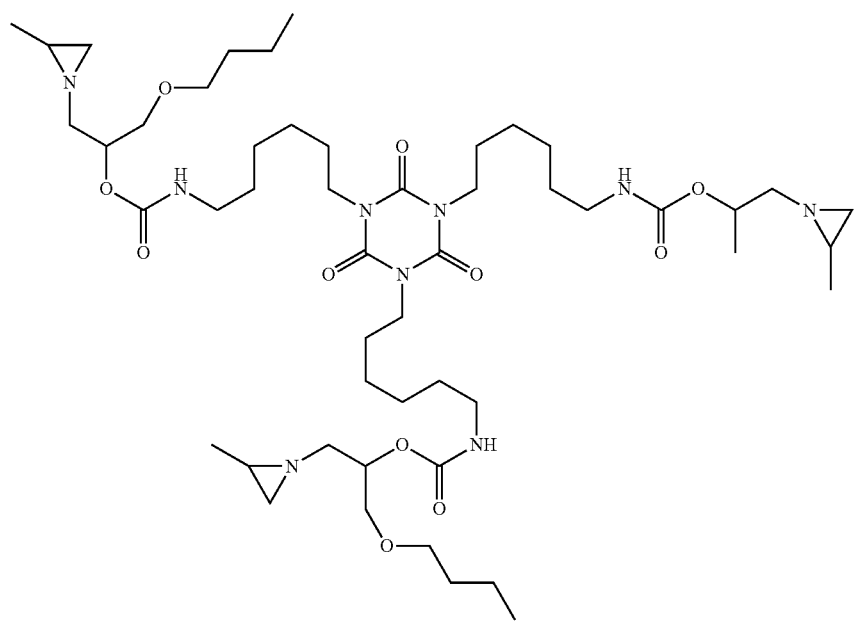 [SMILES: CCCCOCC(CN1CC1C)OC(=O)NCCCCCCn1c(=O)n(CCCCCCNC(=O)OC(C)CN2CC2C)c(=O)n(CCCCCCNC(=O)OC(COCCCC)CN2CC2C)c1=O]

Molecular weight was confirmed by Maldi-TOF-MS: Calcd. [M+Na+]=1016.68 Da; Obs. [M+Na+]=1016.72 Da.

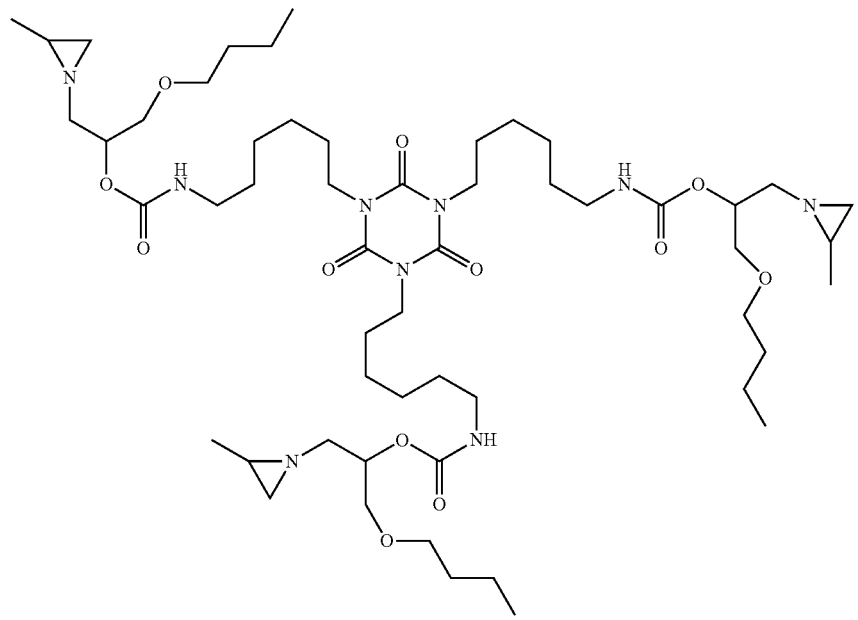 [SMILES: CCCCOCC(CN1CC1C)OC(=O)NCCCCCCn1c(=O)n(CCCCCCNC(=O)OC(COCCCC)CN2CC2C)c(=O)n(CCCCCCNC(=O)OC(COCCCC)CN2CC2C)c1=O]

Molecular weight was confirmed by Maldi-TOF-MS: Calcd. [M+Na+]=1088.74 Da; Obs. [M+Na+]=1088.79 Da.

Subsequently, 15 grams of the viscous liquid obtained in the previous step was mixed with 7.5 grams of acetone and incubated at 50° C. until a homogeneous solution was obtained. To this solution was added 0.03 grams of triethylamine (TEA) and then 1.5 grams of molten Maxemul™ 7101 dispersant. The resulting mixture was stirred for 5 minutes at room temperature using an IKA T25 Digital Ultra-Turrax® mixer with S 25 N-18G head at 2,000 rpm. Then, stirring was increased to 10,000 rpm and 15 grams of demineralized water, brought to pH 11 using triethylamine, was added gradually to the mixture over 15 minutes. During this addition process, the mixer was moved around the reaction vessel continuously. After completion of the addition, the resulting dispersion was stirred at 5,000 rpm for 10 more minutes, and the pH of the dispersion was set to 11 with TEA.

Functional performance and stability of the crosslinker dispersion were assessed using spot tests on coating surfaces, based on procedures from the DIN 68861-1 standard, and viscosity measurements as well as particle size measurements. For these tests, the crosslinker dispersion was stored in an oven at 50° C. for 4 weeks. Every week, the viscosity and the particle size of the crosslinker dispersion were determined. Additionally, every week, 1.8 grams of the aged crosslinker dispersion was mixed with 21 grams of Polymer P1 under continuous stirring, and the resulting mixture was further stirred for 30 minutes. This coating composition was filtered and applied to Leneta test cards using 100 μm wire rod applicators (Test 18). For reference, films were also cast from the same composition lacking the crosslinker dispersion (Test Blank). The films were dried for 1 hour at 25° C., then annealed at 50° C. for 16 hours. Subsequently, a piece of cotton wool was soaked in 1:1 EtOH:demineralized water and placed on the film for 1 hour. After removal of the EtOH and 60 minutes recovery, the following results were obtained (a score of 1 indicates complete degradation of the film, 5 indicates no damage visible):

Performance and Stability Test

| Sample | Week 0 | Week 1 | Week 2 | Week 3 | Week 4 |
|---|---|---|---|---|---|
| Particle size 18 (nm) | 234 | 206 | 237 | 220 | 674 |
| Viscosity 18 (mPa · s) | 138 | 167 | 140 | 104 | 142 |
| Test 18 | 4 | 4 | 4 | 4 | 4 |
| Test Blank | 1 | 1 | 1 | 1 | 1 |

COMPARATIVE EXAMPLE C9

13.6 grams of 1-(2-hydroxyethyl)ethyleneimine was charged to a reaction flask equipped with a thermometer, together with 0.02 grams of bismuth neodecanoate and 147 grams of dimethylformamide. The mixture was stirred with a mechanical upper stirrer under a nitrogen atmosphere and heated to 50° C. A solution of 40.0 grams of Vestanat T1890/100 in 147 grams of dimethylformamide was then added dropwise in 45 minutes to the reaction flask, followed by flushing with a further 10.0 grams of dimethylformamide, whereafter the mixture was heated further to 70° C. Samples were taken at regular intervals and the reaction progress was monitored using a Bruker Alpha FT-IR spectrometer until no NCO-stretch at 2200-2300 cm$^{-1}$ was observed. The solvent was removed in vacuo to obtain a whitish solid. The calculated molecular weight of the theoretical main component was 927.62 Da, chemical structure is shown below.

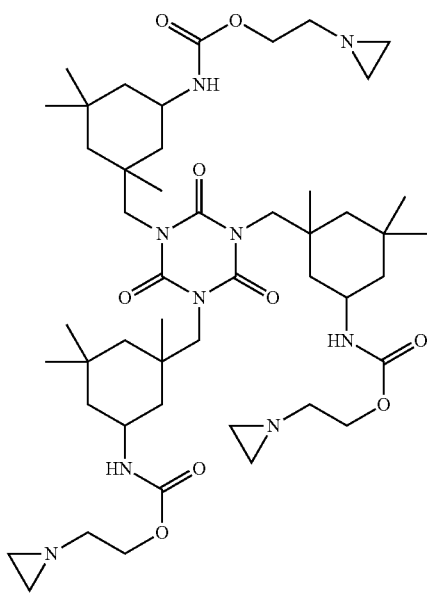 [SMILES: CC1(C)CC(NC(=O)OCCN2CC2)CC(C)(Cn2c(=O)n(CC3(C)CC(NC(=O)OCCN4CC4)CC(C)(C)C3)c(=O)n(CC3(C)CC(NC(=O)OCCN4CC4)CC(C)(C)C3)c2=O)C1]

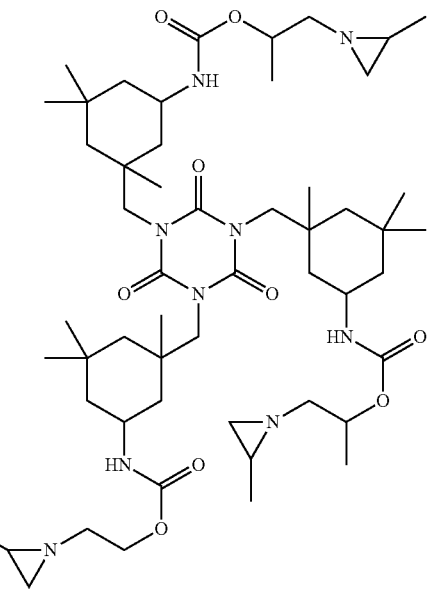

Molecular weight was confirmed by Maldi-TOF-MS: Calcd. [M+Na+]=950.61 Da; Obs. [M+Na+]=950.50 Da.

Subsequently, 15 grams of the whitish solid obtained in the previous step was mixed with 7.5 grams of acetone and incubated at 50° C. until a homogeneous solution was obtained. To this solution was added 0.03 grams of triethylamine (TEA) and then 1.5 grams of molten Maxemul™ 7101 dispersant. The resulting mixture was stirred for 5 minutes at room temperature using an IKA T25 Digital Ultra-Turrax® mixer with S 25 N-18G head at 2,000 rpm. Then, stirring was increased to 10,000 rpm and 15 grams of demineralized water, brought to pH 11 using triethylamine, was added gradually to the mixture over 15 minutes. During this addition process, the mixer was moved around the reaction vessel continuously. After completion of the addition, the resulting dispersion was stirred at 5,000 rpm for 10 more minutes, and the pH of the dispersion was set to 11 with TEA. Within 2 hours after conclusion of this 1-(2-hydroxyethyl)ethyleneimine based preparation, the resulting dispersion had coagulated indicating an unstable crosslinker system and insufficient shelf life.

EXAMPLE 19

15.6 grams of 1-(2-methylaziridin-1-yl)propan-2-ol was charged to a reaction flask equipped with a thermometer, together with 0.02 grams of bismuth neodecanoate and 81.4 grams of dimethylformamide. The mixture was stirred with a mechanical upper stirrer under a nitrogen atmosphere and heated to 50° C. A solution of 34.5 grams of Vestanat T1890/100 in 200 grams of dimethylformamide was then added dropwise in 45 minutes to the reaction flask, whereafter the mixture was heated further to 70° C. Samples were taken at regular intervals and the reaction progress was monitored using a Bruker Alpha FT-IR spectrometer until no NCO-stretch at 2200-2300 cm$^{-1}$ was observed. The solvent was removed in vacuo to obtain a whitish solid. The calculated molecular weight of the theoretical main component was 1011.71 Da, chemical structure is shown below.

Molecular weight was confirmed by Maldi-TOF-MS: Calcd. [M+Na+]=1034.70 Da; Obs. [M+Na+]=1034.66 Da.

Subsequently, 15 grams of the whitish solid obtained in the previous step was mixed with 7.5 grams of acetone and incubated at 50° C. until a homogeneous solution was obtained. To this solution was added 0.03 grams of triethylamine (TEA) and then 1.5 grams of molten Maxemul™ 7101 dispersant. The resulting mixture was stirred for 5 minutes at room temperature using an IKA T25 Digital Ultra-Turrax® mixer with S 25 N-18G head at 2,000 rpm. Then, stirring was increased to 10,000 rpm and 15 grams of demineralized water, brought to pH 11 using triethylamine, was added gradually to the mixture over 15 minutes. During this addition process, the mixer was moved around the reaction vessel continuously. After completion of the addition, the resulting dispersion was stirred at 5,000 rpm for 10 more minutes, and the pH of the dispersion was set to 11 with TEA.

Functional performance and stability of the crosslinker dispersion were assessed using spot tests on coating surfaces, based on procedures from the DIN 68861-1 standard, and viscosity measurements as well as particle size measurements. For these tests, the crosslinker dispersion was stored in an oven at 50° C. for 4 weeks. Every week, the viscosity and the particle size of the crosslinker dispersion were determined. Additionally, every week, 2.6 grams of the aged crosslinker dispersion was mixed with 21 grams of Polymer P1 under continuous stirring, and the resulting mixture was further stirred for 30 minutes. This coating composition was filtered and applied to Leneta test cards using 100 μm wire rod applicators (Test 19). For reference, films were also cast from the same composition lacking the crosslinker dispersion (Test Blank). The films were dried for 1 hour at 25° C., then annealed at 50° C. for 16 hours. Subsequently, a piece of cotton wool was soaked in 1:1 EtOH:demineralized water and placed on the film for 1 hour. After removal of the EtOH and 60 minutes recovery, the following results were obtained (a score of 1 indicates complete degradation of the film, 5 indicates no damage visible):

Performance and Stability Test

| Sample | Week 0 | Week 1 | Week 2 | Week 3 | Week 4 |
|---|---|---|---|---|---|
| Particle size 19 (nm) | 370 | 396 | 445 | 392 | 422 |
| Viscosity 19 (mPa · s) | 169 | 179 | 200 | 220 | 235 |
| Test 19 | 4 | 4 | 4 | 4 | 4 |
| Test Blank | 1 | 1 | 1 | 1 | 1 |

EXAMPLE 20

A 1 L round bottom flask equipped with a condensor was placed under a $N_2$ atmosphere and charged with propylene imine (80 gram), n-butyl glycidyl ether (126.0 gram) and $K_2CO_3$ (10.00 gram) and heated to 80° C. in 30 min, after which the mixture was stirred for 21 h at T=80° C. After filtration the excess of PI was removed in vacuo, followed by further purification via vacuum distillation, resulting in a colorless low viscous liquid. 22.0 grams of the resulting material (1-butoxy-3-(2-methylaziridin-1-yl)propan-2-ol) was charged to a reaction flask equipped with a thermometer, together with 0.02 grams of bismuth neodecanoate and 70.8 grams of 2-methyltetrahydrofuran. The mixture was stirred with a mechanical upper stirrer under a nitrogen atmosphere and heated to 50° C. A solution of 30.0 grams of Vestanat T1890/100 in 177 grams of 2-methyltetrahydrofuran was then added dropwise in 45 minutes to the reaction flask, whereafter the mixture was heated further to 70° C. Samples were taken at regular intervals and the reaction progress was monitored using a Bruker Alpha FT-IR spectrometer until no NCO-stretch at 2200-2300 $cm^{-1}$ was observed. The solvent was removed in vacuo to obtain a whitish solid. The calculated molecular weight of the theoretical main component was 1227.88 Da, chemical structure is shown below.

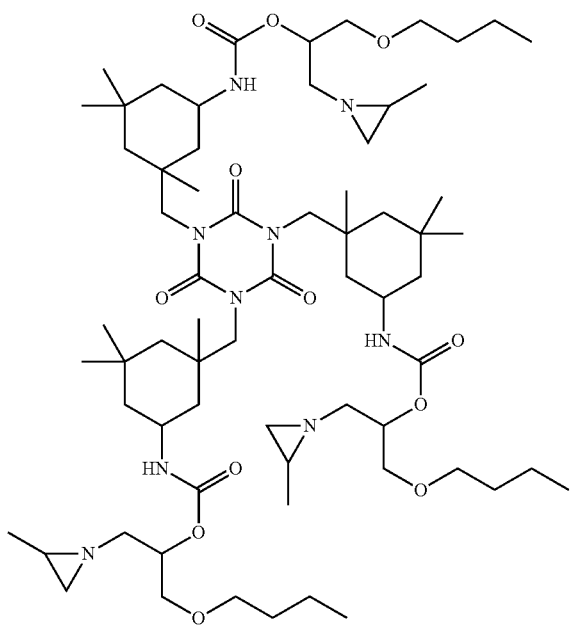 [SMILES: CCCCOCC(CN1CC1C)OC(=O)NC1CC(C)(C)CC(C)(Cn2c(=O)n(CC3(C)CC(NC(=O)OC(COCCCC)CN4CC4C)CC(C)(C)C3)c(=O)n(CC3(C)CC(NC(=O)OC(COCCCC)CN4CC4C)CC(C)(C)C3)c2=O)C1]

Subsequently, 15 grams of the whitish solid obtained in the previous step was mixed with 7.5 grams of acetone and incubated at 50° C. until a homogeneous solution was obtained. To this solution was added 0.03 grams of triethylamine (TEA) and then 1.5 grams of molten Maxemul™ 7101 dispersant. The resulting mixture was stirred for 5 minutes at room temperature using an IKA T25 Digital Ultra-Turrax® mixer with S 25 N-18G head at 2,000 rpm. Then, stirring was increased to 10,000 rpm and 15 grams of demineralized water, brought to pH 11 using triethylamine, was added gradually to the mixture over 15 minutes. During this addition process, the mixer was moved around the reaction vessel continuously. After completion of the addition, the resulting dispersion was stirred at 5,000 rpm for 10 more minutes, and the pH of the dispersion was set to 11 with TEA.

Functional performance and stability of the crosslinker dispersion were assessed using spot tests on coating surfaces, based on procedures from the DIN 68861-1 standard, and viscosity measurements as well as particle size measurements. For these tests, the crosslinker dispersion was stored in an oven at 50° C. for 4 weeks. Every week, the viscosity and the particle size of the crosslinker dispersion were determined. Additionally, every week, 3.0 grams of the aged crosslinker dispersion was mixed with 21 grams of Polymer P1 under continuous stirring, and the resulting mixture was further stirred for 30 minutes. This coating composition was filtered and applied to Leneta test cards using 100 µm wire rod applicators (Test 20). For reference, films were also cast from the same composition lacking the crosslinker dispersion (Test Blank). The films were dried for 1 hour at 25° C., then annealed at 50° C. for 16 hours. Subsequently, a piece of cotton wool was soaked in 1:1 EtOH:demineralized water and placed on the film for 1 hour. After removal of the EtOH and 60 minutes recovery, the following results were obtained (a score of 1 indicates complete degradation of the film, 5 indicates no damage visible):

Performance and Stability Test

| Sample | Week 0 | Week 1 | Week 2 | Week 3 | Week 4 |
|---|---|---|---|---|---|
| Particle size 20 (nm) | 208 | 196 | 200 | 193 | 189 |
| Viscosity 20 (mPa · s) | 91 | 107 | 85 | 140 | 132 |
| Test 20 | 4 | 4 | 4 | 4 | 4 |
| Test Blank | 1 | 1 | 1 | 1 | 1 |

EXAMPLE 21

The (1-butoxy-3-(2-methylaziridin-1-yl)propan-2-ol) intermediate was prepared as described in Example 1, and 32.8 grams were charged to a feed vessel. Subsequently, 8.30 grams of 1-methoxy-2-propyl acetate (MPA) were added to the feed vessel, and the contents homogenized by stirring. Separately, 45.0 grams of Desmodur N3600 were placed in a reaction flask equipped with a thermometer, together with 0.02 grams of bismuth neodecanoate and 8.30 grams of MPA. This mixture was stirred with a mechanical upper stirrer under a nitrogen atmosphere and heated to 50° C. The solution in the feed vessel was then added dropwise in 45 minutes to the reaction flask, whereafter the mixture was kept at 50° C. Samples were taken at regular intervals and the reaction progress was monitored using a Bruker Alpha FT-IR spectrometer until no change in NCO-stretch at 2200-2300 $cm^{-1}$ was observed. Subsequently, a solution of 24.3 grams of a poly(ethylene glycol) monomethyl ether with an average Mn of 500 Da in 8.30 grams of MPA was added to the mixture in 15 minutes, and afterwards the temperature of the mixture was increased to 80° C. The reaction mixture was then further reacted to complete disappearance of aforementioned NCO-stretch peak. The solvent was removed in vacuo to obtain a clear yellowish viscous liquid. The calculated molecular weights of the theoretical main components were 1065.74 Da (three aziridines), 1394.90 Da (two aziridines, 11 EG repeating units), 1438.92 Da (two aziridines, 12 EG repeating units) and 1482.95 Da (two aziridines, 13 EG repeating units), chemical structures are shown below.

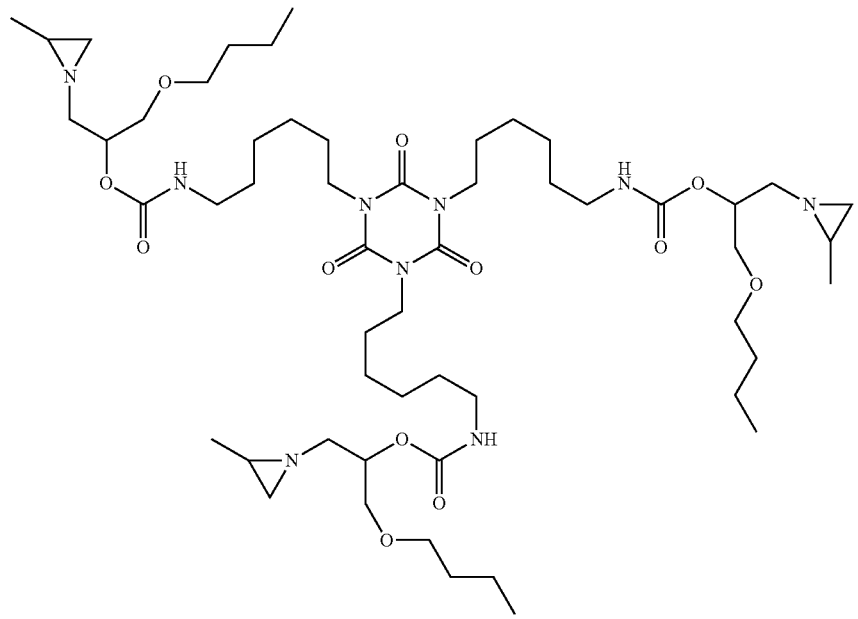

Molecular weight was confirmed by Maldi-TOF-MS: Calcd. [M+Na+]=1088.74 Da; Obs. [M+Na+]=1088.67 Da.

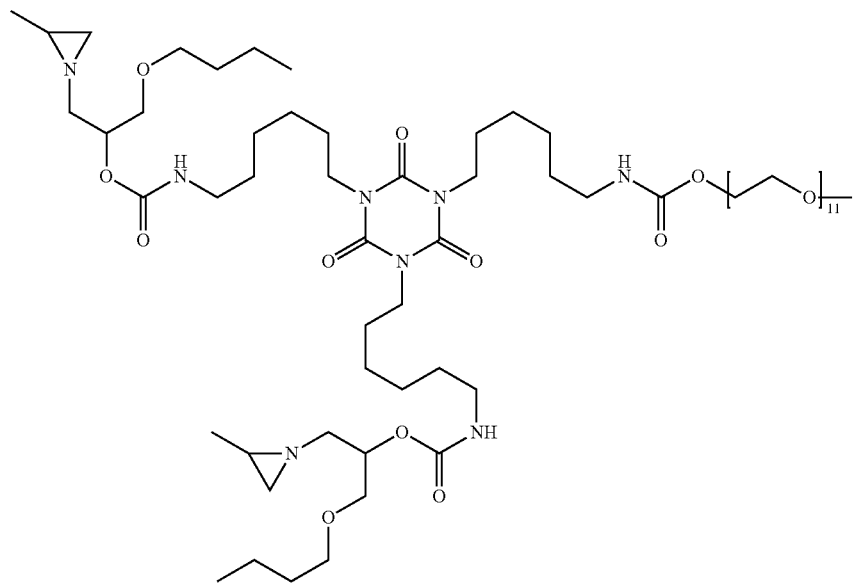

Molecular weight was confirmed by Maldi-TOF-MS:
Calcd. [M+Na+]=1417.90 Da; Obs. [M+Na+]=1417.81 Da.
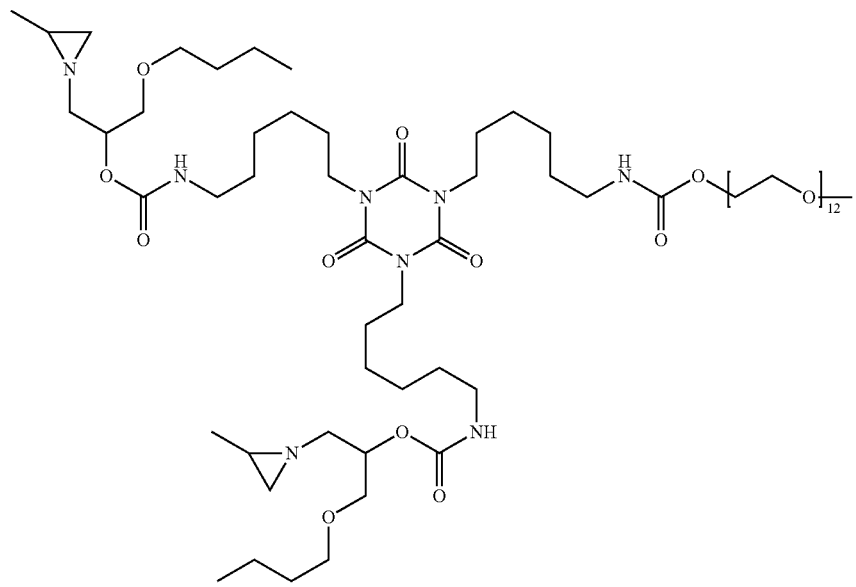
Molecular weight was confirmed by Maldi-TOF-MS:
Calcd. [M+Na+]=1461.92 Da; Obs. [M+Na+]=1461.84 Da.
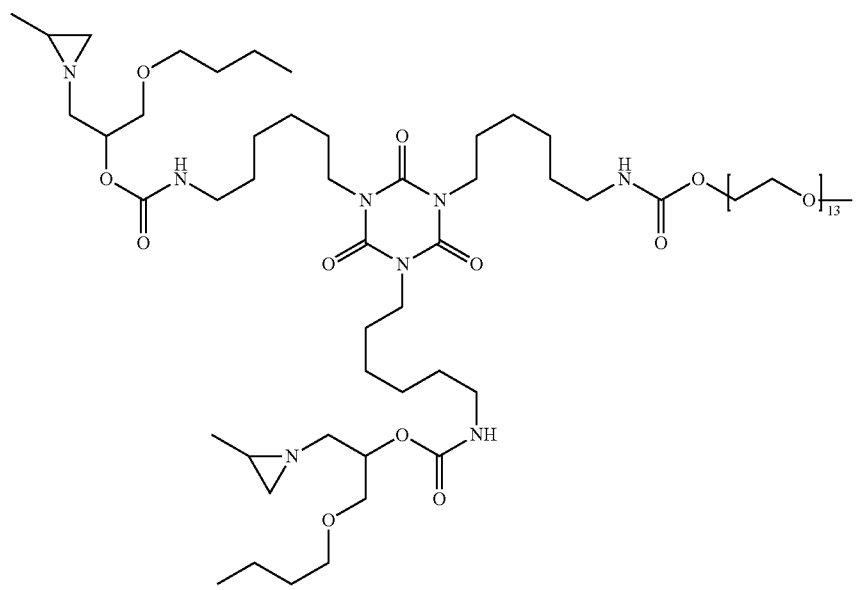
Molecular weight was confirmed by Maldi-TOF-MS:
Calcd. [M+Na+]=1505.95 Da; Obs. [M+Na+]=1505.86 Da.
The following components with a mass below 580 Da were determined by LC-MS and quantified:

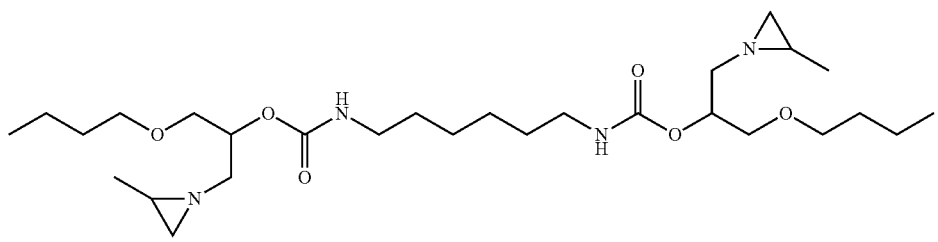 [SMILES: CCCCOCC(CN1CC1C)OC(=O)NCCCCCCNC(=O)OC(COCCCC)CN1CC1C]

was present in the composition at 0.04 wt. % and

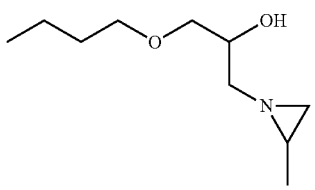

was present at 0.05 wt. %.

Genotoxicity Test

|  | Without S9 rat liver extract | | | | | | With S9 rat liver extract | | | | | |
| --- | --- | --- | --- | --- | --- | --- | --- | --- | --- | --- | --- | --- |
|  | Bscl 2 | | | Rtkn | | | Bscl 2 | | | Rtkn | | |
|  | concentration | | | | | | | | | | | |
|  | 10 | 25 | 50 | 10 | 25 | 50 | 10 | 25 | 50 | 10 | 25 | 50 |
| Composition 21 | 1.0 | 1.1 | 1.2 | 0.9 | 0.9 | 0.7 | 1.1 | 1.2 | 1.3 | 0.9 | 0.8 | 0.7 |

The genotoxicity test results show that the crosslinker composition of Example 21 is non-genotoxic.

Subsequently, 94 grams of the viscous liquid obtained in the previous step was placed in a cylindrical 300 mL reactor with corresponding helical stirrer and stirred at 120 rpm at 50° C. To the reactor was added 0.03 grams of triethylamine (TEA) and then 3.0 grams of molten Maxemul™ 7101 dispersant, followed by stirring until a homogeneous mixture was obtained. Then, 10.8 grams of demineralized water, brought to pH 11 using triethylamine, was added to the mixture and it was stirred for 1 hour. Subsequently a further 141.7 grams of demineralized water, brought to pH 11 using triethylamine, was added over 70 minutes and the pH of the dispersion was set to 11 with TEA. Then, 45 grams of the resulting dispersion was stirred at room temperature using an IKA T25 Digital Ultra-Turrax® mixer with S 25 N-18G head at 5,000 rpm. Under continuous stirring, a solution of 3.0 grams of sodium lauryl sulphate (SLS) in 7.0 grams of demineralized water was added dropwise. During this addition process, the mixer was moved around the reaction vessel continuously. After completion of the addition, the resulting dispersion was stirred at 5,000 rpm for 10 more minutes.

Functional performance and stability of the crosslinker dispersion were assessed using spot tests on coating surfaces, based on procedures from the DIN 68861-1 standard, and viscosity measurements as well as particle size measurements. For these tests, the crosslinker dispersion was stored in an oven at 50° C. for 4 weeks. Every week, the viscosity and the particle size of the crosslinker dispersion were determined. Additionally, every week, 3.1 grams of the aged crosslinker dispersion was mixed with 21 grams of Polymer P1 under continuous stirring, and the resulting mixture was further stirred for 30 minutes. This coating composition was filtered and applied to Leneta test cards using 100 μm wire rod applicators (Test 21). For reference, films were also cast from the same composition lacking the crosslinker dispersion (Test Blank). The films were dried for 1 hour at 25° C., then annealed at 50° C. for 16 hours. Subsequently, a piece of cotton wool was soaked in 1:1 EtOH:demineralized water and placed on the film for 1 hour. After removal of the EtOH and 60 minutes recovery, the following results were obtained (a score of 1 indicates complete degradation of the film, 5 indicates no damage visible):

Performance and Stability Test

| Sample | Week 0 | Week 1 | Week 2 | Week 3 | Week 4 |
| --- | --- | --- | --- | --- | --- |
| Particle size 21 (nm) | 27 | 22 | 22 | 21 | 21 |
| Viscosity 21 (mPa · s) | 912 | 680 | 755 | 752 | 774 |
| Test 21 | 4 | 4 | 4 | 4 | 3 |
| Test Blank | 1 | 1 | 1 | 1 | 1 |

EXAMPLE 22

A 1 L round bottom flask equipped with a condensor was placed under a $N_2$ atmosphere and charged with propylene imine (80.0 gram), n-butyl glycidyl ether (126.0 gram) and $K_2CO_3$ (10.00 gram) and heated to 80° C. in 30 min, after which the mixture was stirred for 21 h at T=80° C. After filtration the excess of PI was removed in vacuo, followed by further purification via vacuum distillation, resulting in a colorless low viscous liquid.

130 grams of Desmodur N 3600 was charged to a reaction flask equipped with a thermometer, together with 0.02 grams of bismuth neodecanoate. The mixture was stirred with a mechanical upper stirrer under a nitrogen atmosphere and heated to 50° C. 94.7 grams of the mixture from the previous step was then added dropwise in 10 minutes to the reaction flask, whereafter the mixture was heated further to 70° C. and that temperature maintained for 90 minutes. Subsequently, 141.2 grams of Jeffamine XTJ-436 was added dropwise in 25 minutes to the reaction vessel. Samples were taken at regular intervals and the reaction progress was monitored using a Bruker Alpha FT-IR spectrometer until no change in NCO-stretch at 2200-2300 $cm^{-1}$ was observed.

Subsequently, 4.16 grams of 1-butanol were added to the mixture, followed by further reaction to complete disappearance of aforementioned NCO-stretch peak. The product was a highly viscous yellowish translucent liquid. The calculated molecular weights of the theoretical main components were 1065.74 Da (three aziridines), 1852.33 Da (two aziridines, 13 PG repeating units) and 1910.37 Da (two aziridines, 14 PG repeating units), chemical structures are shown below.

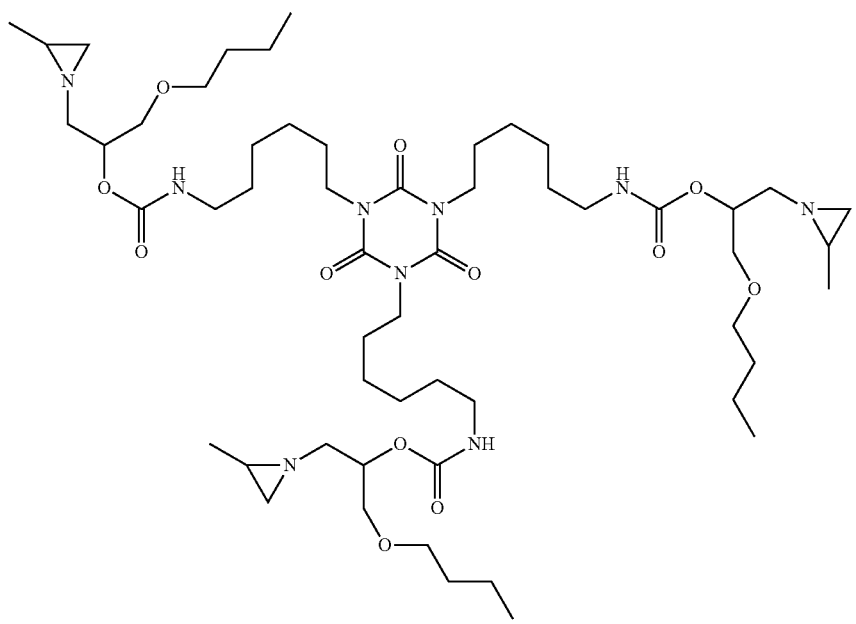
Molecular weight was confirmed by Maldi-TOF-MS: Calcd. [M+Na+]=1088.74 Da; Obs. [M+Na+]=1089.03 Da.
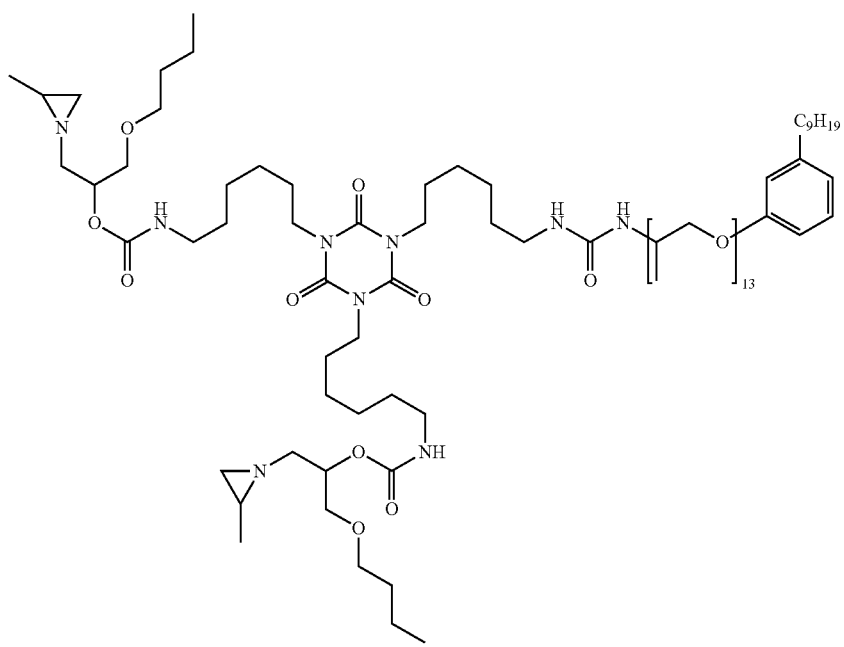

Molecular weight was confirmed by Maldi-TOF-MS: Calcd. [M+Na+]=1875.33 Da; Obs. [M+Na+]=1875.31 Da.

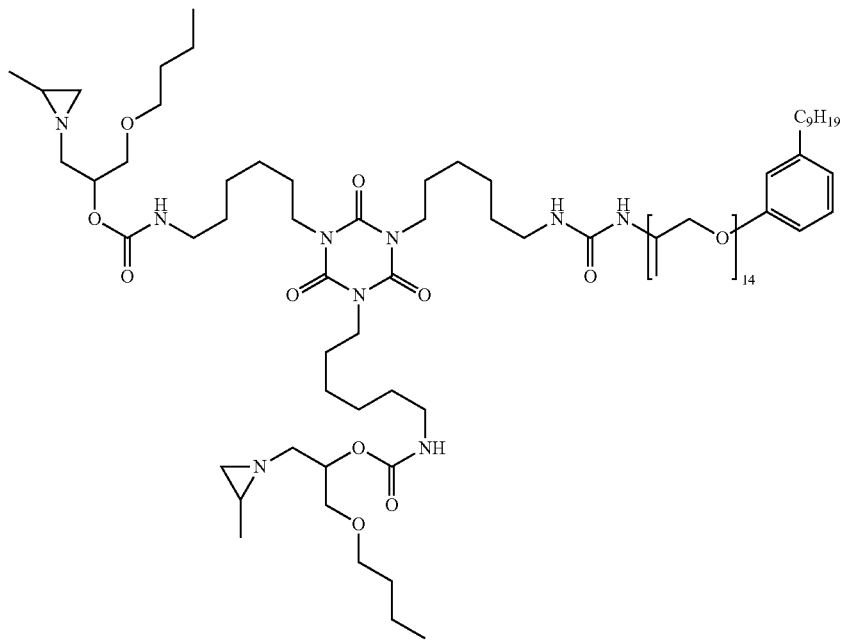

Molecular weight was confirmed by Maldi-TOF-MS: Calcd. [M+Na+]=1933.37 Da; Obs. [M+Na+]=1933.30 Da.

Subsequently, 15 grams of the viscous liquid obtained in the previous step was mixed with 7.5 grams of acetone and incubated at 50° C. until a homogeneous solution was obtained. To this solution was added 0.03 grams of triethylamine (TEA) and then 1.5 grams of molten Maxemul™ 7101 dispersant. The resulting mixture was stirred for 5 minutes at room temperature using an IKA T25 Digital Ultra-Turrax® mixer with S 25 N-18G head at 2,000 rpm. Then, stirring was increased to 10,000 rpm and 15 grams of demineralized water, brought to pH 11 using triethylamine, was added gradually to the mixture over 15 minutes. During this addition process, the mixer was moved around the reaction vessel continuously. After completion of the addition, the resulting dispersion was stirred at 5,000 rpm for 10 more minutes, and the pH of the dispersion was set to 11 with TEA.

Functional performance and stability of the crosslinker dispersion were assessed using spot tests on coating surfaces, based on procedures from the DIN 68861-1 standard, and viscosity measurements as well as particle size measurements. For these tests, the crosslinker dispersion was stored in an oven at 50° C. for 4 weeks. Every week, the viscosity and the particle size of the crosslinker dispersion were determined. Additionally, every week, 4.0 grams of the aged crosslinker dispersion was mixed with 21 grams of Polymer P1 under continuous stirring, and the resulting mixture was further stirred for 30 minutes. This coating composition was filtered and applied to Leneta test cards using 100 μm wire rod applicators (Test 22). For reference, films were also cast from the same composition lacking the crosslinker dispersion (Test Blank). The films were dried for 1 hour at 25° C., then annealed at 50° C. for 16 hours. Subsequently, a piece of cotton wool was soaked in 1:1 EtOH:demineralized water and placed on the film for 1 hour. After removal of the EtOH and 60 minutes recovery, the following results were obtained (a score of 1 indicates complete degradation of the film, 5 indicates no damage visible):

Performance and Stability Test

| Sample | Week 0 | Week 1 | Week 2 | Week 3 | Week 4 |
| --- | --- | --- | --- | --- | --- |
| Particle size 22 (nm) | 208 | 182 | n.d. | 176 | 178 |
| Viscosity 22 (mPa · s) | 97 | 84 | n.d. | 85 | 100 |
| Test 22 | 4 | 4 | n.d. | 3 | 3 |
| Test Blank | 1 | 1 | n.d. | 1 | 1 |

EXAMPLE 23

A 1 L round bottom flask equipped with a condensor was placed under a $N_2$ atmosphere and charged with propylene imine (91.0 gram), 2-ethylhexylglycidyl ether (201.0 gram) and $K_2CO_3$ (10.00 gram) and heated to 80° C., after which the mixture was stirred for 47 h at T=80° C. After filtration the excess of PI was removed in vacuo, followed by further purification via vacuum distillation, resulting in a colorless low viscous liquid.

130 grams of the resulting material was charged to a reaction flask equipped with a thermometer, together with 0.02 grams of bismuth neodecanoate and 668 grams of dimethylformamide. The mixture was stirred with a mechanical upper stirrer under a nitrogen atmosphere and heated to 50° C. A solution of 107.4 grams of Desmodur N 3600 in 668 grams of dimethylformamide was then added dropwise in 45 minutes to the reaction flask, a further 10 grams of dimethylformamide was flushed through the feeding funnel into the reaction mixture, whereafter the mixture was heated further to 75° C. Samples were taken at regular intervals and the reaction progress was monitored using a Bruker Alpha FT-IR spectrometer until no NCO-stretch at 2200-2300 $cm^{-1}$ was observed. The solvent was removed in vacuo to obtain a highly viscous colorless liquid. The calculated molecular weight of the theoretical main component was 1233.93 Da, chemical structure is shown below.

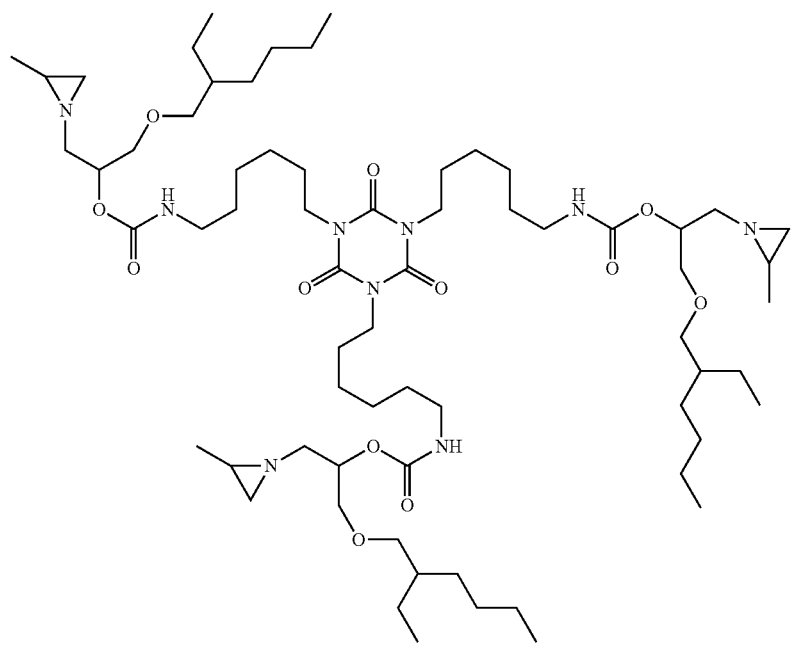 [SMILES: CCCCC(CC)COCC(CN1CC1C)OC(=O)NCCCCCCn1c(=O)n(CCCCCCNC(=O)OC(COCC(CC)CCCC)CN2CC2C)c(=O)n(CCCCCCNC(=O)OC(COCC(CC)CCCC)CN2CC2C)c1=O]

Molecular weight was confirmed by Maldi-TOF-MS: Calcd. [M+Na+]=1256.93 Da; Obs. [M+Na+]=1256.86 Da. The following components with a mass below 580 Da were determined by LC-MS and quantified:

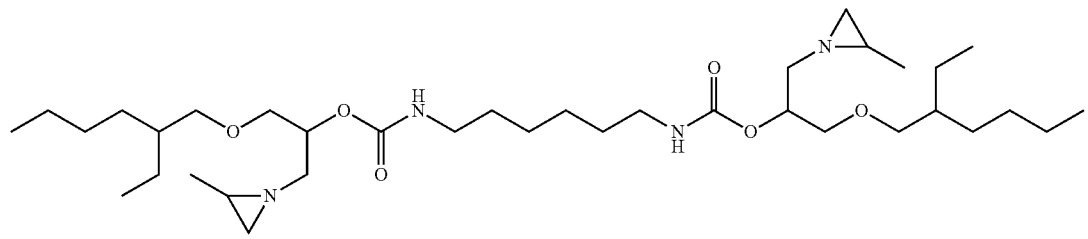 [SMILES: CCCCC(CC)COCC(CN1CC1C)OC(=O)NCCCCCCNC(=O)OC(COCC(CC)CCCC)CN1CC1C]

was present in the composition at 0.84 wt. % and

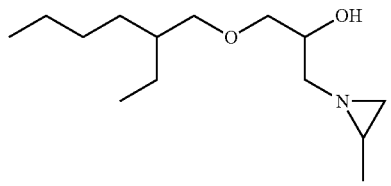 [SMILES: CCCCC(CC)COCC(O)CN1CC1C]

was present at 0.16 wt. %.

Genotoxicity Test

|  | Without S9 rat liver extract | | | | | | With S9 rat liver extract | | | | | |
| --- | --- | --- | --- | --- | --- | --- | --- | --- | --- | --- | --- | --- |
| | Bscl 2 | | | Rtkn | | | Bscl 2 | | | Rtkn | | |
| | \multicolumn{6}{c}{concentration} | | | | | | | | |
| | 10 | 25 | 50 | 10 | 25 | 50 | 10 | 25 | 50 | 10 | 25 | 50 |
| Composition 23 | 1.0 | 1.0 | 0.7 | 1.1 | 1.3 | 1.2 | 0.9 | 0.8 | 0.7 | 1.0 | 1.1 | 1.1 |

The genotoxicity test results show that the crosslinker composition of Example 23 is non-genotoxic.

Subsequently, 15 grams of the viscous liquid obtained in the previous step was mixed with 7.5 grams of acetone and incubated at 50° C. until a homogeneous solution was obtained. To this solution was added 0.03 grams of triethylamine (TEA) and then 1.5 grams of molten Maxemul™ 7101 dispersant. The resulting mixture was stirred for 5 minutes at room temperature using an IKA T25 Digital Ultra-Turrax® mixer with S 25 N-18G head at 2,000 rpm. Then, stirring was increased to 10,000 rpm and 15 grams of demineralized water, brought to pH 11 using triethylamine, was added gradually to the mixture over 15 minutes. During this addition process, the mixer was moved around the reaction vessel continuously. After completion of the addition, the resulting dispersion was stirred at 5,000 rpm for 10 more minutes, and the pH of the dispersion was set to 11 with TEA.

Functional performance and stability of the crosslinker dispersion were assessed using spot tests on coating surfaces, based on procedures from the DIN 68861-1 standard, and viscosity measurements as well as particle size measurements. For these tests, the crosslinker dispersion was stored in an oven at 50° C. for 4 weeks. Every week, the viscosity and the particle size of the crosslinker dispersion were determined. Additionally, every week, 2.3 grams of the aged crosslinker dispersion was mixed with 21 grams of Polymer P1 under continuous stirring, and the resulting mixture was further stirred for 30 minutes. This coating composition was filtered and applied to Leneta test cards using 100 μm wire rod applicators (Test 23). For reference, films were also cast from the same composition lacking the crosslinker dispersion (Test Blank). The films were dried for 1 hour at 25° C., then annealed at 50° C. for 16 hours. Subsequently, a piece of cotton wool was soaked in 1:1 EtOH:demineralized water and placed on the film for 1 hour. After removal of the EtOH and 60 minutes recovery, the following results were obtained (a score of 1 indicates complete degradation of the film, 5 indicates no damage visible):

Performance and Stability Test

| Sample | Week 0 | Week 1 | Week 2 | Week 3 | Week 4 |
|---|---|---|---|---|---|
| Particle size 23 (nm) | 195 | 195 | 203 | 199 | 202 |
| Viscosity 23 (mPa · s) | 60 | 65 | 64 | 68 | 71 |
| Test 23 | 5 | 4 | 5 | 5 | 5 |
| Test Blank | 1 | 1 | 1 | 1 | 1 |

EXAMPLE 24

A 1 L round bottom flask equipped with a condenser was placed under a $N_2$ atmosphere and charged with propylene imine (69.0 gram), Cardura E10P (201.0 gram) and $K_2CO_3$ (7.30 gram) and heated to 80° C., after which the mixture was stirred for 24 h at T=80° C. After filtration the excess of PI was removed in vacuo, resulting in a colorless low viscous liquid.

34.7 grams of the resulting material (2-hydroxy-3-(2-methylaziridin-1-yl)propyl neodecanoate) was charged to a reaction flask equipped with a thermometer, together with 0.05 grams of bismuth neodecanoate and 400 grams of dimethylformamide. The mixture was stirred with a mechanical upper stirrer under a nitrogen atmosphere and heated to 50° C. A solution of 30 grams of Desmodur N 3600 in 288 grams of dimethylformamide was then added dropwise in 45 minutes to the reaction flask. After maintaining temperature for 15 minutes, 16.2 grams of a poly(ethylene glycol) monomethyl ether with an average Mn of 500 Da was added to the reactor, flushed with 10 mL of dimethylformamide, whereafter the mixture was heated further to 70° C. Samples were taken at regular intervals and the reaction progress was monitored using a Bruker Alpha FT-IR spectrometer until no NCO-stretch at 2200-2300 $cm^{-1}$ was observed. The solvent was removed in vacuo to obtain a clear highly viscous liquid. The calculated molecular weight of the theoretical main components were 1359.96 Da (three aziridines) and 1591.04 Da (two aziridines, 11 EG repeating units), chemical structures are shown below.

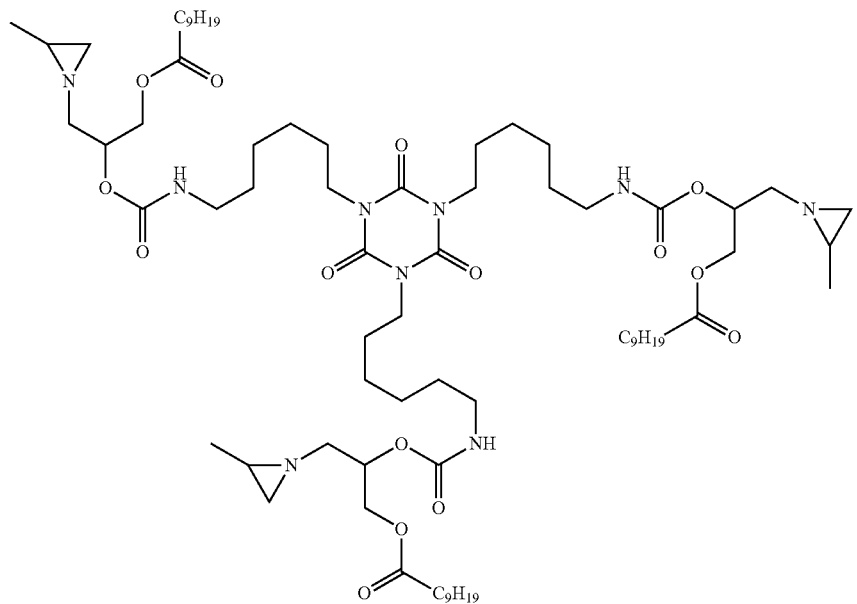

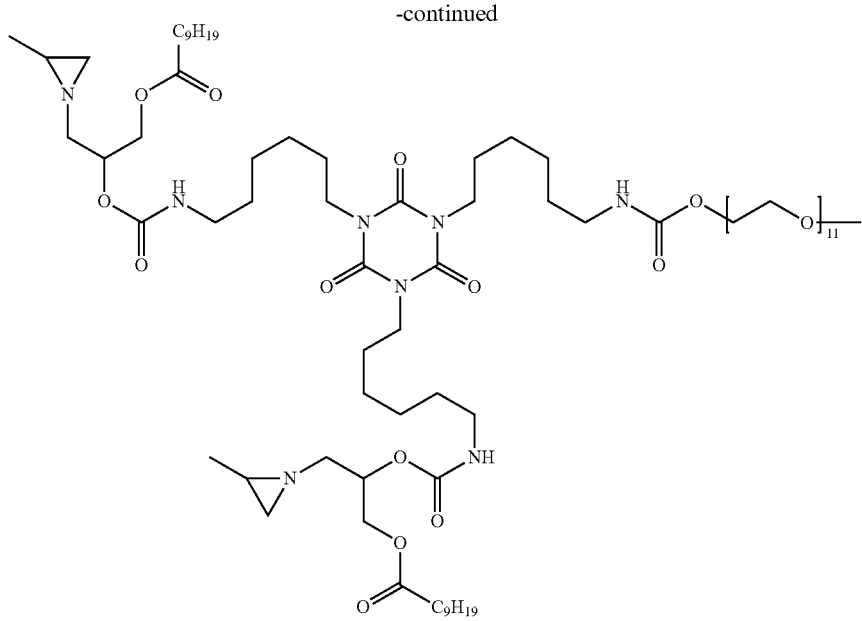

Subsequently, 30 grams of the viscous liquid obtained in the previous step was mixed with 15 grams of acetone and incubated at 50° C. until a homogeneous solution was obtained. To this solution was added 0.03 grams of triethylamine (TEA) and then 3.0 grams of molten Maxemul™ 7101 dispersant. The resulting mixture was stirred for 5 minutes at room temperature using an IKA T25 Digital Ultra-Turrax® mixer with S 25 N-18G head at 2,000 rpm. Then, stirring was increased to 10,000 rpm and 30 grams of demineralized water, brought to pH 11 using triethylamine, was added gradually to the mixture over 15 minutes. During this addition process, the mixer was moved around the reaction vessel continuously. After completion of the addition, the resulting dispersion was stirred at 5,000 rpm for 10 more minutes, and the pH of the dispersion was set to 11 with TEA.

Functional performance and stability of the crosslinker dispersion were assessed using spot tests on coating surfaces, based on procedures from the DIN 68861-1 standard, and viscosity measurements as well as particle size measurements. For these tests, the crosslinker dispersion was stored in an oven at 50° C. for 4 weeks. Every week, the viscosity and the particle size of the crosslinker dispersion were determined. Additionally, every week, 3.4 grams of the aged crosslinker dispersion was mixed with 21 grams of Polymer P1 under continuous stirring, and the resulting mixture was further stirred for 30 minutes. This coating composition was filtered and applied to Leneta test cards using 100 μm wire rod applicators (Test 24). For reference, films were also cast from the same composition lacking the crosslinker dispersion (Test Blank). The films were dried for 1 hour at 25° C., then annealed at 50° C. for 16 hours. Subsequently, a piece of cotton wool was soaked in 1:1 EtOH:demineralized water and placed on the film for 1 hour. After removal of the EtOH and 60 minutes recovery, the following results were obtained (a score of 1 indicates complete degradation of the film, 5 indicates no damage visible):

Performance and Stability Test

| Sample | Week 0 | Week 1 | Week 2 | Week 3 | Week 4 |
| --- | --- | --- | --- | --- | --- |
| Particle size 24 (nm) | 30 | 31 | 33 | 30 | 38 |
| Viscosity 24 (mPa · s) | 2792 | 4100 | 4650 | 5400 | 5400 |
| Test 24 | 4 | 4 | 4 | 4 | 3 |
| Test Blank | 1 | 1 | 1 | 1 | 1 |

EXAMPLE 25

A first crosslinker was synthesized by charging 15.0 grams of Desmodur N 3600, 7.09 grams of 1-(2-methylaziridin-1-yl)propan-2-ol, 8.21 grams of a poly(ethylene glycol) monomethyl ether with an average Mn of 500 Da and 110 grams of 2-methyltetrahydrofuran to a reaction flask equipped with a thermometer. The mixture was stirred with a mechanical upper stirrer under a nitrogen atmosphere. The mixture was then heated to 50° C., kept at that temperature for 15 minutes and then heated further to 60° C. Samples were taken at regular intervals and the reaction progress was monitored using a Bruker Alpha FT-IR spectrometer until no NCO-stretch at 2200-2300 $cm^{-1}$ was observed. The solvent was removed in vacuo to obtain a clear highly viscous liquid. The calculated molecular weights of the theoretical main components were 849.57 Da (three aziridines), 1250.78 Da (two aziridines, 11 EG repeating units), 1294.81 Da (two aziridines, 12 EG repeating units) and 1338.84 Da (two aziridines, 13 EG repeating units), chemical structures are shown below.

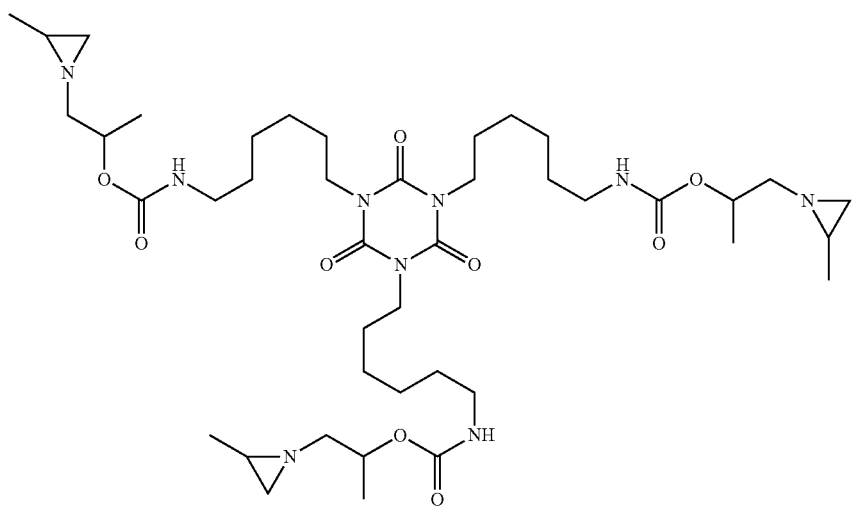
Molecular weight was confirmed by Maldi-TOF-MS: Calcd. [M+Na+]=872.57 Da; Obs. [M+Na+]=872.54 Da.
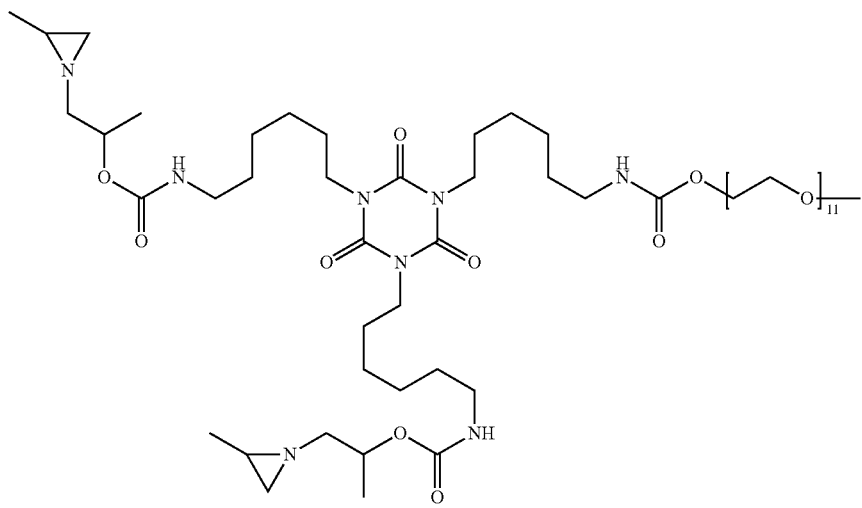
Molecular weight was confirmed by Maldi-TOF-MS: Calcd. [M+Na+]=1273.78 Da; Obs. [M+Na+]=1273.76 Da.
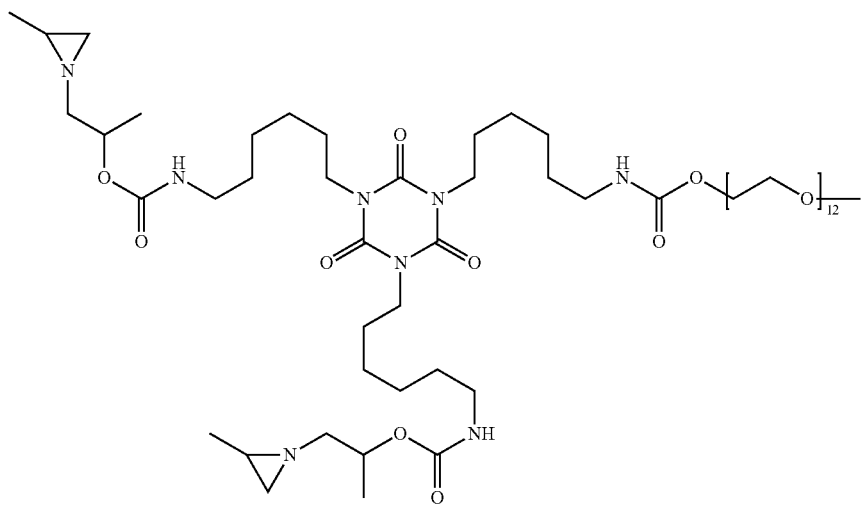

Molecular weight was confirmed by Maldi-TOF-MS: Calcd. [M+Na+]=1317.81 Da; Obs. [M+Na+]=1317.78 Da.

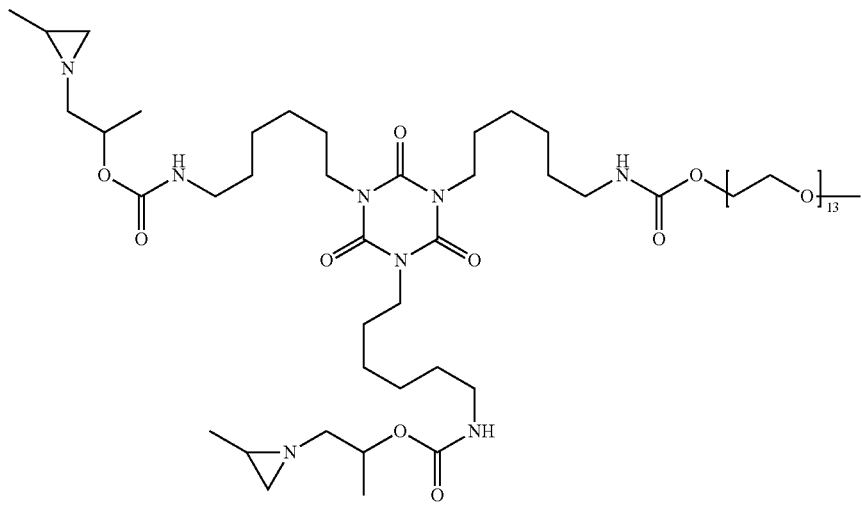

Molecular weight was confirmed by Maldi-TOF-MS: Calcd. [M+Na+]=1361.84 Da; Obs. [M+Na+]=1361.81 Da. The following components with a mass below 580 Da were determined by LC-MS and quantified:

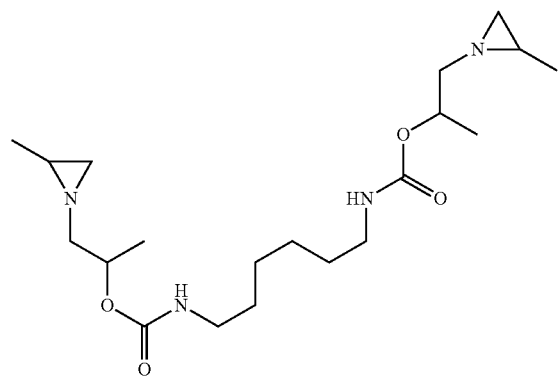

was present in the composition at 0.26 wt. %.

Genotoxicity Test

|  | Without S9 rat liver extract | | | | | | With S9 rat liver extract | | | | | |
| --- | --- | --- | --- | --- | --- | --- | --- | --- | --- | --- | --- | --- |
|  | Bscl 2 | | | Rtkn | | | Bscl 2 | | | Rtkn | | |
|  | \multicolumn{6}{c}{concentration} | | | | | | | | |
|  | 10 | 25 | 50 | 10 | 25 | 50 | 10 | 25 | 50 | 10 | 25 | 50 |
| Composition 25-1 | 1.1 | 1.3 | 1.5 | 1.1 | 1.2 | 1.3 | 1.3 | 1.3 | 1.4 | 1.0 | 1.1 | 1.1 |

The genotoxicity test results show that the crosslinker composition 25-1 is non-genotoxic.

A second crosslinker was synthesized by placing a 1 L round bottom flask equipped with a condensor under a $N_2$ atmosphere and charging it with propylene imine (69.0 gram), Cardura E10P (201.0 gram) and $K_2CO_3$ (7.30 gram) and subsequently heating to 80° C., after which the mixture was stirred for 24 h at T=80° C. After filtration the excess of PI was removed in vacuo, resulting in a colorless low viscous liquid.

32.3 grams of the resulting material (2-hydroxy-3-(2-methylaziridin-1-yl)propyl neodecanoate) was charged to a reaction flask equipped with a thermometer, together with 0.02 grams of bismuth neodecanoate and 6.79 grams of 2-methyltetrahydrofuran. The mixture was stirred with a mechanical upper stirrer under a nitrogen atmosphere and heated to 50° C. A solution of 22.7 grams of Desmodur N 3600 in 6.79 grams of 2-methyltetrahydrofuran was then added dropwise in 45 minutes to the reaction flask, a further 10 grams of 2-methyltetrahydrofuran was flushed through the feeding funnel into the reaction mixture, whereafter the mixture was heated further to 70° C. Samples were taken at regular intervals and the reaction progress was monitored using a Bruker Alpha FT-IR spectrometer until no NCO-stretch at 2200-2300 $cm^{-1}$ was observed. The solvent was removed in vacuo to obtain an opaque highly viscous liquid. The calculated molecular weight of the theoretical main component was 1359.96 Da, chemical structure is shown below.

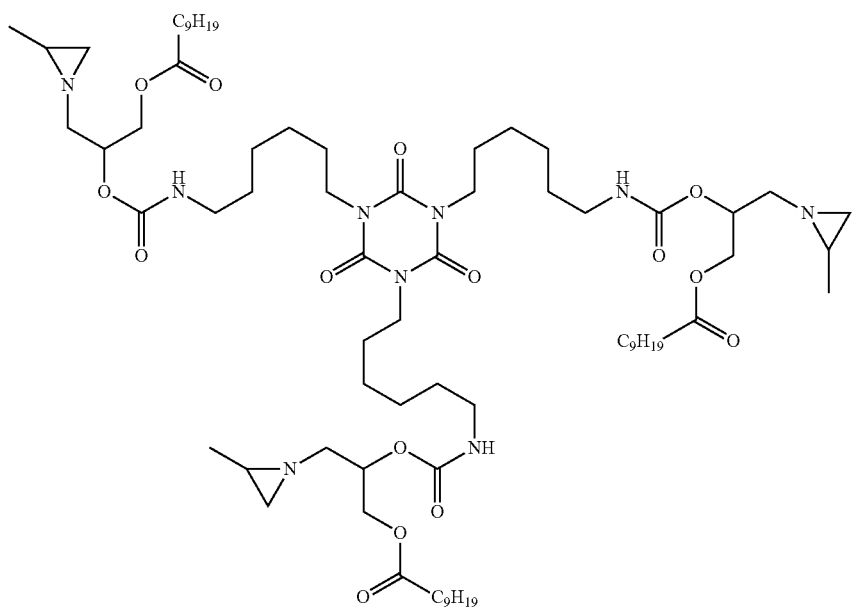

Molecular weight was confirmed by Maldi-TOF-MS: Calcd. [M+Na+]=1382.95 Da; Obs. [M+Na+]=1382.94 Da.

Genotoxicity Test

|  | Without S9 rat liver extract | | | With S9 rat liver extract | | |
|---|---|---|---|---|---|---|
|  | Bscl 2 | | | Rtkn | Bscl 2 | Rtkn |
|  | concentration | | | | | |
|  | 10 25 50 | 10 25 50 | 10 25 50 | 10 25 50 |
| Composition 25-2 | 1.1 1.2 1.0 | 1.1 1.2 1.0 | 1.0 1.1 1.1 | 1.1 1.1 1.2 |

The genotoxicity test results show that the crosslinker composition 25-2 is non-genotoxic.

Subsequently, 1.5 grams of the viscous liquid obtained in the first crosslinker synthesis was mixed with 13.5 grams of the viscous liquid obtained in the second crosslinker synthesis, 7.5 grams of acetone and incubated at 50° C. until a homogeneous solution was obtained. To this solution was added 0.03 grams of triethylamine (TEA) and then 1.5 grams of molten Maxemul™ 7101 dispersant. The resulting mixture was stirred for 5 minutes at room temperature using an IKA T25 Digital Ultra-Turrax® mixer with S 25 N-18G head at 2,000 rpm. Then, stirring was increased to 10,000 rpm and 15 grams of demineralized water, brought to pH 11 using triethylamine, was added gradually to the mixture over 15 minutes. During this addition process, the mixer was moved around the reaction vessel continuously. After completion of the addition, the resulting dispersion was stirred at 5,000 rpm for 10 more minutes, and the pH of the dispersion was set to 11 with TEA.

Functional performance and stability of the crosslinker dispersion were assessed using spot tests on coating surfaces, based on procedures from the DIN 68861-1 standard, and viscosity measurements as well as particle size measurements. For these tests, the crosslinker dispersion was stored in an oven at 50° C. for 4 weeks. Every week, the viscosity and the particle size of the crosslinker dispersion were determined. Additionally, every week, 2.8 grams of the aged crosslinker dispersion was mixed with 21 grams of Polymer P1 under continuous stirring, and the resulting mixture was further stirred for 30 minutes. This coating composition was filtered and applied to Leneta test cards using 100 μm wire rod applicators (Test 25). For reference, films were also cast from the same composition lacking the crosslinker dispersion (Test Blank). The films were dried for 1 hour at 25° C., then annealed at 50° C. for 16 hours. Subsequently, a piece of cotton wool was soaked in 1:1 EtOH:demineralized water and placed on the film for 1 hour. After removal of the EtOH and 60 minutes recovery, the following results were obtained (a score of 1 indicates complete degradation of the film, 5 indicates no damage visible):

Performance and Stability Test

| Sample | Week 0 | Week 1 | Week 2 | Week 3 | Week 4 |
|---|---|---|---|---|---|
| Particle size 25 (nm) | 1061 | 1011 | 1165 | 1088 | 992 |
| Viscosity 25 (mPa · s) | 604 | 460 | 590 | 616 | 699 |
| Test 25 | 4 | 4 | 4 | 4 | 4 |
| Test Blank | 1 | 1 | 1 | 1 | 1 |

EXAMPLE 26

A 1 L round bottom flask equipped with a condensor was placed under a $N_2$ atmosphere and charged with propylene imine (80.0 gram), n-butyl glycidyl ether (126.0 gram) and $K_2CO_3$ (10.00 gram) and heated to 80° C. in 30 min, after which the mixture was stirred for 21 h at T=80° C. After filtration the excess of PI was removed in vacuo, followed by further purification via vacuum distillation, resulting in a colorless low viscous liquid.

20 grams of Desmodur N 3400 and 0.02 grams of bismuth neodecanoate were charged to a reaction flask equipped with a thermometer. The mixture was stirred with a mechanical upper stirrer under a nitrogen atmosphere and heated to 50° C. 17.88 grams of the product from the first step was then added dropwise in 10 minutes to the reaction flask, whereafter the mixture was heated further to 70° C. Samples were taken at regular intervals and the reaction progress was monitored using a Bruker Alpha FT-IR spectrometer until no change in NCO-stretch at 2200-2300 cm$^{-1}$ was observed. Subsequently, 0.16 grams of 1-butanol were added to the mixture, followed by further reaction to complete disappearance of aforementioned NCO-stretch peak. The product was a yellowish highly viscous liquid. The calculated molecular weight of the theoretical main component was 710.49 Da, chemical structure is shown below.

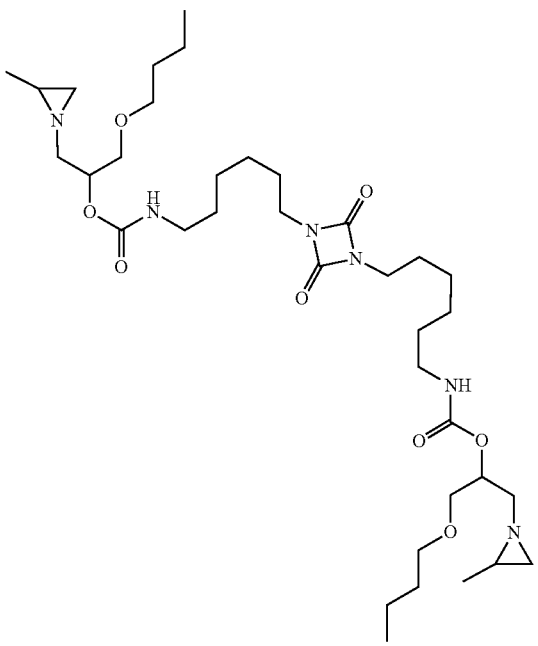 [SMILES: CCCCOCC(CN1CC1C)OC(=O)NCCCCCCN1C(=O)N(CCCCCCNC(=O)OC(COCCCC)CN2CC2C)C1=O]

Molecular weight was confirmed by Maldi-TOF-MS: Calcd. [M+Na+]=733.49 Da; Obs. [M+Na+]=733.57 Da. The following components with a mass below 580 Da were determined by LC-MS and quantified:

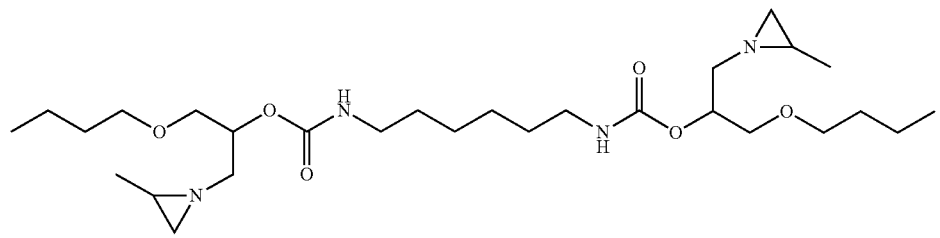 [SMILES: CCCCOCC(CN1CC1C)OC(=O)NCCCCCCNC(=O)OC(COCCCC)CN1CC1C]

was present in the composition at 0.2 wt. % and

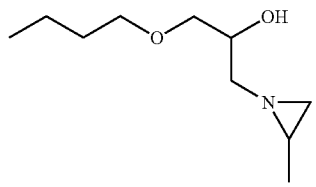

was present at less than 0.01 wt. %.

Genotoxicity Test

| | Without S9 rat liver extract | | | | | | With S9 rat liver extract | | | | | |
| --- | --- | --- | --- | --- | --- | --- | --- | --- | --- | --- | --- | --- |
| | Bscl 2 | | | Rtkn | | | Bscl 2 | | | Rtkn | | |
| | \multicolumn{6}{c}{concentration} | | | | | | | | |
| | 10 | 25 | 50 | 10 | 25 | 50 | 10 | 25 | 50 | 10 | 25 | 50 |
| Composition 26 | 1.1 | 1.3 | 1.2 | 1.1 | 1.2 | 1.2 | 1.2 | 1.2 | 1.2 | 1.4 | 1.6 | 1.4 |

The genotoxicity test results show that the crosslinker composition of Example 26 only has weakly positive induced genotoxicity.

Subsequently, 15 grams of the viscous liquid obtained in the previous step was mixed with 7.5 grams of acetone and incubated at 50° C. until a homogeneous solution was obtained. To this solution was added 0.03 grams of triethylamine (TEA) and then 1.5 grams of Atlas™ G-5002L-LQ dispersant. The resulting mixture was stirred for 5 minutes at room temperature using an IKA T25 Digital Ultra-Turrax® mixer with S 25 N-18G head at 2,000 rpm. Then, stirring was increased to 10,000 rpm and 15 grams of demineralized water, brought to pH 11 using triethylamine, was added gradually to the mixture over 15 minutes. During this addition process, the mixer was moved around the reaction vessel continuously. After completion of the addition, the resulting dispersion was stirred at 5,000 rpm for 10 more minutes, and the pH of the dispersion was set to 11 with TEA.

Functional performance and stability of the crosslinker dispersion were assessed using spot tests on coating surfaces, based on procedures from the DIN 68861-1 standard, and viscosity measurements as well as particle size measurements. For these tests, the crosslinker dispersion was stored in an oven at 50° C. for 4 weeks. Every week, the viscosity and the particle size of the crosslinker dispersion were determined. Additionally, every week, 2.1 grams of the aged crosslinker dispersion was mixed with 21 grams of Polymer P1 under continuous stirring, and the resulting mixture was further stirred for 30 minutes. This coating composition was filtered and applied to Leneta test cards using 100 μm wire rod applicators (Test 26). For reference, films were also cast from the same composition lacking the crosslinker dispersion (Test Blank). The films were dried for 1 hour at 25° C., then annealed at 50° C. for 16 hours. Subsequently, a piece of cotton wool was soaked in 1:1 EtOH:demineralized water and placed on the film for 1 hour. After removal of the EtOH and 60 minutes recovery, the following results were obtained (a score of 1 indicates complete degradation of the film, 5 indicates no damage visible):

Performance and Stability Test

| Sample | Week 0 | Week 1 | Week 2 | Week 3 | Week 4 |
| --- | --- | --- | --- | --- | --- |
| Particle size 26 (nm) | 198 | 186 | 182 | 180 | 185 |
| Viscosity 26 (mPa · s) | 235 | 159 | 115 | 168 | 128 |
| Test 26 | 4 | 4 | 3 | 3 | 2 |
| Test Blank | 1 | 1 | 1 | 1 | 1 |

EXAMPLE 27

The (1-butoxy-3-(2-methylaziridin-1-yl)propan-2-ol) intermediate was prepared as described in Example 1, and 9.6 grams were charged to a reaction flask equipped with a thermometer, together with 0.02 grams of bismuth neodecanoate and 30 grams of 2-methyltetrahydrofuran. The mixture was stirred with a mechanical upper stirrer under a nitrogen atmosphere and heated to 50° C. A solution of 10 grams of Desmodur N 3900 in 30 grams of 2-methyltetrahydrofuran was then added dropwise in 45 minutes to the reaction flask, whereafter the mixture was heated further to 70° C. Samples were taken at regular intervals and the reaction progress was monitored using a Bruker Alpha FT-IR spectrometer until no change in NCO-stretch at 2200-2300 cm$^{-1}$ was observed. Subsequently, 0.33 grams of 1-butanol were added to the mixture, followed by further reaction to complete disappearance of aforementioned NCO-stretch peak. The solvent was removed in vacuo to obtain a clear, yellowish highly viscous liquid. The calculated molecular weight of the theoretical main component was 1065.74 Da, chemical structure is shown below.

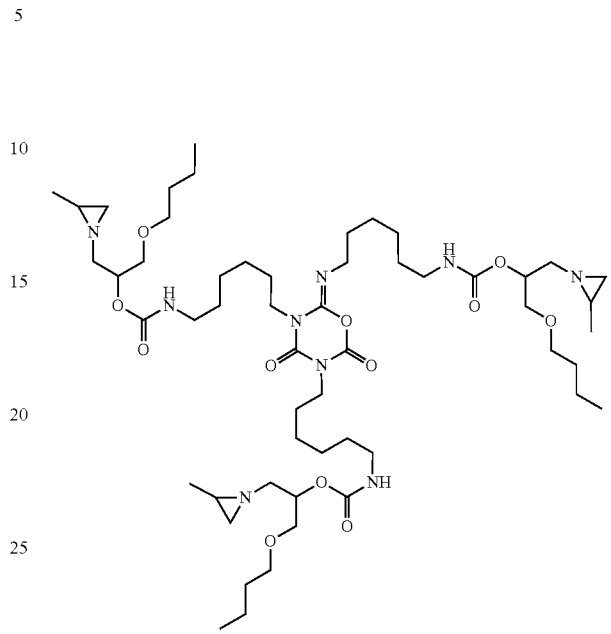

Molecular weight was confirmed by Maldi-TOF-MS: Calcd. [M+Na+]=1088.74 Da; Obs. [M+Na+]=1088.81 Da. The following components with a mass below 580 Da were determined by LC-MS and quantified:

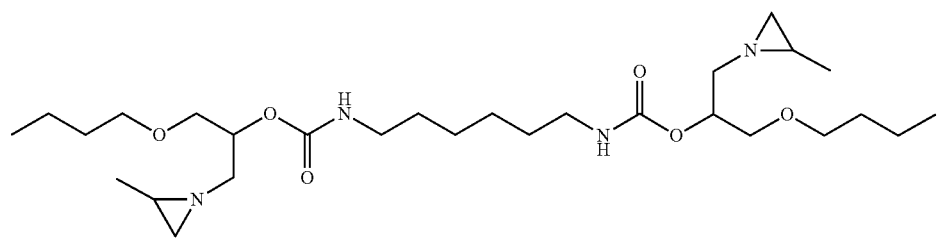 [SMILES: CCCCOCC(CN1CC1C)OC(=O)NCCCCCCNC(=O)OC(COCCCC)CN1CC1C]

was present in the composition at 0.30 wt. % and

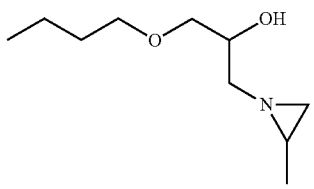

was present at 0.02 wt. %.
Genotoxicity Test

|  | Without S9 rat liver extract | | | | | | With S9 rat liver extract | | | | | |
|---|---|---|---|---|---|---|---|---|---|---|---|---|
|  | Bscl 2 | | | Rtkn | | | Bscl 2 | | | Rtkn | | |
|  | concentration | | | | | | | | | | | |
|  | 10 | 25 | 50 | 10 | 25 | 50 | 10 | 25 | 50 | 10 | 25 | 50 |
| Composition 27 | 1.1 | 1.1 | 0.9 | 1.1 | 1.0 | 0.9 | 1.0 | 0.9 | 0.7 | 1.1 | 1.0 | 0.9 |

The genotoxicity test results show that the crosslinker composition of Example 27 is non-genotoxic.

Subsequently, 15 grams of the viscous liquid obtained in the previous step was mixed with 7.5 grams of acetone and incubated at 50° C. until a homogeneous solution was obtained. To this solution was added 0.03 grams of triethylamine (TEA) and then 1.5 grams of molten Maxemul™ 7101 dispersant. The resulting mixture was stirred for 5 minutes at room temperature using an IKA T25 Digital Ultra-Turrax® mixer with S 25 N-18G head at 2,000 rpm. Then, stirring was increased to 10,000 rpm and 15 grams of demineralized water, brought to pH 11 using triethylamine, was added gradually to the mixture over 15 minutes. During this addition process, the mixer was moved around the reaction vessel continuously. After completion of the addition, the resulting dispersion was stirred at 5,000 rpm for 10 more minutes, and the pH of the dispersion was set to 11 with TEA.

Functional performance and stability of the crosslinker dispersion were assessed using spot tests on coating surfaces, based on procedures from the DIN 68861-1 standard, and viscosity measurements as well as particle size measurements. For these tests, the crosslinker dispersion was stored in an oven at 50° C. for 4 weeks. Every week, the viscosity and the particle size of the crosslinker dispersion were determined.

Additionally, every week, 2.0 grams of the aged crosslinker dispersion was mixed with 21 grams of Polymer P1 under continuous stirring, and the resulting mixture was further stirred for 30 minutes. This coating composition was filtered and applied to Leneta test cards using 100 μm wire rod applicators (Test 27). For reference, films were also cast from the same composition lacking the crosslinker dispersion (Test Blank). The films were dried for 1 hour at 25° C., then annealed at 50° C. for 16 hours. Subsequently, a piece of cotton wool was soaked in 1:1 EtOH:demineralized water and placed on the film for 1 hour. After removal of the EtOH and 60 minutes recovery, the following results were obtained (a score of 1 indicates complete degradation of the film, 5 indicates no damage visible):

Performance and Stability Test

| Sample | Week 0 | Week 1 | Week 2 | Week 3 | Week 4 |
|---|---|---|---|---|---|
| Particle size 27 (nm) | 169 | 174 | 171 | 169 | 185 |
| Viscosity 27 (mPa · s) | 288 | 300 | 222 | 214 | 174 |
| Test 27 | 5 | 4 | 4 | 4 | 4 |
| Test Blank | 1 | 1 | 1 | 1 | 1 |

EXAMPLE 28

A 1 L round bottom flask equipped with a condensor was placed under a $N_2$ atmosphere and charged with propylene imine (80 gram), n-butyl glycidyl ether (126.0 gram) and $K_2CO_3$ (10.00 gram) and heated to 80° C. in 30 min, after which the mixture was stirred for 21 h at T=80° C. After filtration the excess of PI was removed in vacuo, followed by further purification via vacuum distillation, resulting in a colorless low viscous liquid.

73.3 grams of the resulting material (1-butoxy-3-(2-methylaziridin-1-yl)propan-2-ol) was charged to a reaction flask equipped with a thermometer, together with 0.02 grams of bismuth neodecanoate and 460 grams of dimethylformamide. The mixture was stirred with a mechanical upper stirrer under a nitrogen atmosphere and heated to 50° C. A solution of 162.6 grams of Desmodur N 3800 in 460 grams of dimethylformamide was then added dropwise in 45 minutes to the reaction flask, whereafter the mixture was heated further to 70° C. Samples were taken at regular intervals and the reaction progress was monitored using a Bruker Alpha FT-IR spectrometer until no NCO-stretch at 2200-2300 $cm^{-1}$ was observed. The solvent was removed in vacuo to obtain a clear, yellowish highly viscous liquid.

The calculated molecular weight of the theoretical main components were 1065.74 Da (three aziridine groups) and 1589.08 (four aziridine groups), chemical structures are shown below.

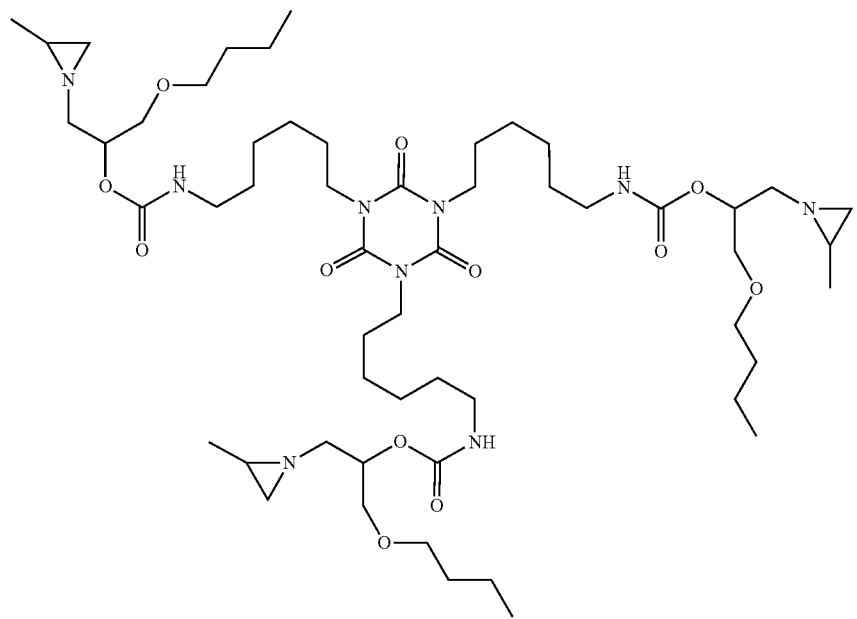
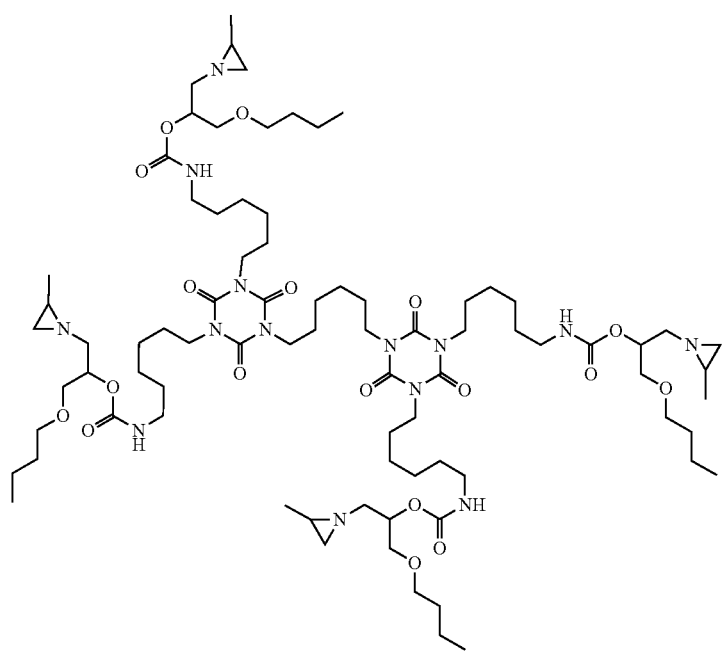
Molecular weight were confirmed by Maldi-TOF-MS: Calcd. [M+Na+]=1088.74 Da; Obs. [M+Na+]=1088.79 Da (three aziridine groups). Calcd. Calcd. [M+Na+]=1612.07 Da; Obs. [M+Na+]=1612.19 Da (four aziridine groups).

The following components with a mass below 580 Da were determined by LC-MS and quantified:

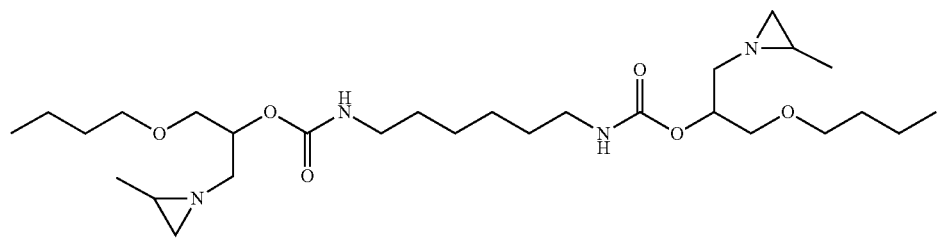 [SMILES: CCCCOCC(CN1CC1C)OC(=O)NCCCCCCNC(=O)OC(COCCCC)CN1CC1C]

was present in the composition at 0.31 wt. % and

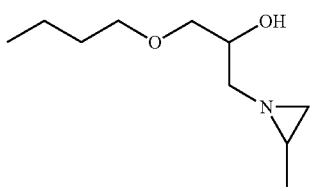

was present at less than 0.01 wt. %.

Subsequently, 20 grams of the viscous liquid obtained in the previous step was mixed with 10 grams of Proglyde™ DMM and incubated at 50° C. until a homogeneous solution was obtained. To this solution was added 0.03 grams of triethylamine (TEA) and then 2.7 grams of Pluronic® P84 dispersant. The resulting mixture was stirred for 5 minutes at room temperature using an IKA T25 Digital Ultra-Turrax® mixer with S 25 N-18G head at 2,000 rpm. Then, stirring was increased to 10,000 rpm and 20 grams of demineralized water, brought to pH 11 using triethylamine, was added gradually to the mixture over 15 minutes. During this addition process, the mixer was moved around the reaction vessel continuously. After completion of the addition, the resulting dispersion was stirred at 5,000 rpm for 10 more minutes, and the pH of the dispersion was set to 11 with TEA.

Functional performance and stability of the crosslinker dispersion were assessed using spot tests on coating surfaces, based on procedures from the DIN 68861-1 standard, and viscosity measurements as well as particle size measurements. For these tests, the crosslinker dispersion was stored in an oven at 50° C. for 4 weeks. Every week, the viscosity and the particle size of the crosslinker dispersion were determined. Additionally, every week, 3.0 grams of the aged crosslinker dispersion was mixed with 21 grams of Polymer P1 under continuous stirring, and the resulting mixture was further stirred for 30 minutes. This coating composition was filtered and applied to Leneta test cards using 100 μm wire rod applicators (Test 28). For reference, films were also cast from the same composition lacking the crosslinker dispersion (Test Blank). The films were dried for 1 hour at 25° C., then annealed at 50° C. for 16 hours. Subsequently, a piece of cotton wool was soaked in 1:1 EtOH:demineralized water and placed on the film for 1 hour. After removal of the EtOH and 60 minutes recovery, the following results were obtained (a score of 1 indicates complete degradation of the film, 5 indicates no damage visible):

Performance and Stability Test

| Sample | Week 0 | Week 1 | Week 2 | Week 3 | Week 4 |
|---|---|---|---|---|---|
| Particle size 28 (nm) | 1223 | 1086 | 1014 | 1073 | 1001 |
| Viscosity 28 (mPa · s) | 254 | 180 | 240 | 200 | 170 |
| Test 28 | 4 | 4 | 4 | 4 | 4 |
| Test Blank | 1 | 1 | 1 | 1 | 1 |

EXAMPLE 29

A 1 L round bottom flask equipped with a condensor was placed under a $N_2$ atmosphere and charged with propylene imine (69.0 gram), Cardura E10P (201.0 gram) and $K_2CO_3$ (7.30 gram) and heated to 80° C., after which the mixture was stirred for 24 h at T=80° C. After filtration the excess of PI was removed in vacuo, resulting in a colorless low viscous liquid.

A 500 mL round bottom flask equipped with a thermometer and overhead stirrer was placed under a $N_2$ atmosphere and charged with Desmodur W (60.08 gram) and 65.35 gram of the product of the previous step. The resulting mixture was heated to 50° C., after which bismuth neodecanoate (0.05 gram) was added. The mixture was allowed to exotherm followed by further heating to 80° C. and stirring for 2.5 hours at 80° C. To the mixture was then added pTHF650 (74.52 gram) and the mixture was stirred for another 1 hour at 80° C. The solvent was removed in vacuo to obtain a colorless solid.

The calculated molecular weights of the theoretical main components were 832.63 Da (no pTHF650 repeat unit), 1473.10 (one pTHF segment with 5 tetramethylene ether glycol repeat units), 1545.15 Da (one pTHF segment with 6 tetramethylene ether glycol repeat units) and 2257.68 Da (two pTHF segments with 6 tetramethylene ether glycol repeat units each), chemical structures are shown below.

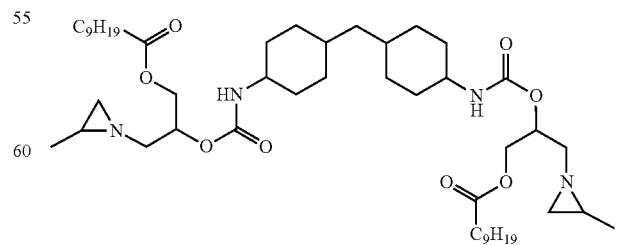

Molecular weight was confirmed by Maldi-TOF-MS: Calcd. [M+Na+]=855.63 Da; Obs. [M+Na+]=855.66 Da.

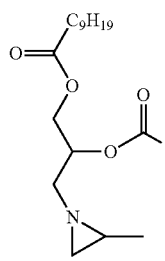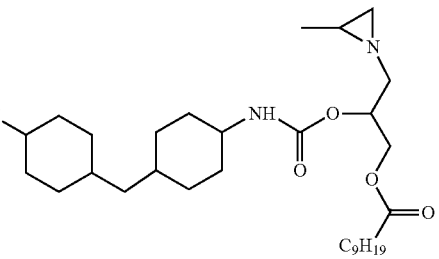

Molecular weight was confirmed by Maldi-TOF-MS: Calcd. [M+Na+]=1496.10 Da; Obs. [M+Na+]=1496.16 Da.

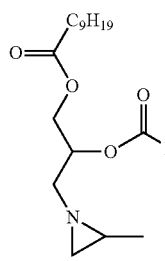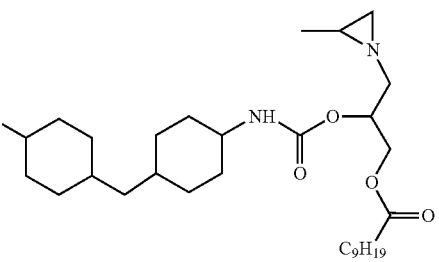

Molecular weight was confirmed by Maldi-TOF-MS: Calcd. [M+Na+]=1568.15 Da; Obs. [M+Na+]=1568.21 Da.

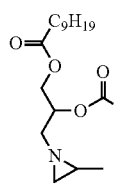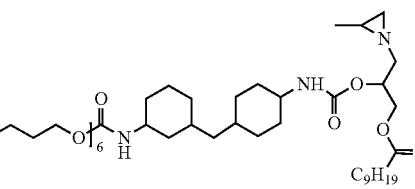

Molecular weight was confirmed by Maldi-TOF-MS: Calcd. [M+Na+]=2280.68 Da; Obs. [M+Na+]=2280.78 Da.

Subsequently, 15 grams of the colorless solid obtained in the previous step was mixed with 7.5 grams of acetone and incubated at 50° C. until a homogeneous solution was obtained. To this solution was added 0.03 grams of triethylamine (TEA) and then 1.5 grams of molten Maxemul™ 7101 dispersant. The resulting mixture was stirred for 5 minutes at room temperature using an IKA T25 Digital Ultra-Turrax® mixer with S 25 N-18G head at 2,000 rpm. Then, stirring was increased to 10,000 rpm and 15 grams of demineralized water, brought to pH 11 using triethylamine, was added gradually to the mixture over 15 minutes. During this addition process, the mixer was moved around the reaction vessel continuously. After completion of the addition, the resulting dispersion was stirred at 5,000 rpm for 10 more minutes, and the pH of the dispersion was set to 11 with TEA.

Functional performance and stability of the crosslinker dispersion were assessed using spot tests on coating surfaces, based on procedures from the DIN 68861-1 standard, and viscosity measurements as well as particle size measurements. For these tests, the crosslinker dispersion was stored in an oven at 50° C. for 4 weeks. Every week, the viscosity and the particle size of the crosslinker dispersion were determined. Additionally, every week, 4.8 grams of the aged crosslinker dispersion was mixed with 21 grams of Polymer P1 under continuous stirring, and the resulting mixture was further stirred for 30 minutes. This coating composition was filtered and applied to Leneta test cards using 100 μm wire rod applicators (Test 29). For reference, films were also cast from the same composition lacking the crosslinker dispersion (Test Blank). The films were dried for 1 hour at 25° C., then annealed at 50° C. for 16 hours. Subsequently, a piece of cotton wool was soaked in 1:1 EtOH:demineralized water and placed on the film for 1 hour. After removal of the EtOH and 60 minutes recovery, the following results were obtained (a score of 1 indicates complete degradation of the film, 5 indicates no damage visible):

Performance and Stability Test

| Sample | Week 0 | Week 1 | Week 2 | Week 3 | Week 4 |
|---|---|---|---|---|---|
| Particle size 29 (nm) | 210 | n.d. | 242 | n.d. | 229 |
| Viscosity 29 (mPa · s) | 56 | n.d. | 38 | n.d. | 40 |

-continued

| Sample | Week 0 | Week 1 | Week 2 | Week 3 | Week 4 |
|---|---|---|---|---|---|
| Test 29 | 4 | n.d. | 4 | n.d. | 4 |
| Test Blank | 1 | n.d. | 1 | n.d. | 1 |

EXAMPLE 30

A 1 L round bottom flask equipped with a condensor was placed under a $N_2$ atmosphere and charged with propylene imine (80.0 gram), n-butyl glycidyl ether (126.0 gram) and $K_2CO_3$ (10.00 gram) and heated to 80° C. in 30 min, after which the mixture was stirred for 21 h at T=80° C. After filtration the excess of PI was removed in vacuo, followed by further purification via vacuum distillation, resulting in a colorless low viscous liquid.

A 500 mL round bottom flask equipped with a thermometer and overhead stirrer was placed under a $N_2$ atmosphere and charged with Desmodur W (54.63 gram) and 38.99 gram of the product of the previous step. The resulting mixture was heated to 50° C., after which bismuth neodecanoate (0.05 gram) was added. The mixture was allowed to exotherm followed by further heating to 80° C. and stirring for 1 hour at 80° C. To the mixture was then added PPG1000 (106.33 gram) and the mixture was stirred for another 1 hour at 80° C. The solvent was removed in vacuo to obtain a colorless solid.

Subsequently, 30 grams of the colorless solid obtained in the previous step was mixed with 15 grams of acetone and incubated at 50° C. until a homogeneous solution was obtained. To this solution was added 0.03 grams of triethylamine (TEA) and then 3 grams of molten Maxemul™ 7101 dispersant. The resulting mixture was stirred for 5 minutes at room temperature using an IKA T25 Digital Ultra-Turrax® mixer with S 25 N-18G head at 2,000 rpm. Then, stirring was increased to 10,000 rpm and 30 grams of demineralized water, brought to pH 11 using triethylamine, was added gradually to the mixture over 15 minutes. During this addition process, the mixer was moved around the reaction vessel continuously. After completion of the addition, the resulting dispersion was stirred at 5,000 rpm for 10 more minutes, and the pH of the dispersion was set to 11 with TEA.

Functional performance and stability of the crosslinker dispersion were assessed using spot tests on coating surfaces, based on procedures from the DIN 68861-1 standard, and viscosity measurements as well as particle size measurements. For these tests, the crosslinker dispersion was stored in an oven at 50° C. for 4 weeks. Every week, the viscosity and the particle size of the crosslinker dispersion were determined. Additionally, every week, 5.3 grams of the aged crosslinker dispersion was mixed with 21 grams of Polymer P1 under continuous stirring, and the resulting mixture was further stirred for 30 minutes. This coating composition was filtered and applied to Leneta test cards using 100 μm wire rod applicators (Test 30). For reference, films were also cast from the same composition lacking the crosslinker dispersion (Test Blank). The films were dried for 1 hour at 25° C., then annealed at 50° C. for 16 hours. Subsequently, a piece of cotton wool was soaked in 1:1 EtOH:demineralized water and placed on the film for 1 hour. After removal of the EtOH and 60 minutes recovery, the following results were obtained (a score of 1 indicates complete degradation of the film, 5 indicates no damage visible):

Performance and Stability Test

| Sample | Week 0 | Week 1 | Week 2 | Week 3 | Week 4 |
|---|---|---|---|---|---|
| Particle size 30 (nm) | 244 | 207 | n.d. | 219 | 206 |
| Viscosity 30 (mPa·s) | 89 | 91 | n.d. | 88 | 109 |
| Test 30 | 4 | 4 | n.d. | 3 | 3 |
| Test Blank | 1 | 1 | n.d. | 1 | 1 |

EXAMPLE 31

The (1-butoxy-3-(2-methylaziridin-1-yl)propan-2-ol) intermediate was prepared as described in Example 1. A 500 mL round bottom flask equipped with a thermometer and overhead stirrer was placed under a $N_2$ atmosphere and charged with Desmodur W (54.67 gram) and 39.03 grams of the (1-butoxy-3-(2-methylaziridin-1-yl)propan-2-ol) intermediate. The resulting mixture was heated to 50° C., after which bismuth neodecanoate (0.02 gram) was added. The mixture was allowed to exotherm followed by further heating to 80° C. and stirring for 1 hour at 80° C. To the mixture was then added Durez-Ter S 105-110 (106.26 gram) and the mixture was stirred for another 1 hour at 80° C. Then, samples were taken at regular intervals and the reaction progress was monitored using a Bruker Alpha FT-IR spectrometer until no NCO-stretch at 2200-2300 $cm^{-1}$ was observed. The solvent was removed in vacuo to obtain a colorless solid.

Subsequently, 30 grams of the colorless solid obtained in the previous step was mixed with 15 grams of acetone and incubated at 50° C. until a homogeneous solution was obtained. To this solution was added 0.03 grams of triethylamine (TEA) and then 3 grams of molten Maxemul™ 7101 dispersant. The resulting mixture was stirred for 5 minutes at room temperature using an IKA T25 Digital Ultra-Turrax® mixer with S 25 N-18G head at 2,000 rpm. Then, stirring was increased to 10,000 rpm and 30 grams of demineralized water, brought to pH 11 using triethylamine, was added gradually to the mixture over 15 minutes. During this addition process, the mixer was moved around the reaction vessel continuously. After completion of the addition, the resulting dispersion was stirred at 5,000 rpm for 10 more minutes, and the pH of the dispersion was set to 11 with TEA.

Functional performance and stability of the crosslinker dispersion were assessed using spot tests on coating surfaces, based on procedures from the DIN 68861-1 standard, and viscosity measurements as well as particle size measurements. For these tests, the crosslinker dispersion was stored in an oven at 50° C. for 4 weeks. Every week, the viscosity and the particle size of the crosslinker dispersion were determined. Additionally, every week, 5.3 grams of the aged crosslinker dispersion was mixed with 21 grams of Polymer P1 under continuous stirring, and the resulting mixture was further stirred for 30 minutes. This coating composition was filtered and applied to Leneta test cards using 100 μm wire rod applicators (Test 31). For reference, films were also cast from the same composition lacking the crosslinker dispersion (Test Blank). The films were dried for 1 hour at 25° C., then annealed at 50° C. for 16 hours. Subsequently, a piece of cotton wool was soaked in 1:1 EtOH:demineralized water and placed on the film for 1 hour. After removal of the EtOH and 60 minutes recovery, the following results were obtained (a score of 1 indicates complete degradation of the film, 5 indicates no damage visible):

Performance and Stability Test

| Sample | Week 0 | Week 1 | Week 2 | Week 3 | Week 4 |
|---|---|---|---|---|---|
| Particle size 31 (nm) | 303 | 300 | n.d. | 297 | 300 |
| Viscosity 31 (mPa · s) | 38 | 22 | n.d. | 32 | 33 |
| Test 31 | 4 | 4 | n.d. | 3 | 3 |
| Test Blank | 1 | 1 | n.d. | 1 | 1 |

EXAMPLE 32

A 1 L round bottom flask equipped with a thermometer and overhead stirrer was placed under a $N_2$ atmosphere and charged with (1-butoxy-3-(2-methylaziridin-1-yl)propan-2-ol) intermediate prepared as described in Example 1 (25.12 gram), Desmodur W (55.30 gram), Ymer N120 (18.21 grams) and 51.36 grams of polytetrahydrofuran with an average Mn of 650 Da (pTHF650). The resulting mixture was heated to 50° C., after which bismuth neodecanoate (0.02 gram) was added. The mixture was allowed to exotherm followed by further heating to 70° C. and stirring until a residual NCO level of 3.8% was reached. The mixture was then cooled to 60° C. and 50.0 grams of acetone was added followed by further cooling to 40° C. To the mixture was then added Vestamin A-95 (8.31 gram), flushed with 15 grams of demineralized water and 1.5 grams of 15% aqueous potassium hydroxide solution, and the mixture was heated to 50° C. and stirred for another 15 minutes. Then, 280 grams of demineralized water and 9.5 grams of 10% aqueous sodium sulfate solution were added. The solvent was removed in vacuo to obtain a whitish dispersion. The dispersion was filtered, set to 34% solids using demineralized water and set to pH 11 with aqueous potassium hydroxide.

Functional performance and stability of the crosslinker dispersion were assessed using spot tests on coating surfaces, based on procedures from the DIN 68861-1 standard, and viscosity measurements as well as particle size measurements. For these tests, the crosslinker dispersion was stored in an oven at 50° C. for 4 weeks. Every week, the viscosity and the particle size of the crosslinker dispersion were determined. Additionally, every week, 7.2 grams of the aged crosslinker dispersion was mixed with 21 grams of Polymer P1 under continuous stirring, and the resulting mixture was further stirred for 30 minutes. This coating composition was filtered and applied to Leneta test cards using 100 µm wire rod applicators (Test 32). For reference, films were also cast from the same composition lacking the crosslinker dispersion (Test Blank). The films were dried for 1 hour at 25° C., then annealed at 50° C. for 16 hours. Subsequently, a piece of cotton wool was soaked in 1:1 EtOH:demineralized water and placed on the film for 1 hour. After removal of the EtOH and 60 minutes recovery, the following results were obtained (a score of 1 indicates complete degradation of the film, 5 indicates no damage visible):

Performance and Stability Test

| Sample | Week 0 | Week 1 | Week 2 | Week 3 | Week 4 |
|---|---|---|---|---|---|
| Particle size 32 (nm) | 129 | 111 | 119 | 115 | 129 |
| Viscosity 32 (mPa · s) | 87 | 66 | 75 | 105 | 172 |
| Test 32 | 3 | 3 | 3 | 3 | 3 |
| Test Blank | 1 | 1 | 1 | 1 | 1 |

EXAMPLE 33

The (1-butoxy-3-(2-methylaziridin-1-yl)propan-2-ol) intermediate was prepared as described in Example 1. A 500 mL round bottom flask equipped with a thermometer and overhead stirrer was placed under a $N_2$ atmosphere and charged with Desmodur W (88.03 gram) and 62.84 grams of the (1-butoxy-3-(2-methylaziridin-1-yl)propan-2-ol) intermediate. At room temperature, bismuth neodecanoate (0.02 gram) was added. The mixture was allowed to exotherm followed by further heating to 60° C. over the course of 1 hour. To the mixture was then added Voranol CP450 (49.13 gram) and 50.0 grams of acetone, and the mixture was stirred for another 4 hours at 60° C. Then, samples were taken at regular intervals and the reaction progress was monitored using a Bruker Alpha FT-IR spectrometer until no NCO-stretch at 2200-2300 $cm^{-1}$ was observed. This procedure yielded a low viscous, slightly yellowish solution.

Subsequently, 15.4 grams of the low viscous, slightly yellowish solution obtained in the previous step was mixed with 3.4 grams of acetone and incubated at 50° C. until a homogeneous solution was obtained. To this solution was added 0.03 grams of triethylamine (TEA) and then 1.3 grams of molten Maxemul™ 7101 dispersant. The resulting mixture was stirred for 5 minutes at room temperature using an IKA T25 Digital Ultra-Turrax® mixer with S 25 N-18G head at 2,000 rpm. Then, stirring was increased to 10,000 rpm and 12.6 grams of demineralized water, brought to pH 11 using triethylamine, was added gradually to the mixture over 15 minutes. During this addition process, the mixer was moved around the reaction vessel continuously. After completion of the addition, the resulting dispersion was stirred at 5,000 rpm for 10 more minutes, and the pH of the dispersion was set to 11 with TEA.

Functional performance and stability of the crosslinker dispersion were assessed using spot tests on coating surfaces, based on procedures from the DIN 68861-1 standard, and viscosity measurements as well as particle size measurements. For these tests, the crosslinker dispersion was stored in an oven at 50° C. for 4 weeks. Every week, the viscosity and the particle size of the crosslinker dispersion were determined. Additionally, every week, 1.6 grams of the aged crosslinker dispersion was mixed with 10.5 grams of Polymer P1 under continuous stirring, and the resulting mixture was further stirred for 30 minutes. This coating composition was filtered and applied to Leneta test cards using 100 µm wire rod applicators (Test 33). For reference, films were also cast from the same composition lacking the crosslinker dispersion (Test Blank). The films were dried for 1 hour at 25° C., then annealed at 50° C. for 16 hours. Subsequently, a piece of cotton wool was soaked in 1:1 EtOH:demineralized water and placed on the film for 1 hour. After removal of the EtOH and 60 minutes recovery, the following results were obtained (a score of 1 indicates complete degradation of the film, 5 indicates no damage visible):

Performance and Stability Test

| Sample | Week 0 | Week 1 | Week 2 | Week 3 | Week 4 |
|---|---|---|---|---|---|
| Particle size 33 (nm) | 272 | n.d. | 277 | n.d. | 278 |
| Viscosity 33 (mPa · s) | 35 | n.d. | 34 | n.d. | 38 |
| Test 33 | 3 | n.d. | 3 | n.d. | 3 |
| Test Blank | 1 | n.d. | 1 | n.d. | 1 |

EXAMPLE 34

A 2 L round bottom flask equipped with a condenser was placed under a $N_2$ atmosphere and charged with toluene (250 gram), propylene imine (325 gram), Bisphenol A-diglycidyl ether (387 gram) and $K_2CO_3$ (10.0 gram) and heated to 70° C. in 30 min, after which the mixture was stirred for 19 h at T=70° C. After filtration the excess of PI was removed in vacuo, followed by further purification via vacuum distillation, resulting in a whitish solid.

A 500 mL round bottom flask equipped with a thermometer and overhead stirrer was placed under a $N_2$ atmosphere and charged with the Bisphenol A-PI intermediate from the first step (34.15 gram), (1-butoxy-3-(2-methylaziridin-1-yl) propan-2-ol) intermediate prepared as described in Example 1 (25.32 gram), Desmodur W (39.41 gram) and 22.83 grams of acetone. The resulting mixture was heated to 50° C., after which bismuth neodecanoate (0.02 gram) was added. The mixture was allowed to exotherm to 60° C. followed by stirring for 2 hours at 60° C. Samples were taken at regular intervals and the reaction progress was monitored using a Bruker Alpha FT-IR spectrometer until no change in NCO-stretch at 2200-2300 $cm^{-1}$ was observed. Subsequently, 1.11 grams of n-butanol was added to the reaction mixture. The reaction mixture was then further reacted to complete disappearance of aforementioned NCO-stretch peak. Finally, 32.00 grams of acetone were added to yield a light yellow solution.

The calculated molecular weights of the theoretical main components and their chemical structures are shown below:

stirred for 5 minutes at room temperature using an IKA T25 Digital Ultra-Turrax® mixer with S 25 N-18G head at 2,000 rpm. Then, stirring was increased to 10,000 rpm and 18.9 grams of demineralized water, brought to pH 11 using triethylamine, was added gradually to the mixture over 15 minutes. During this addition process, the mixer was moved around the reaction vessel continuously. After completion of the addition, the resulting dispersion was stirred at 5,000 rpm for 10 more minutes, and the pH of the dispersion was set to 11 with TEA.

Functional performance and stability of the crosslinker dispersion were assessed using spot tests on coating surfaces, based on procedures from the DIN 68861-1 standard, and viscosity measurements as well as particle size measurements. For these tests, the crosslinker dispersion was stored in an oven at 50° C. for 4 weeks. Every week, the viscosity and the particle size of the crosslinker dispersion were determined. Additionally, every week, 1.0 grams of the aged crosslinker dispersion was mixed with 10.5 grams of Polymer P1 under continuous stirring, and the resulting mixture was further stirred for 30 minutes. This coating composition was filtered and applied to Leneta test cards using 100 µm wire rod applicators (Test 34). For reference, films were also cast from the same composition lacking the crosslinker dispersion (Test Blank). The films were dried for 1 hour at 25° C., then annealed at 50° C. for 16 hours. Subsequently, a piece of cotton wool was soaked in 1:1 EtOH:demineralized water and placed on the film for 1 hour. After removal of the EtOH and 60 minutes recovery, the

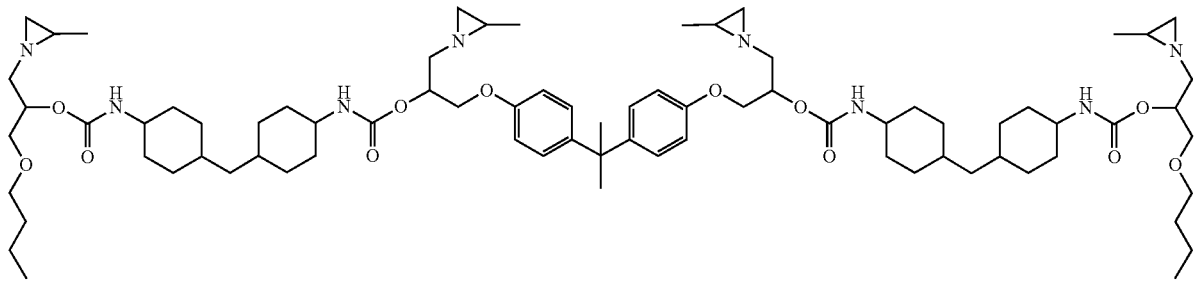 [SMILES: CCCCOCC(CN1CC1C)OC(=O)NC1CCC(CC2CCC(NC(=O)OC(COc3ccc(C(C)(C)c4ccc(OCC(CN5CC5C)OC(=O)NC5CCC(CC6CCC(NC(=O)OC(COCCCC)CN7CC7C)CC6)CC5)cc4)cc3)CN3CC3C)CC2)CC1]

Molecular weight was confirmed by Maldi-TOF-MS: Calcd. [M+Na+]=1375.92 Da; Obs. [M+Na+]=1375.91 Da.

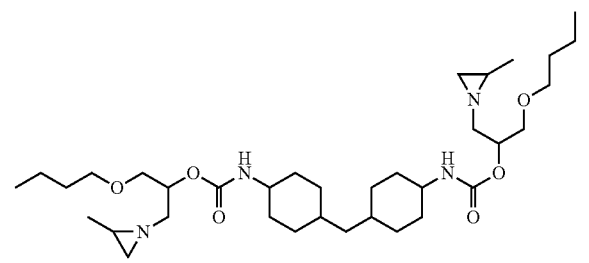 [SMILES: CCCCOCC(CN1CC1C)OC(=O)NC1CCC(CC2CCC(NC(=O)OC(COCCCC)CN3CC3C)CC2)CC1]

Molecular weight was confirmed by Maldi-TOF-MS: Calcd. [M+Na+]=659.47 Da; Obs. [M+Na+]=659.44 Da.

Subsequently, 27 grams of the yellow solution obtained in the previous step was mixed with 3.6 grams of methyl ethyl ketone (MEK) and incubated at 50° C. until a homogeneous solution was obtained. To this solution was added 0.03 grams of triethylamine (TEA) and then 1.8 grams of molten Maxemul™ 7101 dispersant. The resulting mixture was following results were obtained (a score of 1 indicates complete degradation of the film, 5 indicates no damage visible):

Performance and Stability Test

| Sample | Week 0 | Week 1 | Week 2 | Week 3 | Week 4 |
|---|---|---|---|---|---|
| Particle size 34 (nm) | 368 | 373 | 312 | 332 | 347 |
| Viscosity 34 (mPa · s) | 87 | 80 | 82 | 82 | 88 |
| Test 34 | 4 | 4 | 4 | 3 | 3 |
| Test Blank | 1 | 1 | 1 | 1 | 1 |

EXAMPLE 35

A 500 mL round bottom flask equipped with a thermometer and overhead stirrer was placed under a $N_2$ atmosphere and charged with the Bisphenol A-PI intermediate prepared as described in Example 34 (31.74 gram), (1-butoxy-3-(2-methylaziridin-1-yl)propan-2-ol) intermediate prepared as described in Example 1 (18.73 gram), Desmodur W (35.14 gram) and 22.83 grams of acetone. The resulting mixture was heated to 50° C., after which bismuth neodecanoate (0.02 gram) was added. The mixture was allowed to exotherm to 60° C. followed by stirring for 80 minutes at 60° C. Samples were taken at regular intervals and the reaction progress was monitored using a Bruker Alpha FT-IR spectrometer until no change in NCO-stretch at 2200-2300 cm$^{-1}$ was observed. Subsequently, 14.39 grams of Ymer N120 was added to the reaction mixture. The reaction mixture was then further reacted to complete disappearance of aforementioned NCO-stretch peak, and then 25.00 grams of acetone were added to dilute the reaction mixture. Subsequently, the mixture was cooled to 40° C. and 170 grams of demineralized water was added gradually, yielding a bluish dispersion. The acetone was then removed from the dispersion using a rotary evaporator, and finally the pH of the dispersion was set to 11 using triethylamine.

The calculated molecular weights of the theoretical main components and their chemical structures are shown below:

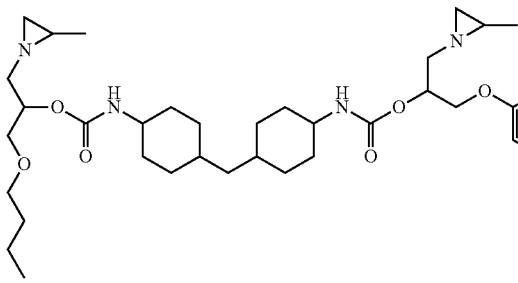
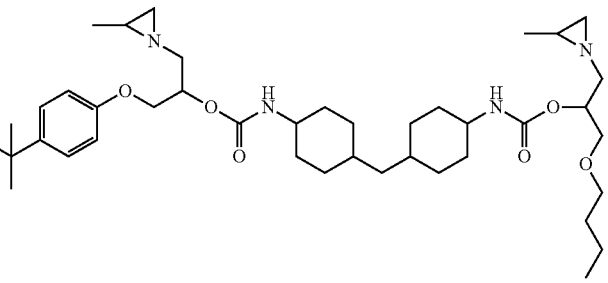

Molecular weight was confirmed by Maldi-TOF-MS: Calcd. [M+Na+]=1375.92 Da; Obs. [M+Na+]=1375.88 Da.

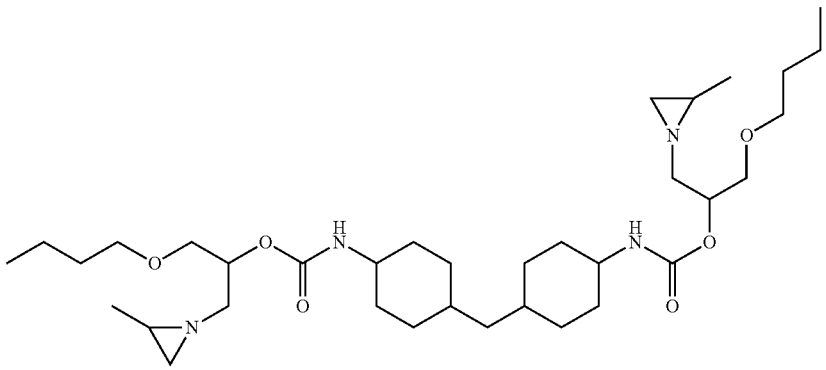 [SMILES: CCCCOCC(CN1CC1C)OC(=O)NC1CCC(CC2CCC(NC(=O)OC(COCCCC)CN3CC3C)CC2)CC1]

Molecular weight was confirmed by Maldi-TOF-MS: Calcd. [M+Na+]=659.47 Da; Obs. [M+Na+]=659.44 Da.

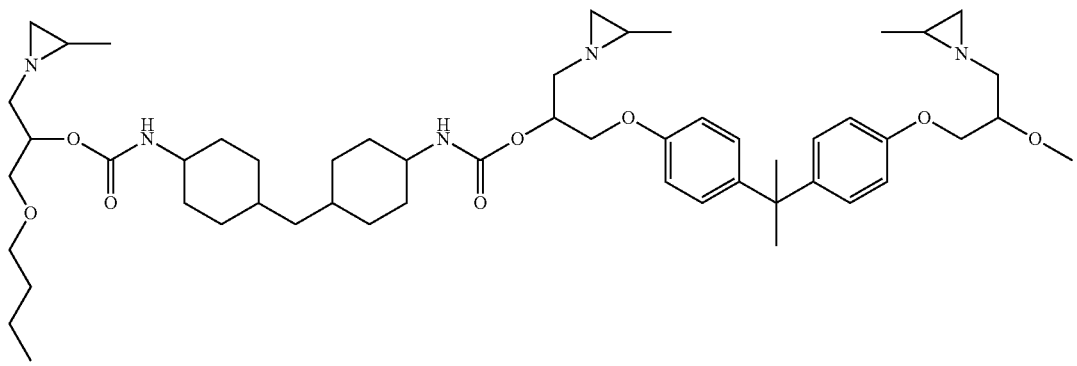

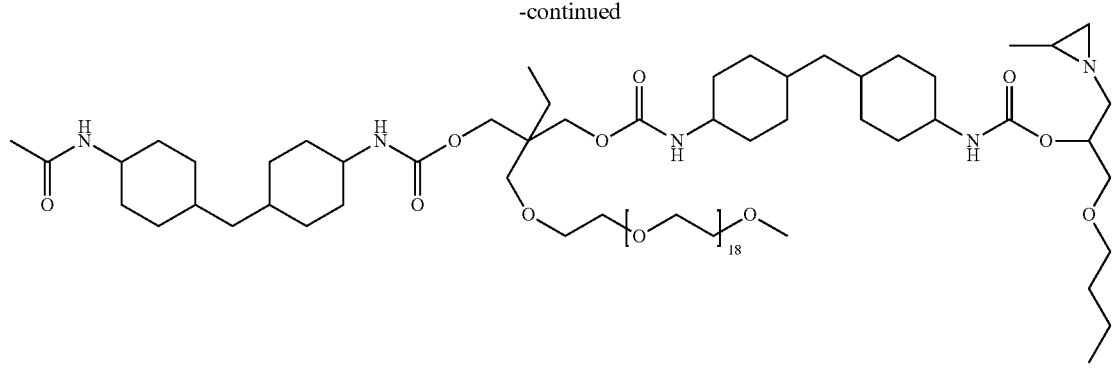

Molecular weight was confirmed by Maldi-TOF-MS: Calcd. [M+Na+]=2622.70 Da; Obs. [M+Na+]=2622.54 Da.

Functional performance and stability of the crosslinker dispersion were assessed using spot tests on coating surfaces, based on procedures from the DIN 68861-1 standard, and viscosity measurements as well as particle size measurements. For these tests, the crosslinker dispersion was stored in an oven at 50° C. for 4 weeks. Every week, the viscosity and the particle size of the crosslinker dispersion were determined. Additionally, every week, 1.8 grams of the aged crosslinker dispersion was mixed with 21 grams of Polymer P1 under continuous stirring, and the resulting mixture was further stirred for 30 minutes. This coating composition was filtered and applied to Leneta test cards using 100 μm wire rod applicators (Test 35). For reference, films were also cast from the same composition lacking the crosslinker dispersion (Test Blank). The films were dried for 1 hour at 25° C., then annealed at 50° C. for 16 hours. Subsequently, a piece of cotton wool was soaked in 1:1 EtOH:demineralized water and placed on the film for 1 hour. After removal of the EtOH and 60 minutes recovery, the following results were obtained (a score of 1 indicates complete degradation of the film, 5 indicates no damage visible):

Performance and Stability Test

| Sample | Week 0 | Week 1 | Week 2 | Week 3 | Week 4 |
| --- | --- | --- | --- | --- | --- |
| Particle size 35 (nm) | 85 | 88 | 97 | 94 | 90 |
| Viscosity 35 (mPa · s) | 572 | 546 | 562 | 582 | 540 |
| Test 35 | 3 | 3 | 3 | 3 | 3 |
| Test Blank | 1 | 1 | 1 | 1 | 1 |

EXAMPLE 36

A 500 mL round bottom flask equipped with a thermometer and overhead stirrer was placed under a $N_2$ atmosphere and charged with the Bisphenol A-PI intermediate prepared as described in Example 34 (17.13 gram), (1-butoxy-3-(2-methylaziridin-1-yl)propan-2-ol) intermediate prepared as described in Example 1 (28.24 gram), Desmodur W (39.55 gram) and 25.00 grams of acetone. The resulting mixture was heated to 60° C., after which bismuth neodecanoate (0.02 gram) was added. The mixture was kept at 60° C. using a water bath throughout the exothermic reaction, followed by stirring for 2 hours at 60° C. Samples were taken at regular intervals and the reaction progress was monitored using a Bruker Alpha FT-IR spectrometer until no change in NCO-stretch at 2200-2300 $cm^{-1}$ was observed. Subsequently, 15.08 grams of Voranol P-400 was added to the reaction mixture. The reaction mixture was then further reacted to complete disappearance of aforementioned NCO-stretch peak. Finally, 20.00 grams of acetone were added to yield a light yellow solution. The calculated molecular weights of the theoretical main components and their chemical structures are shown below:

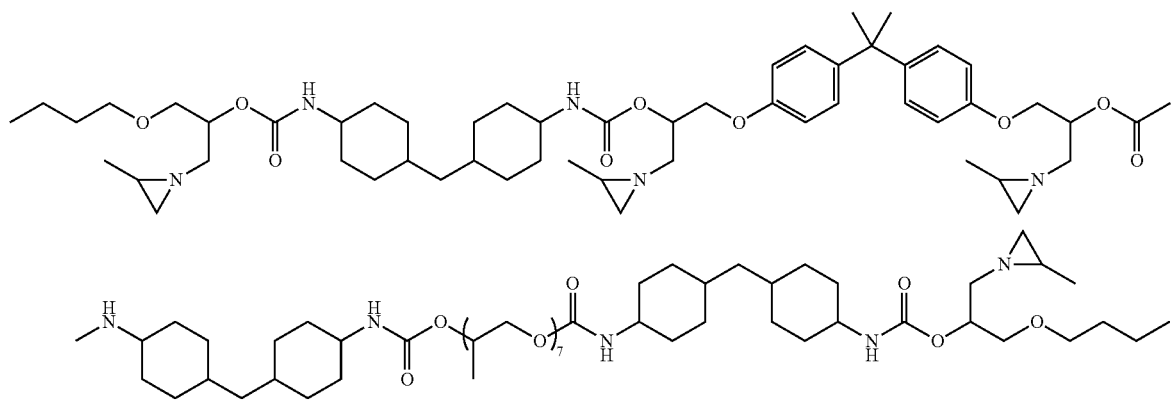

Molecular weight was confirmed by Maldi-TOF-MS: Calcd. [M+Na+]=2062.40 Da; Obs. [M+Na+]=2062.39 Da.

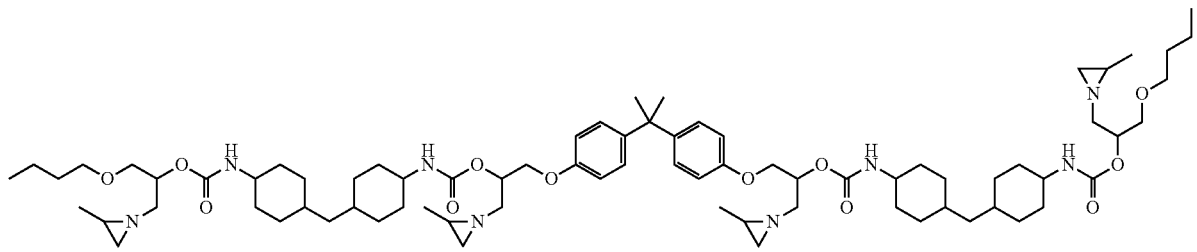 [SMILES: CCCCOCC(CN1CC1C)OC(=O)NC1CCC(CC2CCC(NC(=O)OC(COc3ccc(C(C)(C)c4ccc(OCC(CN5CC5C)OC(=O)NC5CCC(CC6CCC(NC(=O)OC(COCCCC)CN7CC7C)CC6)CC5)cc4)cc3)CN3CC3C)CC2)CC1]

Molecular weight was confirmed by Maldi-TOF-MS: Calcd. [M+Na+]=1375.92 Da; Obs. [M+Na+]=1375.86 Da.

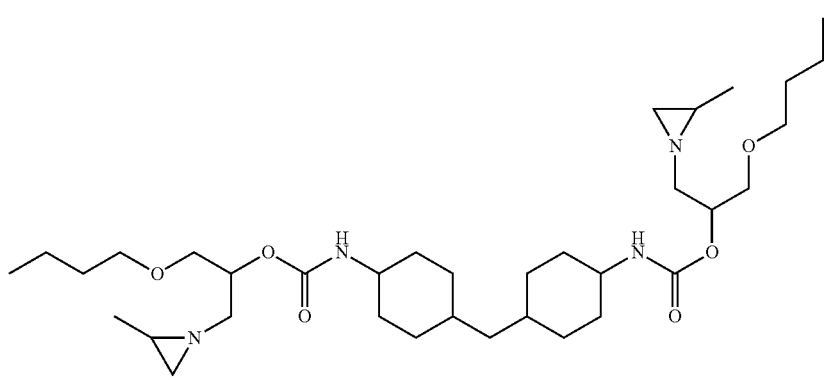 [SMILES: CCCCOCC(CN1CC1C)OC(=O)NC1CCC(CC2CCC(NC(=O)OC(COCCCC)CN3CC3C)CC2)CC1]

Molecular weight was confirmed by Maldi-TOF-MS: Calcd. [M+Na+]=659.47 Da; Obs. [M+Na+]=659.41 Da.

The following components with a mass below 580 Da were determined by LC-MS and quantified:

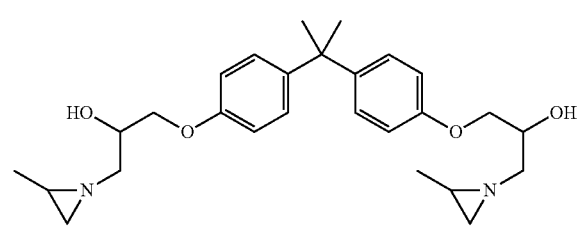 [SMILES: CC1CN1CC(O)COc1ccc(C(C)(C)c2ccc(OCC(O)CN3CC3C)cc2)cc1]

was present in the composition at less than 0.01 wt. % and

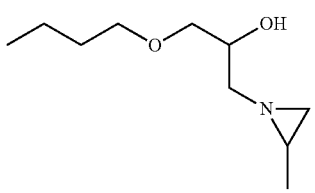

was present at less than 0.01 wt. %.

Genotoxicity Test

| | Without S9 rat liver extract | | | | | | With S9 rat liver extract | | | | | |
|---|---|---|---|---|---|---|---|---|---|---|---|---|
| | Bscl 2 | | | Rtkn | | | Bscl 2 | | | Rtkn | | |
| | \multicolumn{12}{c}{concentration} | | | | | | | | | | | |
| | 10 | 25 | 50 | 10 | 25 | 50 | 10 | 25 | 50 | 10 | 25 | 50 |
| Composition 36 | 1.2 | 1.3 | 1.6 | 1.2 | 1.2 | 1.3 | 1.4 | 1.6 | 1.8 | 1.2 | 1.3 | 1.6 |

The genotoxicity test results show that the crosslinker composition of Example 36 only has weakly positive induced genotoxicity.

Subsequently, 15 grams of the yellow solution obtained in the previous step was mixed with 1.5 grams of methyl ethyl ketone (MEK) and incubated at 50° C. until a homogeneous solution was obtained. To this solution was added 0.03 grams of triethylamine (TEA) and then 1.1 grams of Atlas™ G-5002L-LQ dispersant. The resulting mixture was stirred for 5 minutes at room temperature using an IKA T25 Digital Ultra-Turrax® mixer with S 25 N-18G head at 2,000 rpm. Then, stirring was increased to 10,000 rpm and 10.4 grams of demineralized water, brought to pH 11 using triethylamine, was added gradually to the mixture over 15 minutes. During this addition process, the mixer was moved around the reaction vessel continuously. After completion of the addition, the resulting dispersion was stirred at 5,000 rpm for 10 more minutes, and the pH of the dispersion was set to 11 with TEA.

Functional performance and stability of the crosslinker dispersion were assessed using spot tests on coating surfaces, based on procedures from the DIN 68861-1 standard, and viscosity measurements as well as particle size measurements. For these tests, the crosslinker dispersion was stored in an oven at 50° C. for 4 weeks. Every week, the viscosity and the particle size of the crosslinker dispersion were determined. Additionally, every week, 1.2 grams of the aged crosslinker dispersion was mixed with 10.5 grams of Polymer P1 under continuous stirring, and the resulting mixture was further stirred for 30 minutes. This coating composition was filtered and applied to Leneta test cards using 100 μm wire rod applicators (Test 36). For reference, films were also cast from the same composition lacking the crosslinker dispersion (Test Blank). The films were dried for 1 hour at 25° C., then annealed at 50° C. for 16 hours. Subsequently, a piece of cotton wool was soaked in 1:1 EtOH:demineralized water and placed on the film for 1 hour. After removal of the EtOH and 60 minutes recovery, the following results were obtained (a score of 1 indicates complete degradation of the film, 5 indicates no damage visible):

Performance and Stability Test

| Sample | Week 0 | Week 1 | Week 2 | Week 3 | Week 4 |
|---|---|---|---|---|---|
| Particle size 36 (nm) | 206 | 200 | 199 | 202 | 215 |
| Viscosity 36 (mPa · s) | 178 | 230 | 205 | 231 | 288 |
| Test 36 | 3 | 3 | 3 | 3 | 3 |
| Test Blank | 1 | 1 | 1 | 1 | 1 |

COMPARATIVE EXAMPLE C10

Under a nitrogen atmosphere, 21.3 grams of 1-propanol was added over a period of 6 hours to 78.7 grams of isophorone diisocyanate (IPDI) and 0.01 grams of tin 2-ethyl hexanoate at 20-25° C., while stirring. After standing overnight, 196.3 grams of IPDI, 74.1 grams of Tegomer D3403 and 2.4 grams of 3-Methyl-1-phenyl-2-phospholene-1-oxide were added. The mixture was heated to 150° C. while stirring. The mixture was kept at 150° C. until NCO content was 7.0 wt %. Mixture was cooled to 80° C. and 333 grams of 1-methoxy-2-propyl acetate (MPA) was added. A solution of isocyanate functional polycarbodiimide was obtained with a solid content of 50.6 wt % and an NCO content of 7.0 wt % on solids.

To 100 grams of this isocyanate functional polycarbodiimide was added 7.0 grams of 1-(2-hydroxyethyl)ethyleneimine. One drop of dibutyltin dilaurate was added. The mixture was heated to 80° C. while stirring. The mixture was kept at 80° C. for 1 hour. FTIR showed a small remaining isocyanate signal, which disappeared after a few days. The solution was further diluted with 8.0 grams of MPA, resulting in a yellow solution with a solid content of 50.4 wt %. This aziridine functional carbodiimide contains 3.2 meq acid reactive groups (i.e aziridine and carbodiimide functionality) per gram solids.

The generalized structure of this carbodiimide is depicted below.

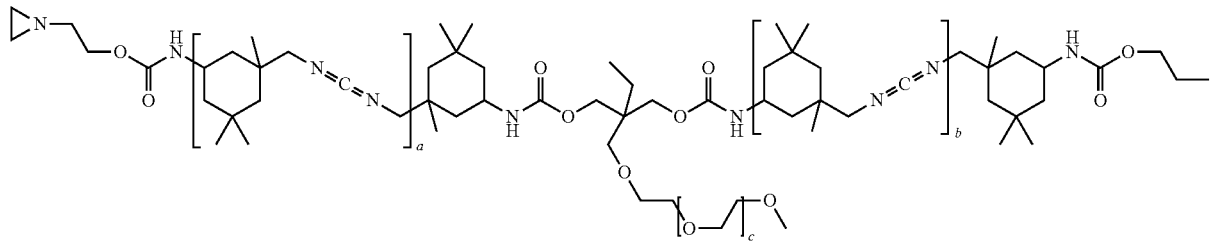

in which a, b and c indicates repeating units.

This generalized structure was confirmed by MALDI-TOF-MS, an example is shown below:

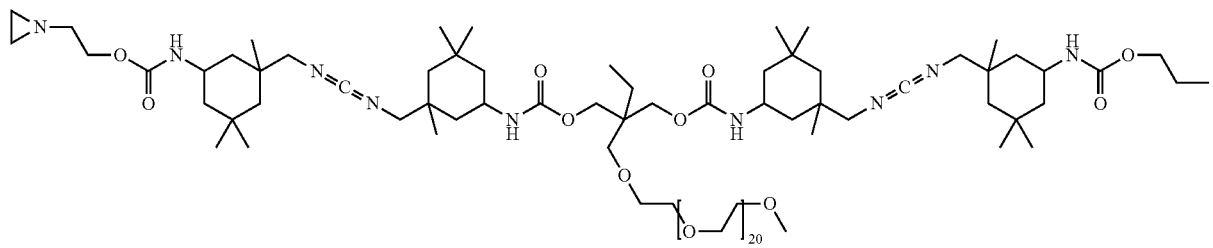

Molecular weight was confirmed by Maldi-TOF-MS: Calcd. [M+Na+]=2043.34 Da; Obs. [M+Na+]=2043.32 Da.

Genotoxicity Test Results:

|  | Without S9 rat liver extract | | | | | | With S9 rat liver extract | | | | | |
|---|---|---|---|---|---|---|---|---|---|---|---|---|
|  | Bscl 2 | | | Rtkn | | | Bscl 2 | | | Rtkn | | |
|  | concentration | | | | | | | | | | | |
|  | 10 | 25 | 50 | 10 | 25 | 50 | 10 | 25 | 50 | 10 | 25 | 50 |
| Composition C10 | 1.3 | 1.5 | 1.6 | 1.2 | 1.9 | 1.9 | 1.2 | 1.4 | 1.5 | 2.0 | 2.0 | 1.8 |

The genotoxicity test results demonstrate that the crosslinker composition of Comparative Example C10 is genotoxic.

Subsequently, 25.0 grams of the yellow solution obtained in the previous step was stirred for at room temperature using a three-bladed propeller stirrer with diameter 50 mm at 500 rpm. Then, 25.0 grams of demineralized water was added gradually to the mixture over 15 minutes. After completion of the addition, the resulting dispersion was stirred at 500 rpm for 5 more minutes.

Functional performance and stability of the crosslinker dispersion were assessed using spot tests on coating surfaces, based on procedures from the DIN 68861-1 standard, and viscosity measurements as well as particle size measurements. For these tests, the crosslinker dispersion was stored in an oven at 50° C. for 4 weeks. Every week, the viscosity and the particle size of the crosslinker dispersion were determined. Additionally, every week, 5.1 grams of the aged crosslinker dispersion was mixed with 10.5 grams of Polymer P1 under continuous stirring, and the resulting mixture was further stirred for 30 minutes. This coating composition was filtered and applied to Leneta test cards using 100 μm wire rod applicators (Test C10). For reference, films were also cast from the same composition lacking the crosslinker dispersion (Test Blank). The films were dried for 1 hour at 25° C., then annealed at 50° C. for 16 hours. Subsequently, a piece of cotton wool was soaked in 1:1 EtOH:demineralized water and placed on the film for 1 hour. After removal of the EtOH and 60 minutes recovery, the following results were obtained (a score of 1 indicates complete degradation of the film, 5 indicates no damage visible):

Performance and Stability Test

| Sample | Week 0 | Week 1 | Week 2 | Week 3 | Week 4 |
|---|---|---|---|---|---|
| Particle size C10 (nm) | 76 | —* | —* | —* | —* |
| Viscosity C10 (mPa · s) | 812 | —* | —* | —* | —* |
| Test C10 | 4 | —* | —* | —* | —* |
| Test Blank | 1 | 1 | 1 | 1 | 1 |

*The 1-(2-hydroxyethyl)ethyleneimine based crosslinker mixture coagulated during first week of storage

COMPARATIVE EXAMPLE C11

A 1 L round bottom flask equipped with a thermometer and overhead stirrer was placed under a $N_2$ atmosphere and charged with 196.1 grams of polytetrahydrofuran with an average Mn of 1000 Da (pTHF1000) and 200.0 grams of o-xylene. The resulting mixture was cooled to −10° C. using ethanol and ice, after which a solution of 68.4 grams of toluene diisocyanate (TDI) in 50.0 grams of o-xylene was added. The mixture was allowed to exotherm bringing the mixture to −1° C., followed by a gradual rise to room temperature without added heating. The reaction was continued to full conversion (residual NCO of 3.2%), and 200 grams of the resulting reaction mixture was transferred to a 500 mL round bottom flask equipped with a thermometer and overhead stirrer under a $N_2$ atmosphere. To this mixture was then added 14.5 grams of 1-(2-hydroxyethyl)ethyleneimine over 60 minutes, maintaining room temperature using a water bath. The mixture was then stirred for 1 hour at 25° C. Then, samples were taken at regular intervals and the reaction progress was monitored using a Bruker Alpha FT-IR spectrometer until no NCO-stretch at 2200-2300 $cm^{-1}$ was observed. Solids was set to 49% using further o-xylene, resulting in a slightly turbid low-viscous solution.

The calculated molecular weights of the theoretical main components and their chemical structures are shown below:

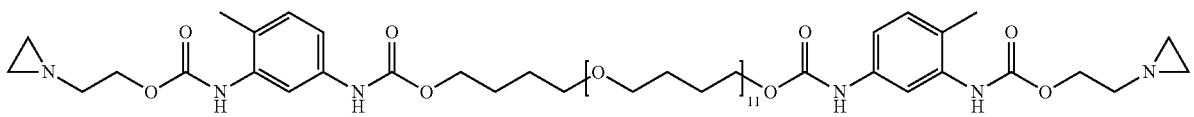

Molecular weight was confirmed by Maldi-TOF-MS: Calcd. [M+Na+]=1427.91 Da; Obs. [M+Na+]=1428.02 Da.

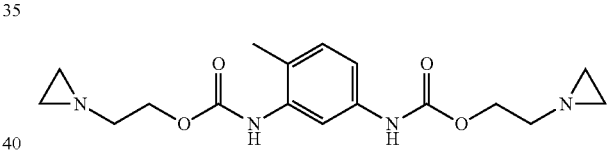

Molecular weight was confirmed by Maldi-TOF-MS: Calcd. [M+Na+]=371.17 Da; Obs. [M+Na+]=371.21 Da.

Subsequently, 18.0 grams of the low-viscous solution obtained as described above was mixed with 1.5 grams of Triton X-100 and incubated at 50° C. until a homogeneous solution was obtained. The resulting mixture was stirred for 30 minutes at room temperature using a three-bladed propeller stirrer with diameter 50 mm at 500 rpm.

Then, stirring was increased to 800 rpm and 15.0 grams of demineralized water was added gradually to the mixture over 15 minutes. After completion of the addition, the resulting dispersion was stirred at 500 rpm for 10 more minutes.

Functional performance and stability of the crosslinker dispersion were assessed using spot tests on coating surfaces, based on procedures from the DIN 68861-1 standard, and viscosity measurements as well as particle size measurements. For these tests, the crosslinker dispersion was stored in an oven at 50° C. for 4 weeks. Every week, the viscosity and the particle size of the crosslinker dispersion were determined. Additionally, every week, 2.8 grams of the aged crosslinker dispersion was mixed with 10.5 grams of Polymer P1 under continuous stirring, and the resulting mixture was further stirred for 30 minutes. This coating composition was filtered and applied to Leneta test cards using 100 μm wire rod applicators (Test C11). For reference, films were also cast from the same composition lacking the crosslinker dispersion (Test Blank). The films were dried for 1 hour at 25° C., then annealed at 50° C. for 16 hours. Subsequently, a piece of cotton wool was soaked in 1:1 EtOH:demineralized water and placed on the film for 1 hour. After removal of the EtOH and 60 minutes recovery, the following results were obtained (a score of 1 indicates complete degradation of the film, 5 indicates no damage visible):

Performance and Stability Test

| Sample | Week 0 | Week 1 | Week 2 | Week 3 | Week 4 |
|---|---|---|---|---|---|
| Particle size C11 (nm) | 1387† | 423† | —* | —* | —* |
| Viscosity C11 (mPa · s) | 4032 | 600 | —* | —* | —* |
| Test C11 | 3 | 3 | —* | —* | —* |
| Test Blank | 1 | 1 | 1 | 1 | 1 |

*Crosslinker mixture gelled during second week of storage
†A reliable particle size measurement could not be obtained for this sample

The invention claimed is:

1. A multi-aziridine crosslinker composition, wherein the multi-aziridine crosslinker composition is an aqueous dispersion having a pH ranging from 8 to 14 and comprises a multi-aziridine compound in dispersed form, wherein said multi-aziridine compound has:
   a. from 2 to 6 of the following structural units A:

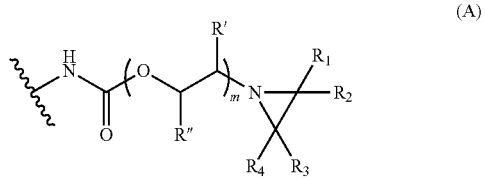

(A)

whereby
   $R_1$ is H,
   $R_2$ and $R_4$ are independently chosen from H or an aliphatic hydrocarbon group containing from 1 to 4 carbon atoms,
   $R_3$ is an aliphatic hydrocarbon group containing from 1 to 4 carbon atoms,
   m is 1,
   R' and R" are according to (1) or (2):
   (1) R'=H or an aliphatic hydrocarbon group containing from 1 to 14 carbon atoms, and
      R"=H, an aliphatic hydrocarbon group containing from 1 to 14 carbon atoms, a cycloaliphatic hydrocarbon group containing from 5 to 12 carbon atoms, an aromatic hydrocarbon group containing from 6 to 12 carbon atoms, CH$_2$—O—(C=O)—R''', CH$_2$—O—R'''', or CH$_2$—(OCR''''HCR''''H)$_n$—OR''''', whereby R''' is an aliphatic hydrocarbon group containing from 1 to 14 carbon atoms and R'''' is an aliphatic hydrocarbon group containing from 1 to 14 carbon atoms or an aromatic hydrocarbon group containing from 6 to 12 carbon atoms, n being from 1 to 35, R'''' independently being H or an aliphatic hydrocarbon group containing from 1 to 14 carbon atoms and R''''' being an aliphatic hydrocarbon group containing from 1 to 4 carbon atoms,
   (2) R' and R" form together a saturated cycloaliphatic hydrocarbon group containing from 5 to 8 carbon atoms;
   b. one or more linking chains wherein each one of these linking chains links two of the structural units A, whereby a linking chain is the shortest chain of consecutive atoms that links two structural units A; and
   c. a molecular weight in the range from 500 to 10000 Daltons wherein the molecular weight is determined using MALDI-TOF mass spectrometry.

2. The multi-aziridine crosslinker composition according to claim 1, wherein $R_2$ is H, $R_3$ is $C_2H_5$ and $R_4$ is H or $R_2$ is H, $R_3$ is $CH_3$ and $R_4$ is $CH_3$.

3. The multi-aziridine crosslinker composition according to claim 1, wherein $R_2$ is H, $R_3$ is $CH_3$ and $R_4$ is H.

4. The multi-aziridine crosslinker composition according to claim 1, wherein the linking chains consist of from 4 to 300 atoms and the linking chains are preferably a collection of atoms covalently connected which collection of atoms consists of i) carbon atoms, ii) carbon and nitrogen atoms, or iv) carbon, oxygen and nitrogen atoms.

5. The multi-aziridine crosslinker composition according to claim 1, wherein the multi-aziridine compound contains 2 or 3 structural units A.

6. The multi-aziridine crosslinker composition according to claim 1, wherein
   R' is H and R"=an alkyl group containing from 1 to 4 carbon atoms, CH2-O—(C=O)—R''', CH2-O—R'''', whereby R''' is an alkyl group containing from 3 to 12 carbon atoms and R'''' is an alkyl group containing from 1 to 14 carbon atoms.

7. The multi-aziridine crosslinker composition according to claim 1, wherein the multi-aziridine compound comprises one or more connecting groups wherein each one of these connecting groups connects two of the structural units A, whereby the connecting groups consist of at least one functionality selected from the group consisting of aliphatic hydrocarbon functionality, cycloaliphatic hydrocarbon functionality, aromatic hydrocarbon functionality, isocyanurate functionality, iminooxadiazindione functionality, ether functionality, ester functionality, amide functionality, carbonate functionality, urethane functionality, urea functionality, biuret functionality, allophanate functionality, uretdione functionality and any combination thereof.

8. The multi-aziridine crosslinker composition according to claim 7, wherein the connecting groups consist of at least one aliphatic hydrocarbon functionality and/or at least one cycloaliphatic hydrocarbon functionality, and further optionally an isocyanurate functionality or an iminooxadiazindione functionality.

9. The multi-aziridine crosslinker composition according to claim 7, wherein the connecting groups consist of at least one aliphatic hydrocarbon functionality and/or at least one cycloaliphatic hydrocarbon functionality, and further an isocyanurate functionality or an iminooxadiazindione functionality.

10. The multi-aziridine crosslinker composition according to claim 1, wherein the multi-aziridine compound comprises one or more connecting groups wherein each one of these connecting groups connects two of the structural units A, wherein the connecting groups consist of (i) at least two aliphatic hydrocarbon functionality and (ii) an isocyanurate functionality or an iminooxadiazindione functionality and wherein a pendant group is present on a connecting group, whereby the pendant group has the following structural formula:

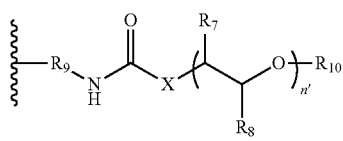

wherein n' is the number of repeating units and is an integer from 1 to 50,

X is O or NH, $R_7$ and $R_8$ are independently H or $CH_3$ in each repeating unit, $R_9$ is an aliphatic hydrocarbon group, and $R_{10}$ is an aliphatic hydrocarbon group containing from 1 to 20 carbon atoms, a cycloaliphatic hydrocarbon group containing from 5 to 20 carbon atoms or an aromatic hydrocarbon group containing from 6 to 20 carbon atoms.

11. The multi-aziridine crosslinker composition according to claim 1, wherein the number of consecutive C atoms and optionally O atoms between the N atom of the urethane group in a structural unit A and the next N atom which is either present in the linking chain or which is the N atom of the urethane group of another structural unit A is at most 9.

12. The multi-aziridine crosslinker composition according to claim 1, wherein the multi-aziridine compound is obtained by reacting at least a polyisocyanate with aliphatic reactivity in which all of the isocyanate groups are directly bonded to aliphatic or cycloaliphatic hydrocarbon groups, irrespective of whether aromatic hydrocarbon groups are also present, and a compound B with the following structural formula:

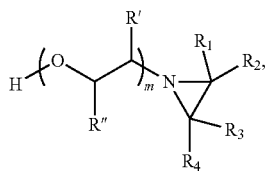

whereby the molar ratio of compound B to polyisocyanate is from 2 to 6.

13. The multi-aziridine crosslinker composition according to claim 12, wherein the multi-aziridine compound is the reaction product of a least compound (B), a polyisocyanate and alkoxy poly(propyleneglycol) and/or poly(propyleneglycol).

14. The multi-aziridine crosslinker composition according to claim 1, wherein the multi-aziridine compound has a molecular weight of from 600 to 5000 Daltons.

15. The multi-aziridine crosslinker composition according to claim 1, wherein the aqueous dispersion comprises aziridinyl group functional molecules having a molecular weight lower than 580 Daltons in an amount lower than 5 wt. %, on the total weight of the aqueous dispersion, whereby the molecular weight is determined using LC-MS.

16. The multi-aziridine crosslinker composition according to claim 1, wherein the pH of the aqueous dispersion is at most 13 at least 9.5.

17. The multi-aziridine crosslinker composition according to claim 1, wherein the amount of water in the aqueous dispersion is at least 15 wt. % and at most 95 wt. % on the total weight of the aqueous dispersion.

18. The multi-aziridine crosslinker composition according to claim 1, wherein the amount of said multi-aziridine compound in the aqueous dispersion is at least 5 wt. % and at most 70 wt. % on the total weight of the aqueous dispersion.

19. The multi-aziridine crosslinker composition according to claim 1, wherein the solids content of the aqueous dispersion is at least 5 and at most 70 wt. %.

20. The multi-aziridine crosslinker composition according to claim 1, wherein the multi-aziridine crosslinker composition comprises particles comprising said multi-aziridine compound, wherein said particles have a scatter intensity based average hydrodynamic diameter from 30 to 650 nanometer, determined using a method derived from ISO 22412:2017.

21. The multi-aziridine crosslinker composition according to claim 1, wherein the aqueous dispersion comprises a dispersant.

22. The multi-aziridine crosslinker composition according to claim 1, wherein the aqueous dispersion comprises a separate surface-active molecule component as dispersant in an amount ranging from 0.1 to 20 wt. %, on the total weight of the aqueous dispersion.

23. The multi-aziridine crosslinker composition according to claim 22, wherein the dispersant is a polymer having a number average molecular weight of at least 2000 Daltons and at most 1000000 Daltons and the polymer is a polyether, wherein the number average molecular weight is determined using MALDI-ToF mass spectrometry.

24. A method of preparing a two-component coating system comprising providing the multi-aziridine crosslinker composition according to claim 1 for crosslinking a carboxylic acid functional polymer dissolved and/or dispersed in an aqueous medium, whereby the carboxylic acid functional polymer contains carboxylic acid groups and/or carboxylate groups and the amounts of aziridinyl groups and of carboxylic acid groups and carboxylate groups are chosen such that the stoichiometric amount (SA) of aziridinyl groups on carboxylic acid groups and carboxylate groups is from 0.1 to 2.0.

25. A two-component coating system comprising a first component and a second component each of which is separate and distinct from each other and wherein the first component comprises a carboxylic acid functional polymer dissolved and/or dispersed in an aqueous medium, whereby the carboxylic acid functional polymer contains carboxylic acid groups and/or carboxylate groups and the second component comprises the multi-aziridine crosslinker composition according to claim 1.

* * * * *

UNITED STATES PATENT AND TRADEMARK OFFICE
CERTIFICATE OF CORRECTION

| | | |
|---|---|---|
| PATENT NO. | : 12,398,098 B2 | Page 1 of 1 |
| APPLICATION NO. | : 17/791765 | |
| DATED | : August 26, 2025 | |
| INVENTOR(S) | : Gerardus Cornelis Overbeek et al. | |

It is certified that error appears in the above-identified patent and that said Letters Patent is hereby corrected as shown below:

In the Claims

Column 129, Line 51, Claim 1, delete "R" =H," and insert -- R" = --

Signed and Sealed this
Seventh Day of October, 2025

John A. Squires
*Director of the United States Patent and Trademark Office*